US012692243B2

(12) United States Patent
Lee et al.

(10) Patent No.: US 12,692,243 B2
(45) Date of Patent: Jul. 28, 2026

(54) ORGANIC LIGHT EMITTING DIODE

(71) Applicant: LG CHEM, LTD., Seoul (KR)

(72) Inventors: Woochul Lee, Daejeon (KR); Ji Young Choi, Daejeon (KR); Sang Duk Suh, Daejeon (KR); Joo Ho Kim, Daejeon (KR); Hoon Jun Kim, Daejeon (KR); Dong Hoon Lee, Daejeon (KR)

(73) Assignee: LG CHEM, LTD., Seoul (KR)

( * ) Notice: Subject to any disclaimer, the term of this patent is extended or adjusted under 35 U.S.C. 154(b) by 963 days.

(21) Appl. No.: 17/057,832

(22) PCT Filed: Aug. 20, 2019

(86) PCT No.: PCT/KR2019/010544

§ 371 (c)(1),
(2) Date: Nov. 23, 2020

(87) PCT Pub. No.: WO2020/040514

PCT Pub. Date: Feb. 27, 2020

(65) Prior Publication Data

US 2022/0093868 A1 Mar. 24, 2022

(30) Foreign Application Priority Data

Aug. 20, 2018 (KR) ........................ 10-2018-0097023

(51) Int. Cl.
*C07D 307/91* (2006.01)
*C07C 15/28* (2006.01)
(Continued)

(52) U.S. Cl.
CPC ............ *C07D 307/91* (2013.01); *C07C 15/28* (2013.01); *C07F 5/027* (2013.01); *C09K 11/06* (2013.01);
(Continued)

(58) Field of Classification Search
CPC ........................... H10K 85/322; H10K 85/626
See application file for complete search history.

(56) References Cited

U.S. PATENT DOCUMENTS 8,890,131 B2 11/2014 Lecloux et al.
2004/0251816 A1 12/2004 Leo et al.
(Continued)

FOREIGN PATENT DOCUMENTS

CN 108026060 5/2018
CN 108137527 6/2018
(Continued)

OTHER PUBLICATIONS

International Search Report and the Written Opinion of PCT/KR2019/010544, mailed Nov. 26, 2019.
(Continued)

*Primary Examiner* — Sean M DeGuire
(74) *Attorney, Agent, or Firm* — Bryan Cave Leighton Paisner LLP

(57) ABSTRACT

Provided is an organic light emitting device comprising a first electrode; a second electrode provided to face the first electrode; and an organic material layer having one or more layers provided between the first electrode and the second electrode, wherein a compound of the following Formula 1
(Continued)

is included as a host in the organic material layer having one or more layers, and a compound of the following Formula 2 is included as a dopant in the organic material layer having one or more layers:

Formula 1

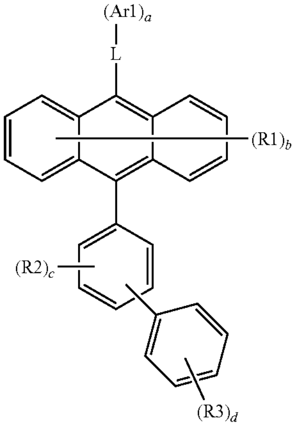

Formula 2

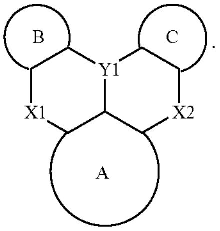

7 Claims, 1 Drawing Sheet

(51) Int. Cl.

| | |
|---|---|
| ***C07F 5/02*** | (2006.01) |
| ***C09K 11/06*** | (2006.01) |
| ***H10K 50/11*** | (2023.01) |
| ***H10K 50/15*** | (2023.01) |
| ***H10K 50/16*** | (2023.01) |
| ***H10K 50/17*** | (2023.01) |
| ***H10K 85/60*** | (2023.01) |

(52) U.S. Cl.

CPC ....... *H10K 85/626* (2023.02); *H10K 85/6574* (2023.02); *H10K 85/658* (2023.02); *C07C 2603/24* (2017.05); *C07C 2603/26* (2017.05); *C09K 2211/1007* (2013.01); *C09K 2211/1011* (2013.01); *C09K 2211/1018* (2013.01); *H10K 50/11* (2023.02); *H10K 50/15* (2023.02); *H10K 50/16* (2023.02); *H10K 50/171* (2023.02)

(56) References Cited

U.S. PATENT DOCUMENTS

| | | | | |
|---|---|---|---|---|
| 2007/0055085 | A1* | 3/2007 | Kubota .................. | H05B 33/14 428/917 |
| 2008/0315754 | A1* | 12/2008 | Kawamura ........ | H10K 85/6576 549/469 |
| 2015/0357574 | A1 | 12/2015 | Ito et al. | |
| 2016/0020405 | A1 | 1/2016 | Ito et al. | |
| 2018/0069182 | A1 | 3/2018 | Hatakeyama et al. | |
| 2018/0287068 | A1 | 10/2018 | Ha et al. | |
| 2019/0058124 | A1* | 2/2019 | Hatakeyama ........... | C07F 5/027 |
| 2019/0115538 | A1* | 4/2019 | Lim ..................... | H10K 85/626 |
| 2019/0207112 | A1 | 7/2019 | Hatakeyama et al. | |
| 2020/0058885 | A1 | 2/2020 | Hong et al. | |
| 2020/0091431 | A1 | 3/2020 | Hatakeyama et al. | |
| 2020/0123181 | A1 | 4/2020 | Choi et al. | |
| 2020/0144514 | A1 | 5/2020 | Hatakeyama et al. | |
| 2020/0190116 | A1 | 6/2020 | Hatakeyama et al. | |

FOREIGN PATENT DOCUMENTS

| | | |
|---|---|---|
| JP | 2017-193618 | 10/2017 |
| KR | 10-2015-0141271 | 12/2015 |
| KR | 10-2016-0007984 | 1/2016 |
| KR | 10-2016-0119683 | 10/2016 |
| KR | 10-2017-0130434 | 11/2017 |
| KR | 10-2017-0130435 | 11/2017 |
| KR | 10-2018-0122298 | 11/2018 |
| WO | 2003-012890 | 2/2003 |
| WO | 2017138526 | 8/2017 |
| WO | 2017-188111 | 11/2017 |
| WO | 2018-186374 | 10/2018 |

OTHER PUBLICATIONS

Office Action of Korean Patent Office in Appl'n No. 10-2019-0101660, dated Aug. 18, 2020.

* cited by examiner

ORGANIC LIGHT EMITTING DIODE

CROSS-REFERENCE TO RELATED APPLICATIONS

This application is a National Stage Application of International Application No. PCT/KR2019/010544 filed on Aug. 20, 2019, which claims priority to and the benefit of Korean Patent Application No. 10-2018-0097023 filed in the Korean Intellectual Property Office on Aug. 20, 2018, the entire contents of which are incorporated herein by reference.

TECHNICAL FIELD

The present application relates to an organic light emitting device.

BACKGROUND

In general, an organic light emitting phenomenon refers to a phenomenon in which electric energy is converted into light energy by using an organic material. An organic light emitting device using the organic light emitting phenomenon usually has a structure including a positive electrode, a negative electrode, and an organic material layer interposed therebetween. Here, the organic material layer has in many cases a multi-layered structure composed of different materials in order to improve the efficiency and stability of the organic light emitting device, and for example, can be composed of a hole injection layer, a hole transport layer, a light emitting layer, an electron transport layer, an electron injection layer, and the like. In such a structure of the organic light emitting device, if a voltage is applied between the two electrodes, holes are injected from the positive electrode into the organic material layer and electrons are injected from the negative electrode into the organic material layer, and when the injected holes and electrons meet each other, an exciton is formed, and light is emitted when the exciton falls down again to a ground state.

There is a continuous need for developing a new material for the aforementioned organic light emitting device.

BRIEF DESCRIPTION

Technical Problem

The present application relates to an organic light emitting device.

Technical Solution

The present application has been made in an effort to provide an organic light emitting device including: a first electrode; a second electrode provided to face the first electrode; and an organic material layer having one or more layers provided between the first electrode and the second electrode, in which a compound of the following Formula 1 is included as a host in the organic material layer having one or more layers, and a compound of the following Formula 2 is included as a dopant in the organic material layer having one or more layers:

Formula 1

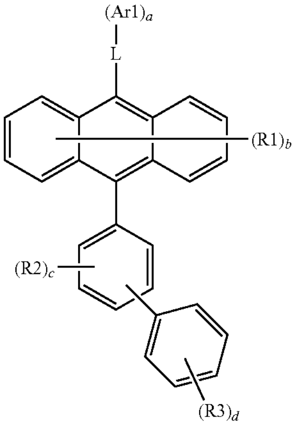

wherein in Formula 1:

L is a phenylene group which is unsubstituted or substituted with one or more substituents selected from the group consisting of an aryl group and deuterium;

Ar1 is a substituted or unsubstituted aryl group or a substituted or unsubstituted heterocyclic group;

R1 is hydrogen, deuterium, a halogen group, a cyano group, a substituted or unsubstituted alkyl group, a substituted or unsubstituted silyl group, a substituted or unsubstituted alkoxy group, a substituted or unsubstituted aryl group, or a substituted or unsubstituted heterocyclic group;

R2 and R3 the same as or different from each other, and are each independently hydrogen or deuterium;

a is an integer from 1 to 5;

b is an integer from 1 to 8;

c is an integer from 1 to 4;

d is an integer from 1 to 5;

when a is 2 or more, two or more Ar1s are the same as or different from each other, when b is 2 or more, two or more R1s are the same as or different from each other, when c is 2 or more, two or more R2s are the same as or different from each other, and when d is 2 or more, two or more R3s are the same as or different from each other;

Formula 2

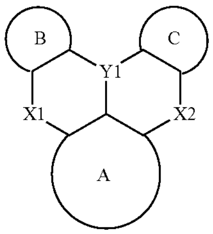

wherein in Formula 2:

A, B, and C are each a substituted or unsubstituted aromatic hydrocarbon ring or a substituted or unsubstituted hetero ring;

Y1 is boron or phosphine oxide;

X1 and X2 are each O or NR;

R is hydrogen, deuterium, a halogen group, a cyano group, a substituted or unsubstituted alkyl group; a substituted or unsubstituted silyl group, a substituted or unsubstituted alkoxy group, a substituted or unsubstituted aryl group, or a substituted or unsubstituted heterocyclic group; and adjacent groups of R, B, and C can be bonded to each other to form a ring.

Advantageous Effects

An organic light emitting device using the compound according to an exemplary embodiment of the present application can have a low driving voltage, high light emitting efficiency and/or a long service life.

EXPLANATION OF REFERENCE NUMERALS AND SYMBOLS

Figure 1:
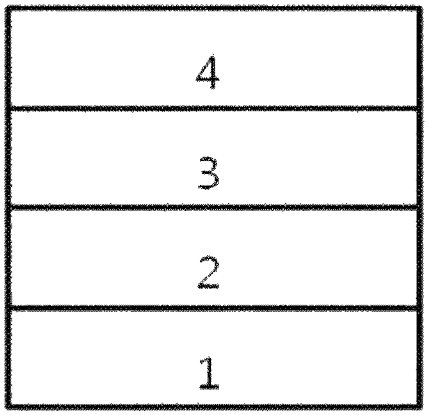
FIG. 1 illustrates an example of an organic light emitting device in which a substrate 1, a positive electrode 2, a light emitting layer 3, and a negative electrode 4 are sequentially stacked.

1: Substrate
2: Positive electrode
3: Light emitting layer
4: Negative electrode
5: Hole injection layer
6: Hole transport layer
7: Electron transport layer

DETAILED DESCRIPTION

Hereinafter, the present specification will be described in more detail.

The present specification provides an organic light emitting device including the compounds of Formulae 1 and 2.

Specifically, an exemplary embodiment of the present specification includes the compound of Formula 1, including anthracene, as a host, and includes the compound of Formula 2, including boron, as a dopant. When a light emitting layer is formed using the compounds of Formulae 1 and 2 at an appropriate ratio, dark blue light emission can be produced and high light emitting efficiency can be exhibited. Further, the emission wavelength of the compound including anthracene and the absorption wavelength of the compound including boron are frequently overlapped, so that energy is easily transferred from the host to the dopant.

In addition, in the case of the compound of Formula 1, the 9 and 10 positions of anthracene are substituted with a phenylene group, thereby exhibiting an effect in that light emission efficiency is further increased as compared to the case where the 9 and 10 positions of anthracene are substituted with a naphthylene group.

Examples of the substituents in the present specification will be described below, but are not limited thereto.

The term "substitution" means that a hydrogen atom bonded to a carbon atom of a compound is changed into another substituent, and a position to be substituted is not limited as long as the position is a position at which the hydrogen atom is substituted, that is, a position at which the substituent can be substituted, and when two or more are substituted, the two or more substituents can be the same as or different from each other.

In the present specification, the term "substituted or unsubstituted" means being substituted with one or two or more substituents selected from the group consisting of hydrogen, a halogen group, a nitrile group, a nitro group, a hydroxy group, a substituted or unsubstituted alkyl group, a substituted or unsubstituted cycloalkyl group, a substituted or unsubstituted alkenyl group, a substituted or unsubstituted amine group, a substituted or unsubstituted aryl group, and a substituted or unsubstituted heterocyclic group, or being substituted with a substituent to which two or more substituents are linked among the substituents exemplified above, or having no substituent. For example, "the substituent to which two or more substituents are linked" can be a biphenyl group. That is, the biphenyl group can also be an aryl group, and can be interpreted as a substituent to which two phenyl groups are linked.

In the present specification, examples of a halogen group include fluorine, chlorine, bromine or iodine.

In the present specification, the alkyl group can be straight-chained or branched, and the number of carbon atoms thereof is not particularly limited, but is preferably 1 to 50. Specific examples thereof include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethyl-heptyl, 1-ethyl-propyl, 1,1-dimethyl-propyl, isohexyl, 4-methylhexyl, 5-methylhexyl, and the like, but are not limited thereto.

In the present specification, the cycloalkyl group is not particularly limited, but is preferably a cycloalkyl group having 3 to 60 carbon atoms, and specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, the alkoxy group can be straight-chained, branched, or cyclic. The number of carbon atoms of the alkoxy group is not particularly limited, but is preferably 1 to 20. Specific examples thereof include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, and the like, but are not limited thereto.

In the present specification, the alkenyl group can be straight-chained or branched, and the number of carbon atoms thereof is not particularly limited, but is preferably 2 to 40. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenyl-vinyl-1-yl, 2-phenylvinyl-1-yl, 2,2-diphenyl-vinyl-1-yl, 2-phenyl-2-(naphthyl-1-yl)vinyl-1-yl, 2,2-bis(di-phenyl-1-yl)vinyl-1-yl, a stilbenyl group, a styrenyl group, and the like, but are not limited thereto.

In the present specification, when the aryl group is a monocyclic aryl group, the number of carbon atoms thereof is not particularly limited, but is preferably 6 to 25. Specific examples of the monocyclic aryl group include a phenyl group, a biphenyl group, a terphenyl group, and the like, but are not limited thereto.

When the aryl group is a polycyclic aryl group, the number of carbon atoms thereof is not particularly limited, but is preferably 10 to 24. Specific examples of the polycyclic aryl group include a naphthyl group, an anthracenyl group, a phenanthryl group, a pyrenyl group, a perylenyl group, a chrysenyl group, a fluorenyl group, and the like, but are not limited thereto.

In the present specification, the fluorenyl group can be substituted, and adjacent substituents can be bonded to each other to form a ring.

When the fluorenyl group is substituted, the substituent can be

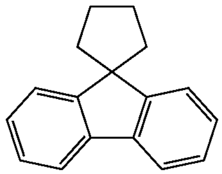,
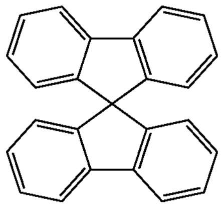,
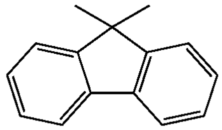,
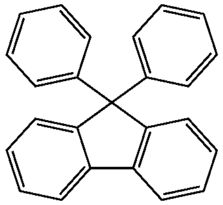, and the like, but is not limited thereto.

In the present specification, a heterocyclic group includes one or more atoms other than carbon, that is, one or more heteroatoms, and specifically, the heteroatom can include one or more atoms selected from the group consisting of O, N, Se, S. and the like. The number of carbon atoms of the heterocyclic group is not particularly limited, but is preferably 2 to 60. Examples of the heterocyclic group include a thiophene group, a furan group, a pyrrole group, an imidazole group, a thiazole group, an oxazole group, an oxadiazole group, a triazole group, a pyridyl group, a bipyridyl group, a pyrimidyl group, a triazine group, a triazole group, an acridyl group, a pyridazine group, a pyrazinyl group, a qinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazole group, a benzo-carbazole group, a benzothiophene group, a dibenzothiophene group, a benzofuranyl group, a phenanthroline group, a thiazolyl group, an isoxazolyl group, an oxadiazolyl group, a thiadiazolyl group, a benzothiazolyl group, a phenothiazinyl group, a dibenzofuranyl group, and the like, but are not limited thereto.

In the present specification, the above-described description on the aryl group can be applied to an aromatic hydrocarbon ring except for a divalent aromatic hydrocarbon ring.

In the present specification, the above-described description on the heterocyclic group can be applied to a hetero ring except for a divalent hetero ring.

In the present specification, a substituted or unsubstituted aromatic hydrocarbon ring is a divalent or more group.

In the present specification, a substituted or unsubstituted hetero ring is a divalent or more group.

In the present specification, the above-described description on the aryl group can be applied to an aryl group of an arylamine group.

In the present specification, the meaning of bonding to an adjacent group to form a ring means bonding to an adjacent group to form a substituted or unsubstituted aliphatic hydrocarbon ring, a substituted or unsubstituted aromatic hydrocarbon ring, a substituted or unsubstituted aliphatic hetero ring, or a substituted or unsubstituted aromatic hetero ring.

In the present specification, the aliphatic hydrocarbon ring means a ring composed of only carbon and hydrogen atoms as a ring which is not an aromatic group.

In the present specification, examples of an aromatic hydrocarbon ring include a benzene ring, a naphthalene ring, an anthracene ring, and the like, but are not limited thereto.

In the present specification, an aliphatic hetero ring means an aliphatic ring including one or more of hetero atoms.

In the present specification, an aromatic hetero ring means an aromatic ring including one or more of hetero atoms.

In the present specification, the aliphatic hydrocarbon ring, the aromatic hydrocarbon ring, the aliphatic hetero ring, and the aromatic hetero ring can be monocyclic or polycyclic.

In the present specification, the "adjacent" group means a substituent substituted with an atom directly linked to an atom in which the corresponding substituent is substituted, a substituent disposed sterically closest to the corresponding substituent, or another substituent substituted with an atom in which the corresponding substituent is substituted. For example, two substituents substituted at the ortho position in a benzene ring and two substituents substituted with the same carbon in an aliphatic ring can be interpreted as groups which are "adjacent" to each other.

In the present specification, the case where adjacent groups are bonded to each other to form a ring means that adjacent groups are bonded to each other to form a 5-membered to 8-membered hydrocarbon ring or a 5-membered to 8-membered hetero ring as described above, and the ring can be monocyclic or polycyclic, can be an aliphatic ring, an aromatic ring, or a fused form thereof, and is not limited thereto.

According to an exemplary embodiment of the present application, L is a phenylene group which is unsubstituted or substituted with one or more substituents selected from the group consisting of an aryl group and deuterium.

According to an exemplary embodiment of the present application, L is a phenylene group which is unsubstituted or substituted with one or more substituents selected from the group consisting of a phenyl group, a naphthyl group, and deuterium.

According to an exemplary embodiment of the present application, L is a phenylene group which is unsubstituted or substituted with one substituent selected from the group consisting of a phenyl group, a naphthyl group, and deuterium.

According to an exemplary embodiment of the present application, L is a phenylene group which is substituted with a phenyl group; a phenylene group which is substituted with a naphthyl group; a phenylene group which is substituted with deuterium; or a phenylene group.

According to an exemplary embodiment of the present application, Ar1 is a substituted or unsubstituted aryl group or a substituted or unsubstituted heterocyclic group.

Further, according to an exemplary embodiment of the present application, Ar1 is a substituted or unsubstituted aryl group having 6 to 60 carbon atoms, or a substituted or unsubstituted heterocyclic group having 3 to 60 carbon atoms.

In addition, according to an exemplary embodiment of the present application, Ar1 is a substituted or unsubstituted aryl group having 6 to 30 carbon atoms, or a substituted or unsubstituted heterocyclic group having 3 to 30 carbon atoms.

According to an exemplary embodiment of the present application, Ar1 is a substituted or unsubstituted aryl group, a dibenzofuran group, a dibenzothiophene group, or a substituted or unsubstituted carbazole group.

According to an exemplary embodiment of the present application, Ar1 is a substituted or unsubstituted phenyl group, a substituted or unsubstituted naphthyl group, a substituted or unsubstituted phenanthrene group, a substituted or unsubstituted pyrene group, a substituted or unsubstituted triphenylene group, a dibenzofuran group; a dibenzothiophene group, or a substituted or unsubstituted carbazole group.

According to an exemplary embodiment of the present application, Ar1 is a phenyl group which is unsubstituted or substituted with deuterium; a naphthyl group which is unsubstituted or substituted with deuterium; a phenanthrene group which is unsubstituted or substituted with deuterium; a pyrene group which is unsubstituted or substituted with deuterium; a triphenylene group which is unsubstituted or substituted with deuterium; a dibenzofuran group; a dibenzothiophene group; or a carbazole group which is unsubstituted or substituted with a phenyl group.

According to an exemplary embodiment of the present application, a is an integer from 1 to 5.

According to an exemplary embodiment of the present application, a is 1 or 2.

According to an exemplary embodiment of the present application, R1 is hydrogen, deuterium, a substituted or unsubstituted alkyl group, a substituted or unsubstituted aryl group, or a substituted or unsubstituted heterocyclic group.

According to an exemplary embodiment of the present application, R1 is hydrogen, deuterium, a substituted or unsubstituted aryl group, or a substituted or unsubstituted heterocyclic group.

According to an exemplary embodiment of the present application, R1 is hydrogen or deuterium.

According to an exemplary embodiment of the present application, b is an integer from 1 to 8.

According to an exemplary embodiment of the present application, b is 8.

According to an exemplary embodiment of the present application, R2 and R3 are the same as or different from each other, and are each independently hydrogen or deuterium.

According to an exemplary embodiment of the present application, c is an integer from 1 to 4.

According to an exemplary embodiment of the present application, c is 4.

According to an exemplary embodiment of the present application, d is an integer from 1 to 5.

According to an exemplary embodiment of the present application, d is 5.

According to an exemplary embodiment of the present application, A, B, and C are each a substituted or unsubstituted aromatic hydrocarbon ring or a substituted or unsubstituted hetero ring.

According to an exemplary embodiment of the present application, A, B, and C are each a substituted or unsubstituted aromatic hydrocarbon ring having 6 to 60 carbon atoms, or a substituted or unsubstituted hetero ring having 3 to 60 carbon atoms.

According to an exemplary embodiment of the present application, A, B, and C are each a substituted or unsubstituted aromatic hydrocarbon ring having 6 to 30 carbon atoms, or a substituted or unsubstituted hetero ring having 3 to 30 carbon atoms.

According to an exemplary embodiment of the present application, A, B, and C are each an aromatic hydrocarbon ring which is unsubstituted or substituted with one or more substituents selected from the group consisting of an alkyl group, an amine group, and a heterocyclic group; or a hetero ring which is unsubstituted or substituted with one or more substituents selected from the group consisting of an alkyl group, an amine group, and a heterocyclic group.

According to an exemplary embodiment of the present application, A, B, and C are each an aromatic hydrocarbon ring having 6 to 30 carbon atoms, which is unsubstituted or substituted with one or more substituents selected from the group consisting of an alkyl group, an amine group, and a heterocyclic group; or a hetero ring having 3 to 30 carbon atoms, which is unsubstituted or substituted with one or more substituents selected from the group consisting of an alkyl group, an amine group, and a heterocyclic group.

According to an exemplary embodiment of the present application, A, B, and C are each a substituted or unsubstituted divalent or more aryl group, or a substituted or unsubstituted divalent or more heterocyclic group.

According to an exemplary embodiment of the present application, A, B, and C are each a substituted or unsubstituted divalent aryl group, or a substituted or unsubstituted divalent heterocyclic group.

According to an exemplary embodiment of the present application, A, B, and C are each a phenyl group which is unsubstituted or substituted with one or more substituents selected from the group consisting of an alkyl group, an amine group, and a heterocyclic group; a naphthyl group which is unsubstituted or substituted with one or more substituents selected from the group consisting of an alkyl group, an amine group, and a heterocyclic group; or a dibenzofuran group which is unsubstituted or substituted with one or more substituents selected from the group consisting of an alkyl group, an amine group, and a heterocyclic group. In this case, the phenyl group, the naphthyl group, and the dibenzofuran group can be divalent or more.

According to an exemplary embodiment of the present application, Y1 is boron or phosphine oxide.

According to an exemplary embodiment of the present application, Y1 is boron.

According to an exemplary embodiment of the present application, X1 and X2 are each O or NR.

According to an exemplary embodiment of the present application, R is hydrogen, deuterium, a halogen group, a cyano group, a substituted or unsubstituted alkyl group, a substituted or unsubstituted silyl group, a substituted or unsubstituted alkoxy group, a substituted or unsubstituted aryl group, or a substituted or unsubstituted heterocyclic group.

According to an exemplary embodiment of the present application, R is a substituted or unsubstituted alkyl group, a substituted or unsubstituted aryl group, or a substituted or unsubstituted heterocyclic group.

According to an exemplary embodiment of the present application, R is a substituted or unsubstituted aryl group.

According to an exemplary embodiment of the present application, R is a substituted or unsubstituted phenyl group, or a substituted or unsubstituted naphthyl group.

According to an exemplary embodiment of the present application, R is a phenyl group which is unsubstituted or substituted with an alkyl group, or a naphthyl group which is unsubstituted or substituted with an alkyl group.

According to an exemplary embodiment of the present application, R is a phenyl group which is unsubstituted or substituted with an alkyl group, or a naphthyl group.

According to an exemplary embodiment of the present application, adjacent groups of R, B, and C can be bonded to each other to form a ring.

According to an exemplary embodiment of the present application, adjacent groups of R, B, and C can be bonded to each other to form a substituted or unsubstituted aromatic hydrocarbon ring or a substituted or unsubstituted hetero ring.

According to an exemplary embodiment of the present application, adjacent groups of R, B, and C can be bonded to each other to form a substituted or unsubstituted aromatic hydrocarbon ring having 6 to 60 carbon atoms or a substituted or unsubstituted hetero ring having 2 to 60 carbon atoms.

According to an exemplary embodiment of the present application, adjacent groups of R, B, and C can be bonded to each other to form a substituted or unsubstituted aromatic hydrocarbon ring having 6 to 30 carbon atoms or a substituted or unsubstituted hetero ring having 2 to 30 carbon atoms.

Formula 2 of the present application can be the following Formula 2-1:

Formula 2-1

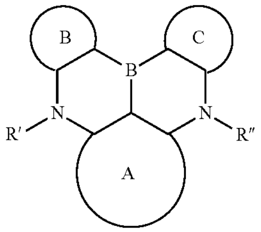

wherein in Formula 2-1:

the definitions of A, B, and C are the same as those defined in Formula 2;

R' and R" are each independently a substituted or unsubstituted aryl group or a substituted or unsubstituted heterocyclic group; and adjacent groups of R', B, C, and R" can be bonded to each other to form a substituted or unsubstituted aromatic hydrocarbon ring or a substituted or unsubstituted hetero ring.

According to an exemplary embodiment of the present application, a compound of Formula 1 is selected from among the following compounds:

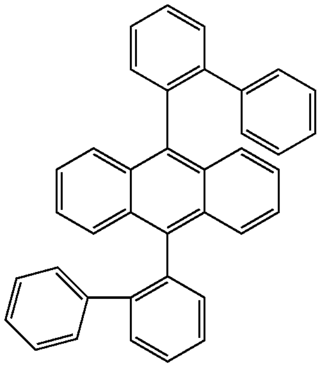

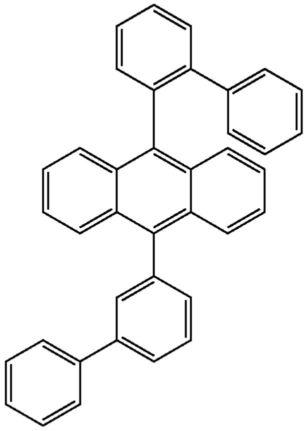

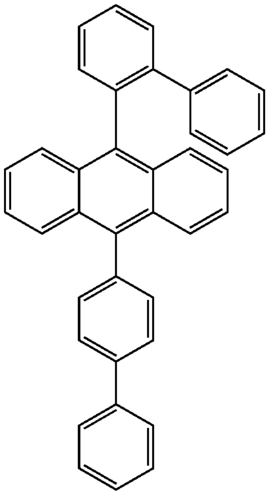

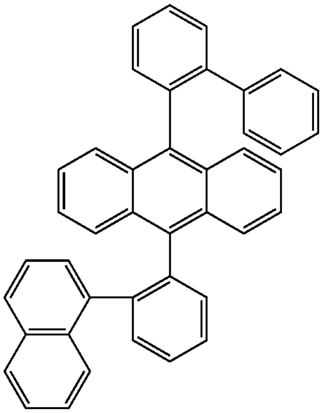

-continued
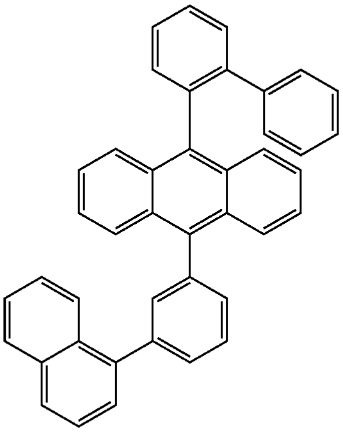
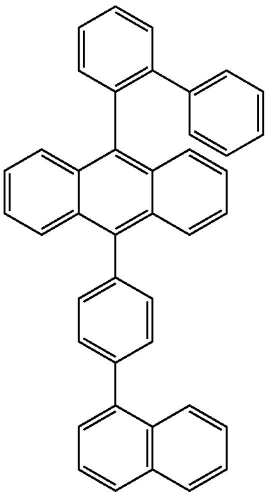
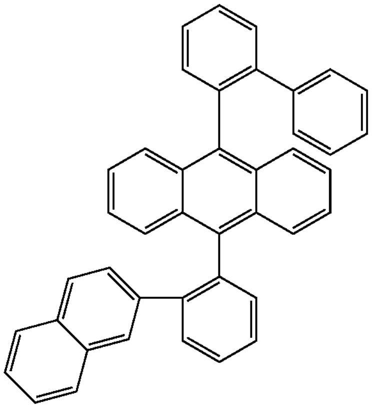
-continued
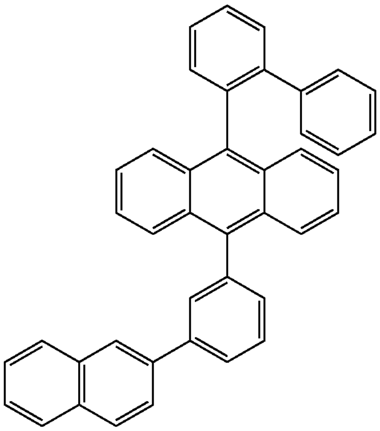
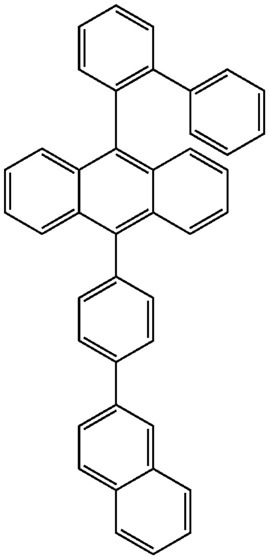
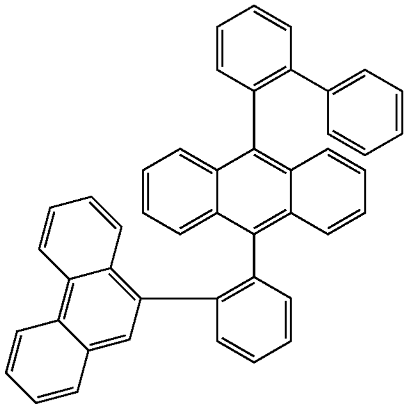

-continued
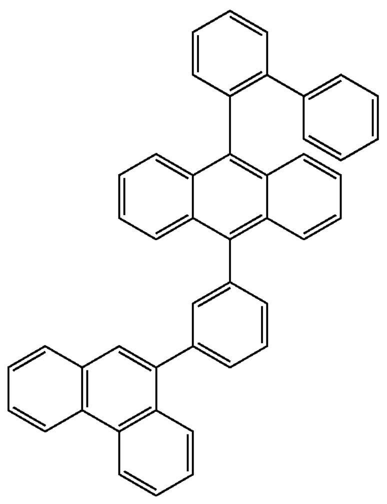
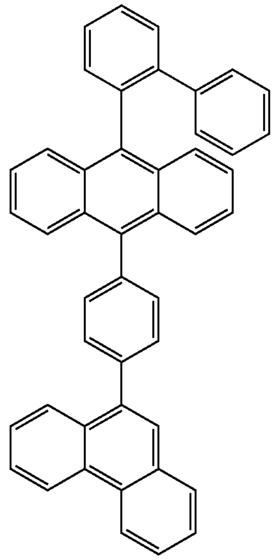
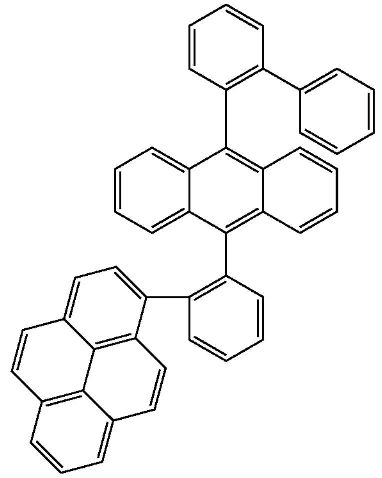
-continued
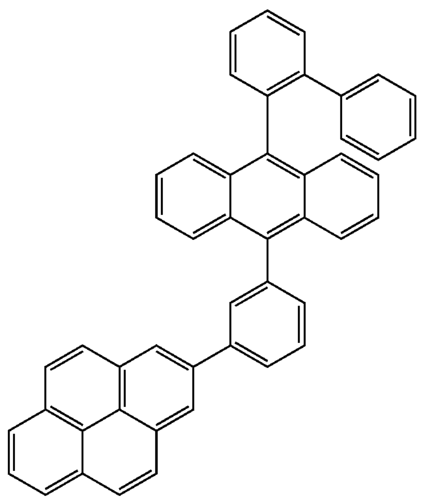
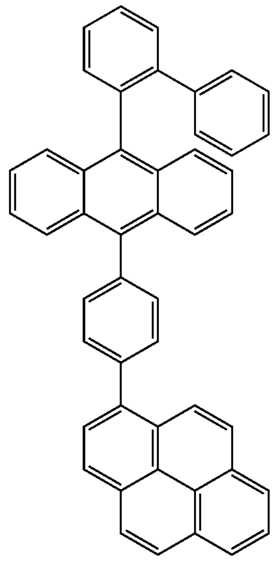
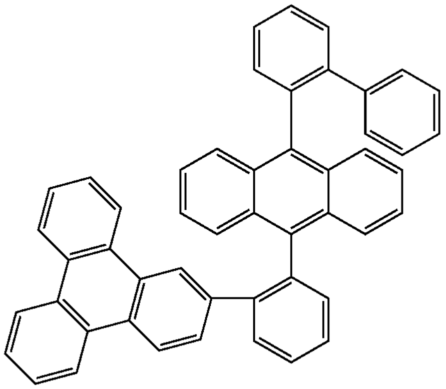

-continued
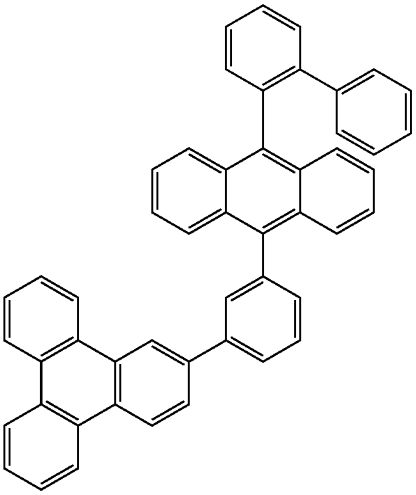
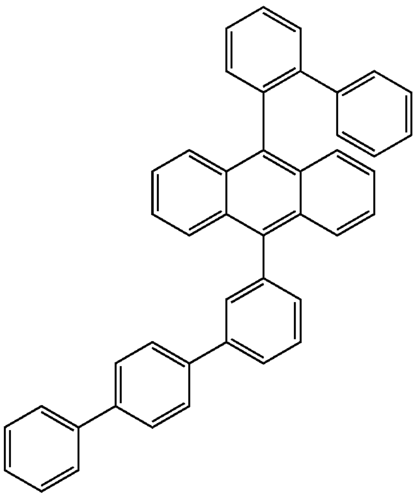
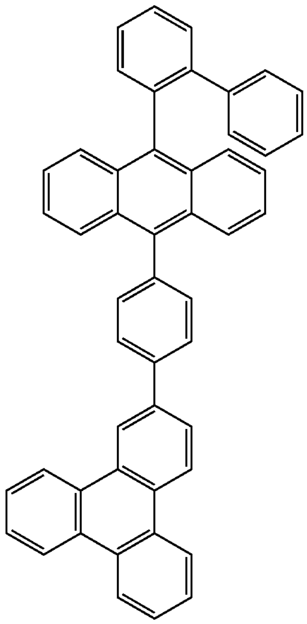
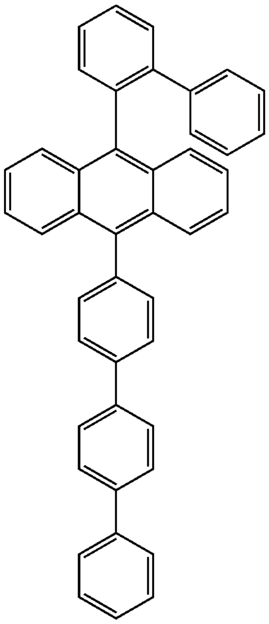
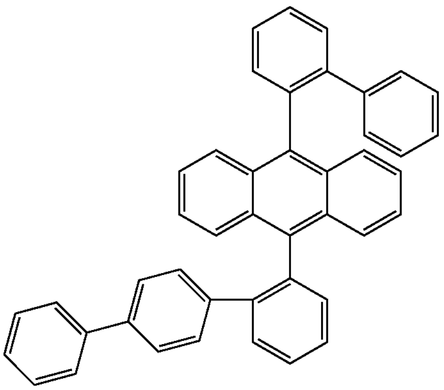
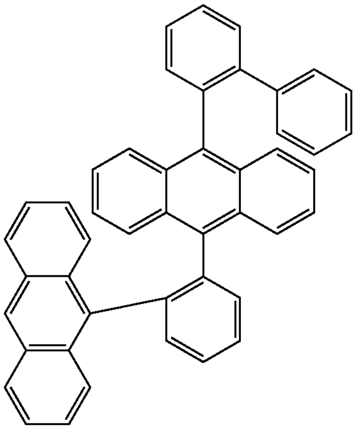

-continued
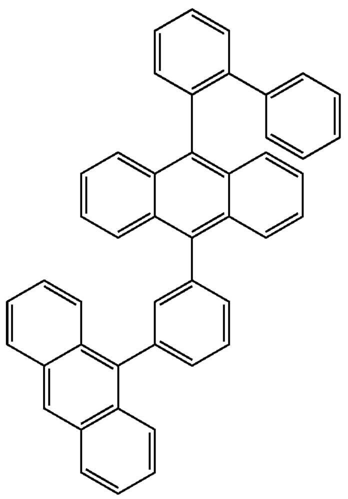
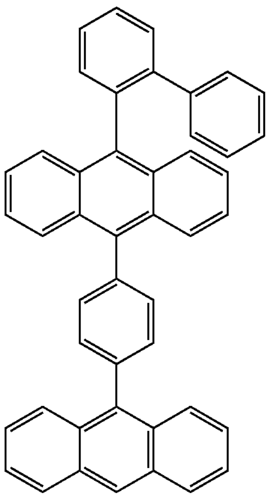
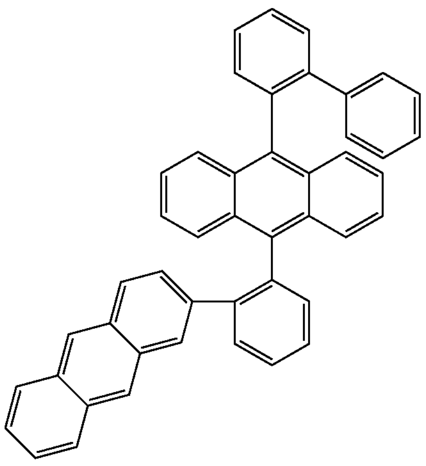
-continued
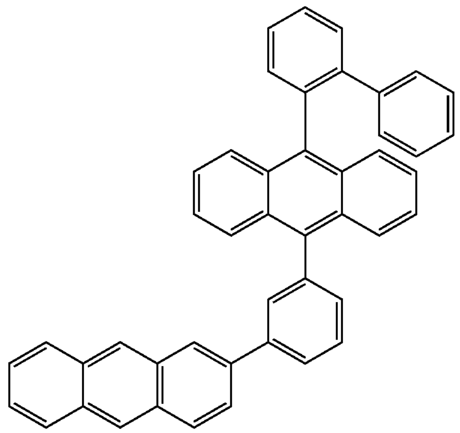
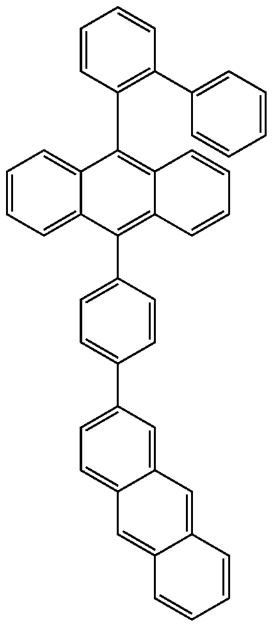
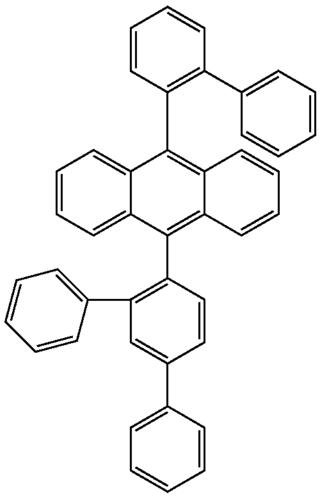

-continued
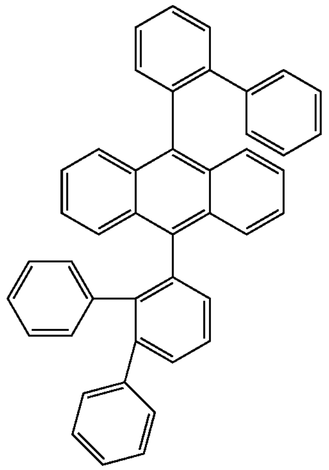
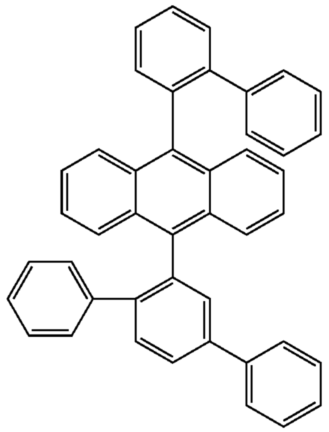
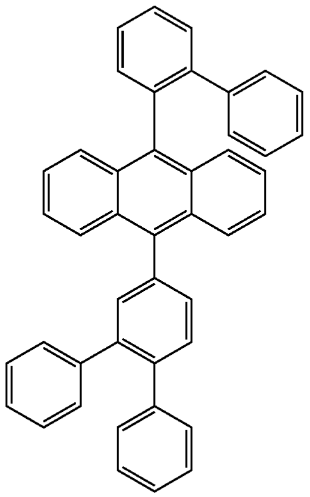
-continued
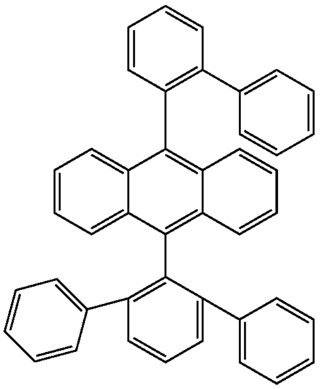
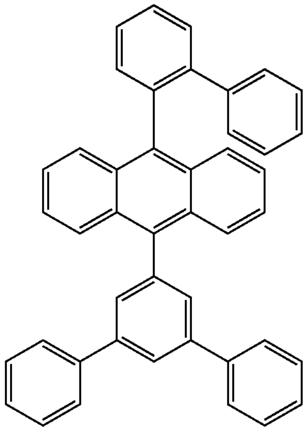
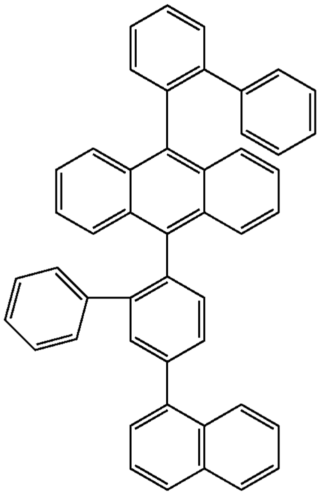

-continued
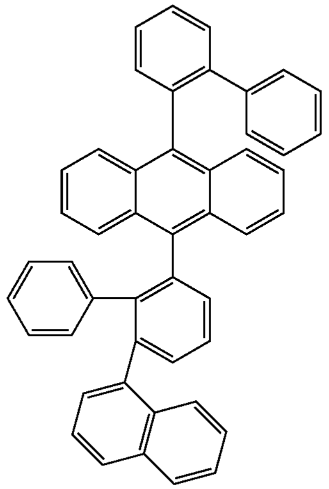
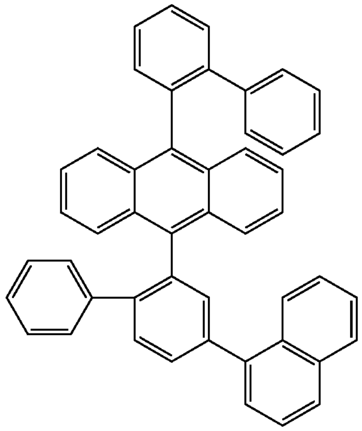
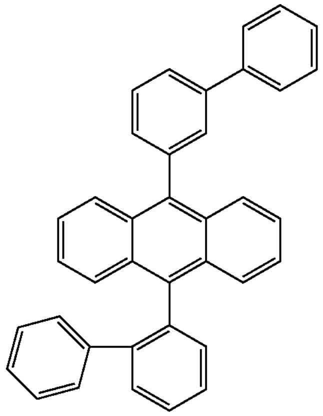
-continued
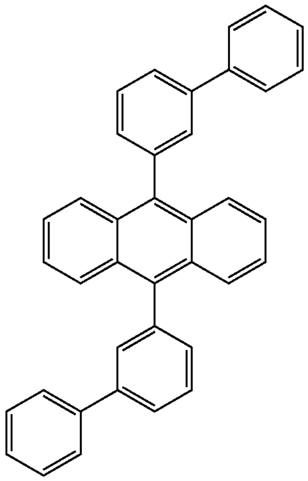
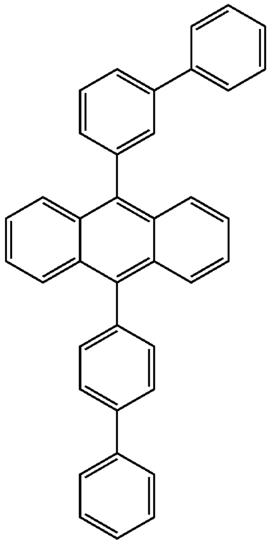
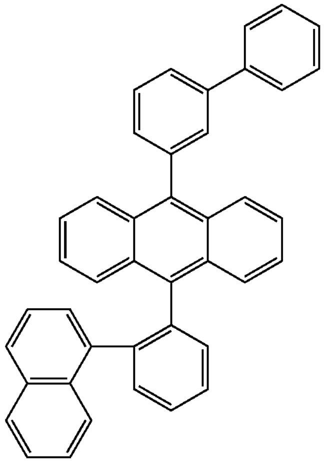

-continued
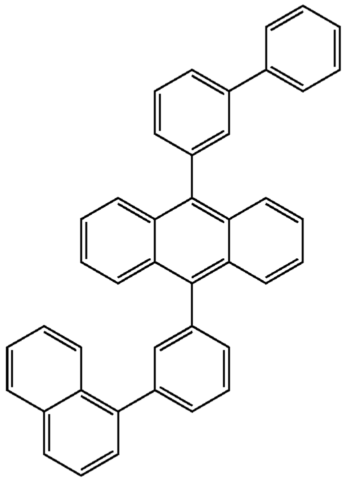
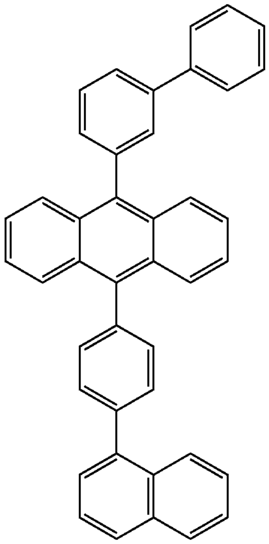
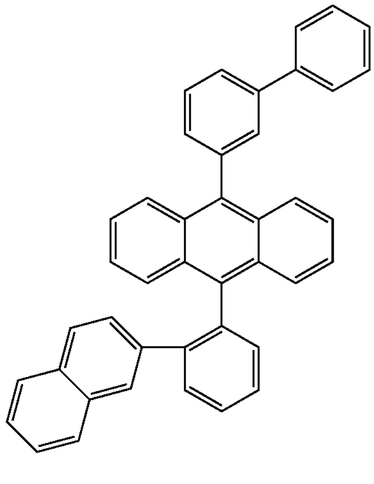
-continued
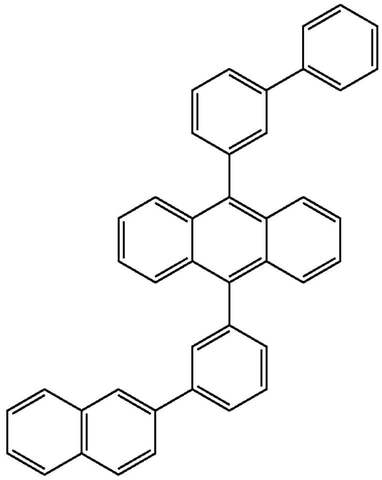
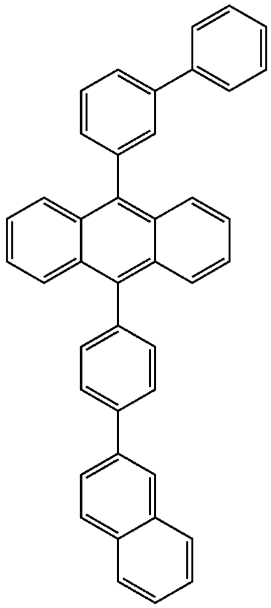
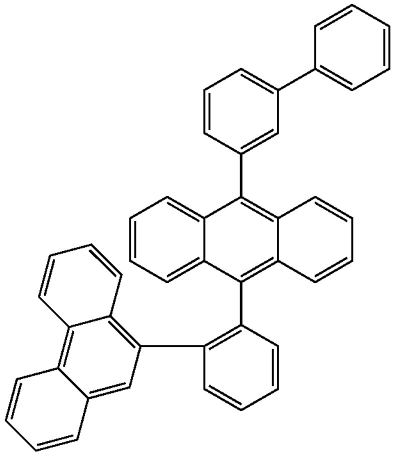

-continued
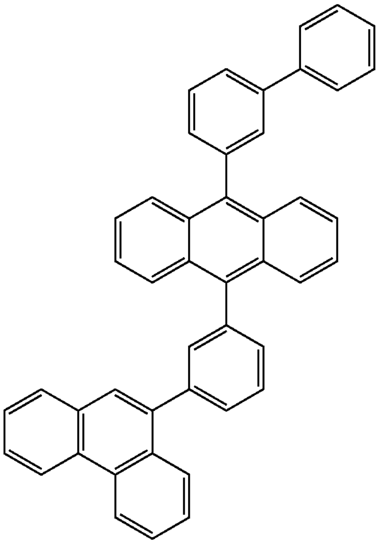
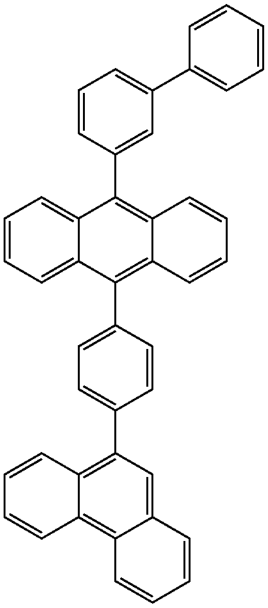
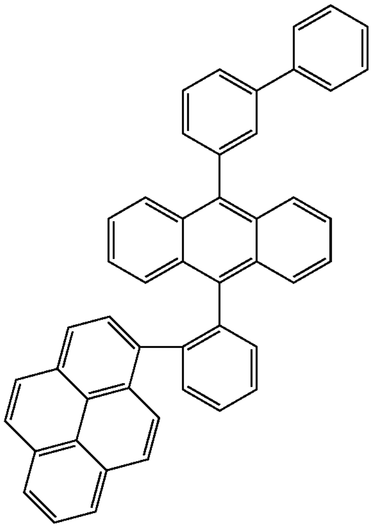
-continued
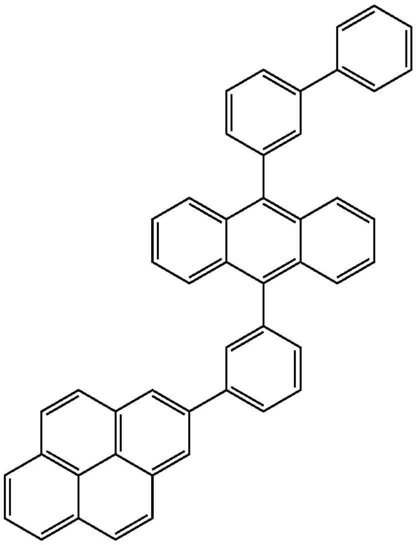
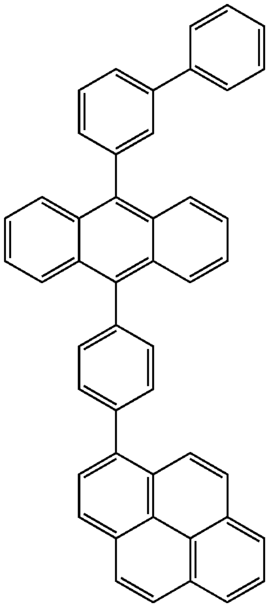
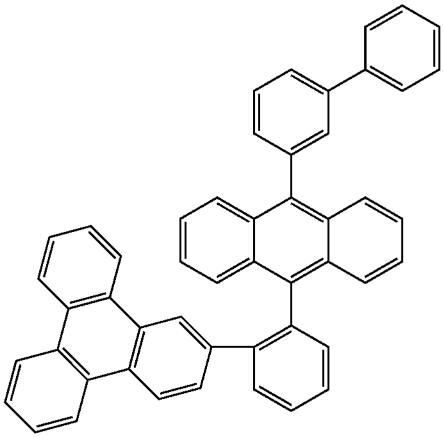

-continued
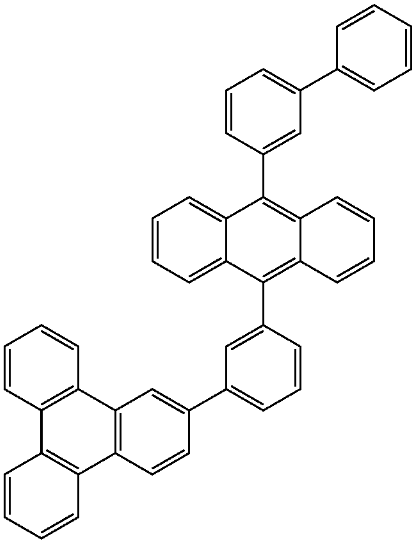
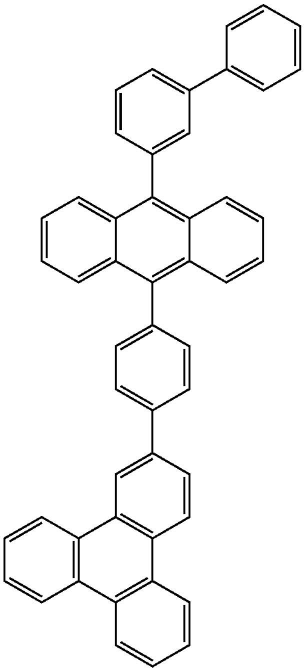
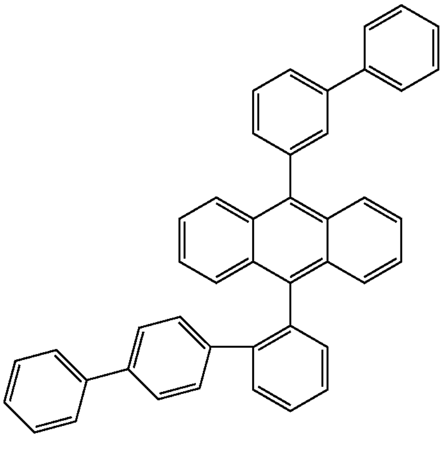
-continued
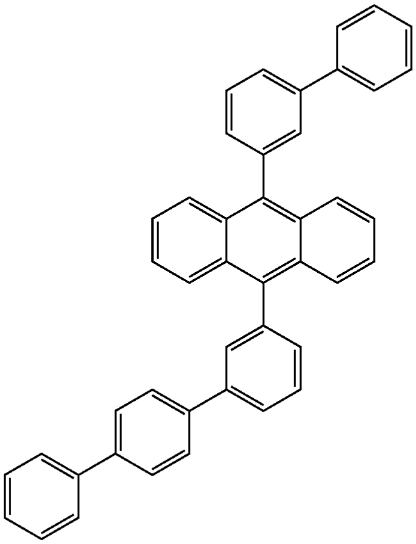
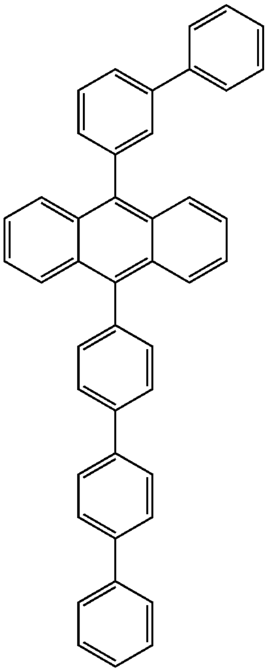
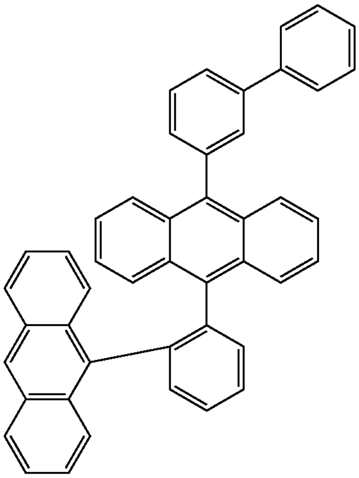

-continued
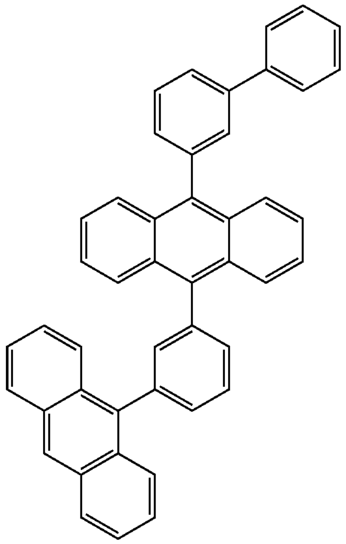
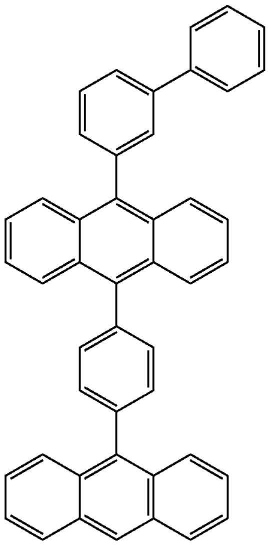
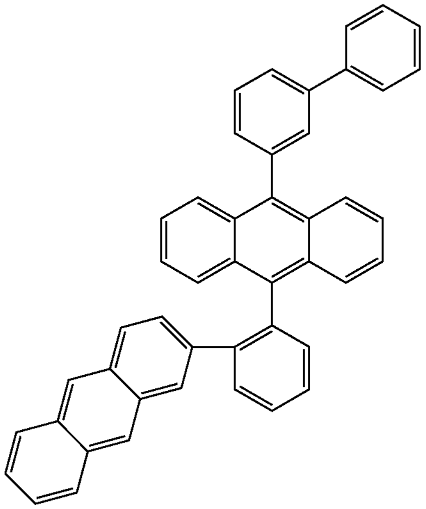
-continued
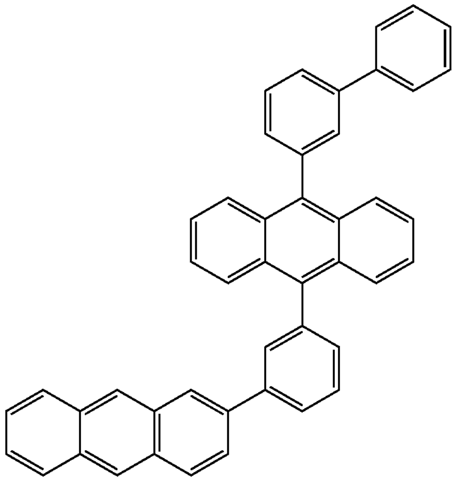
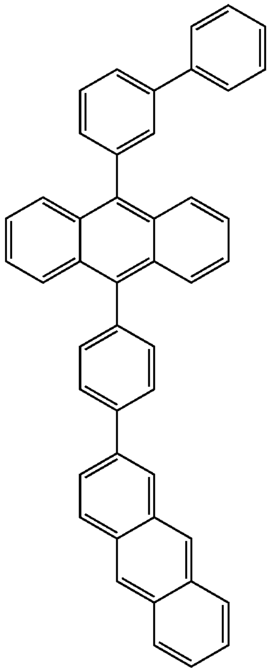
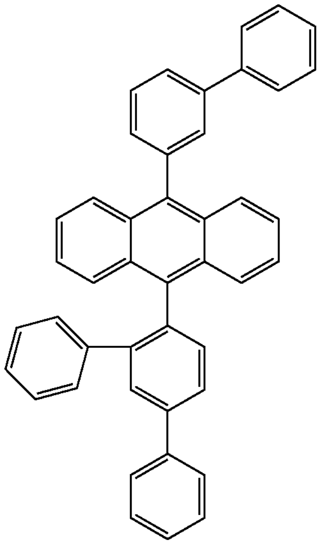

-continued
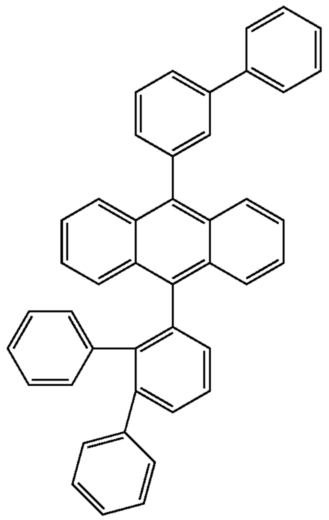
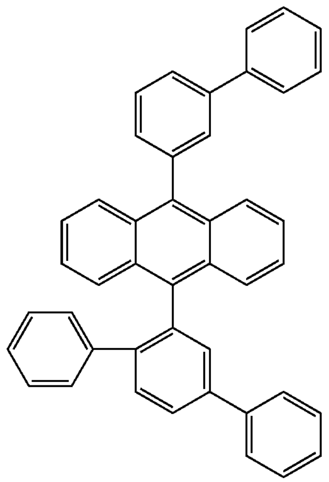
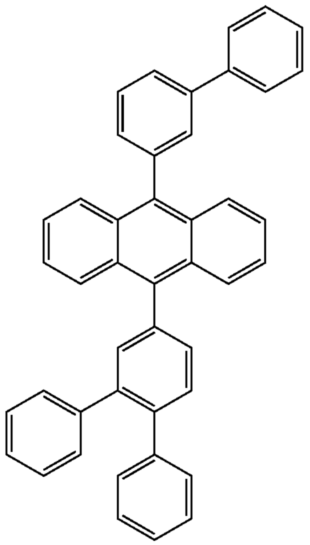
-continued
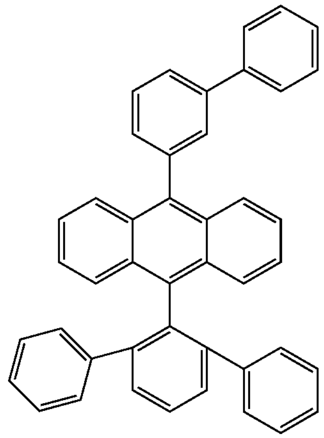
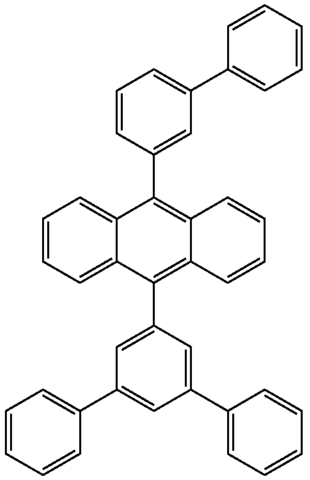
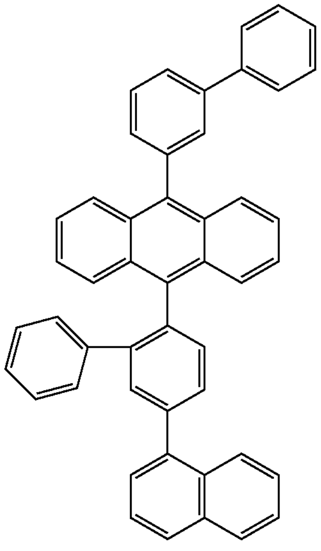

-continued
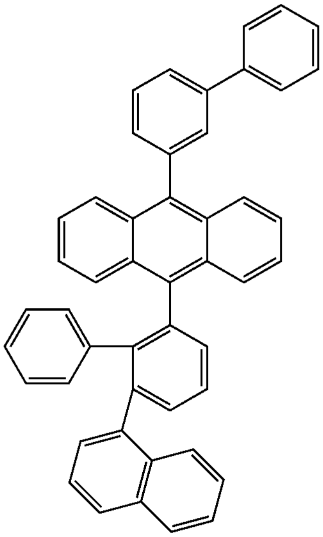
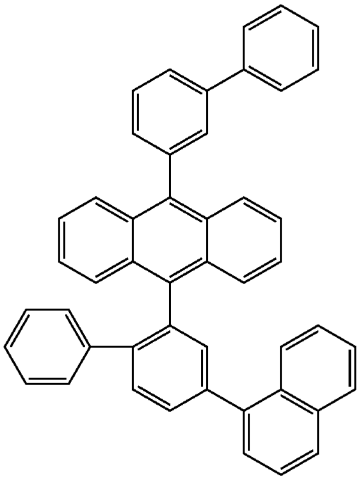
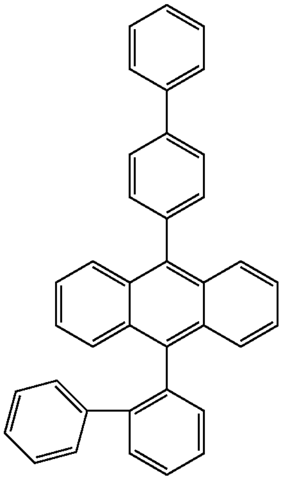
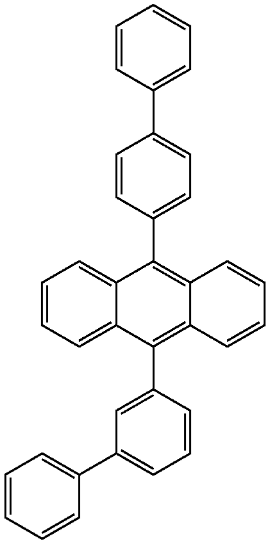
-continued
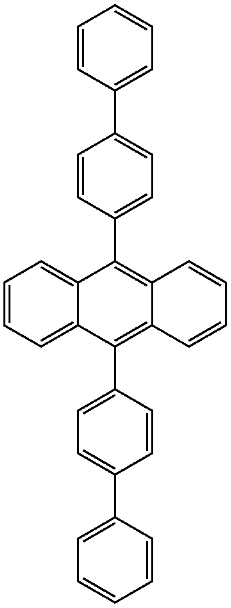
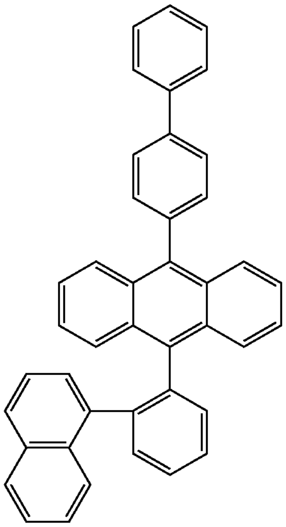
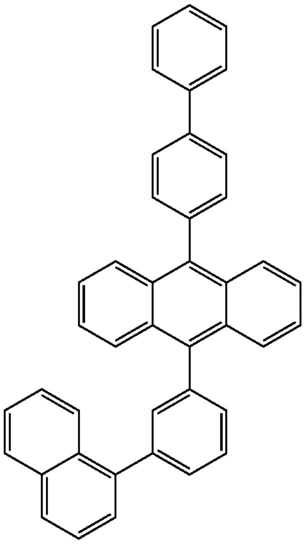
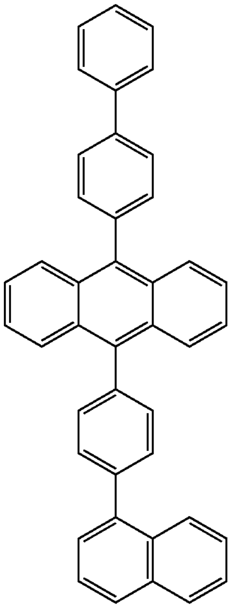

-continued
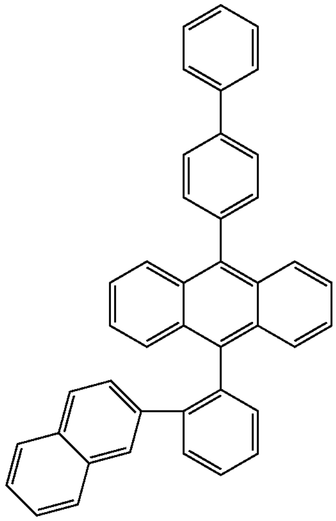
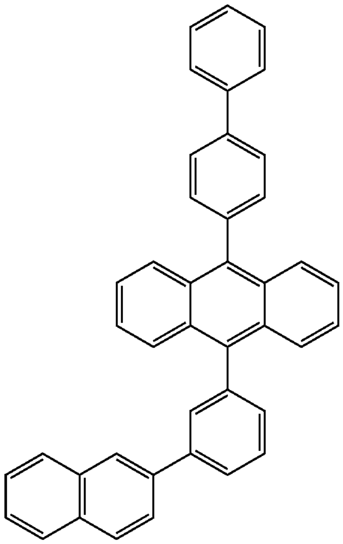
-continued
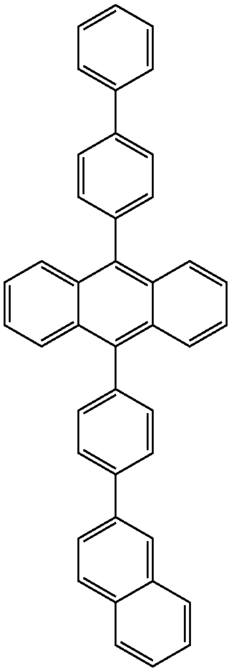
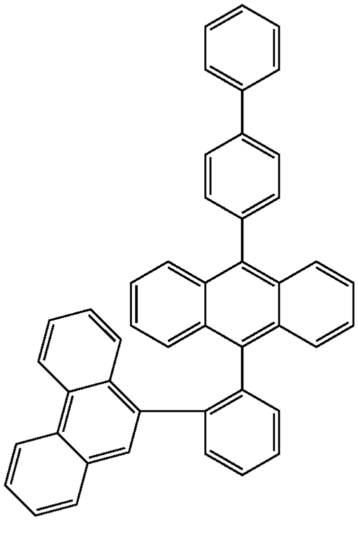

-continued
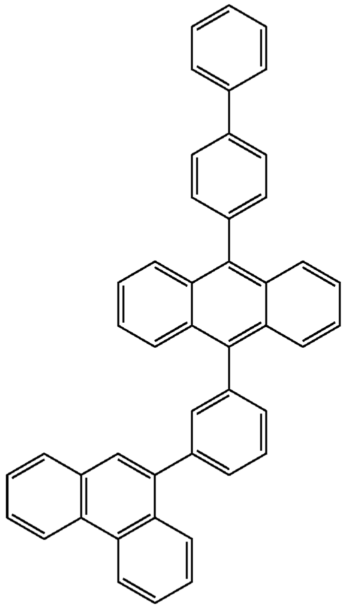
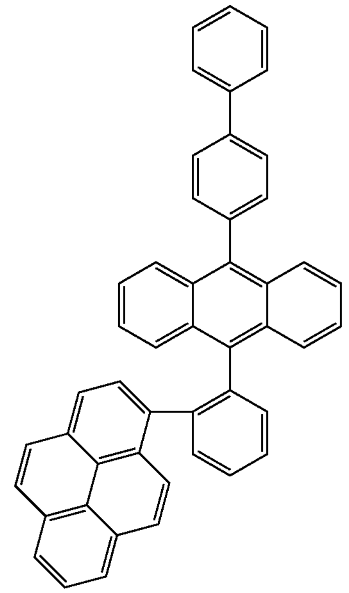
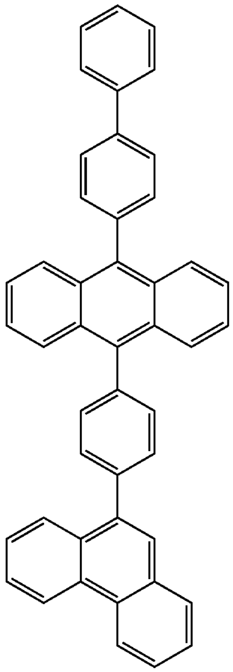
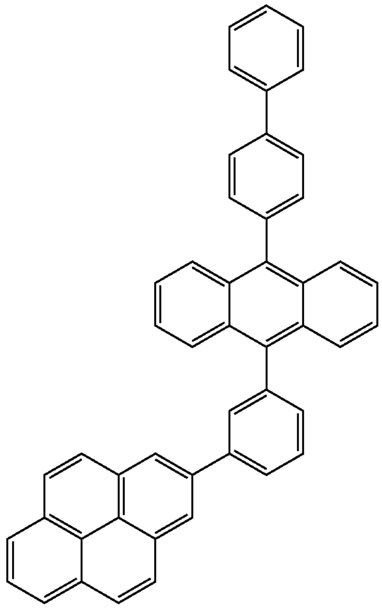

-continued
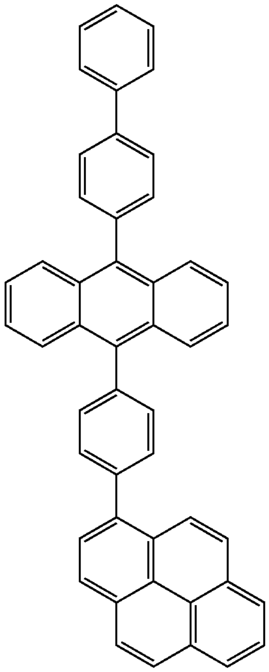
-continued
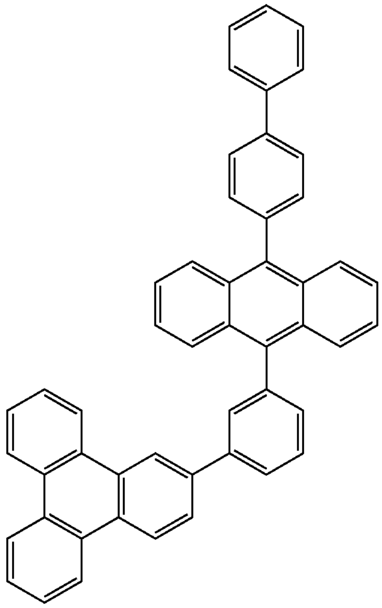
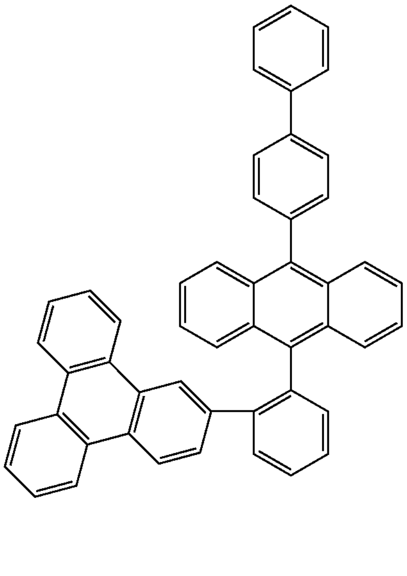
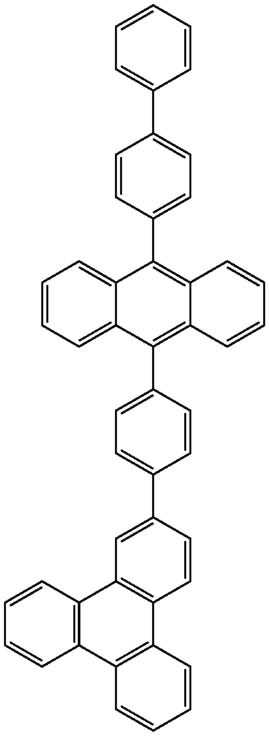

-continued
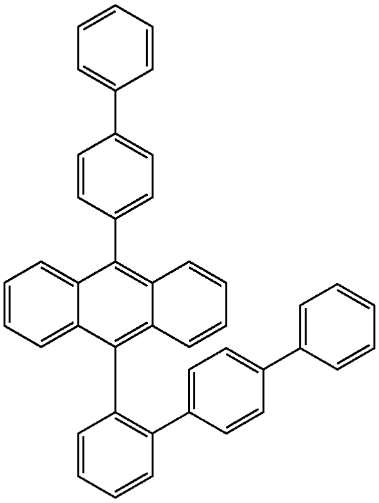
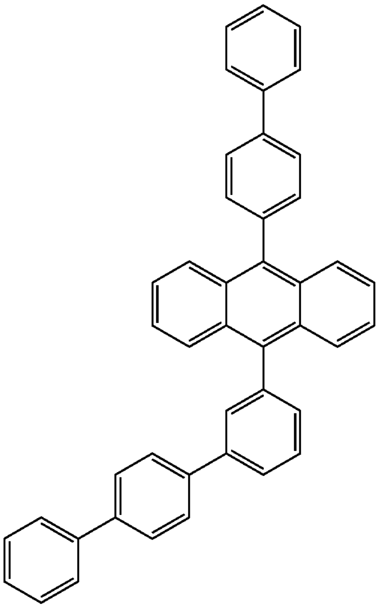
-continued
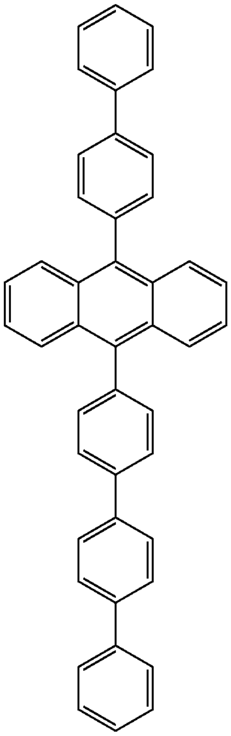
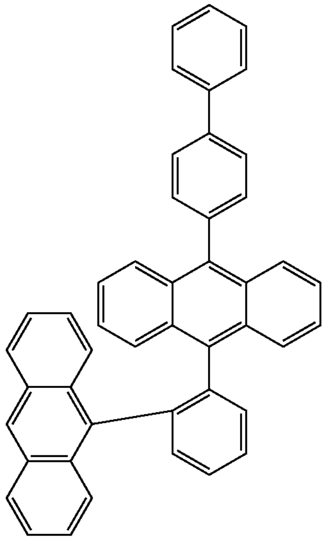
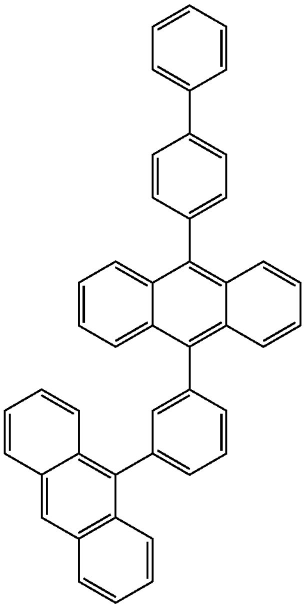
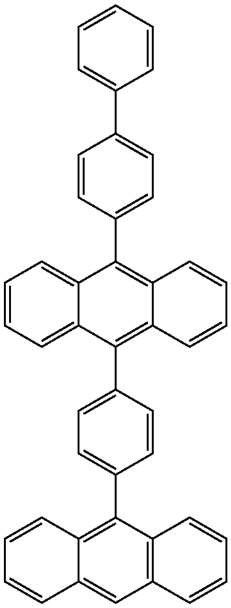

-continued
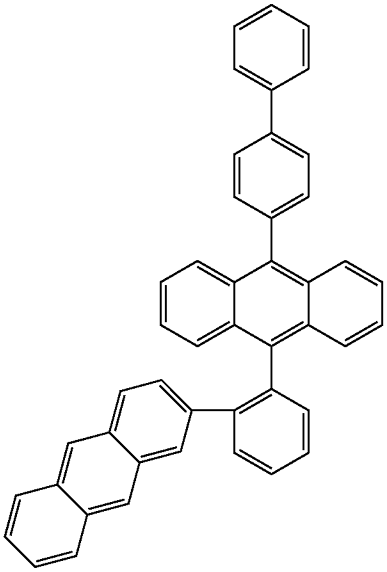
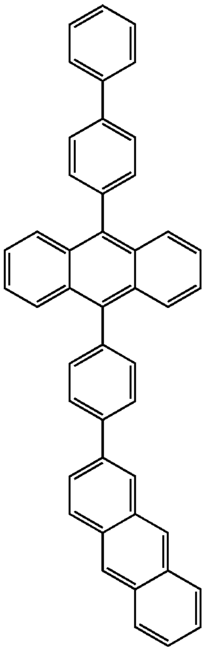
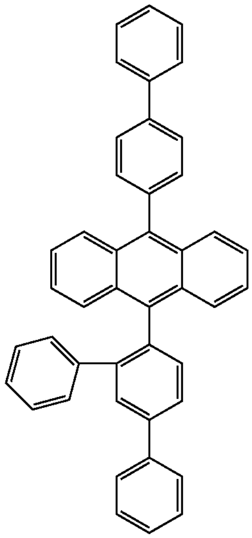
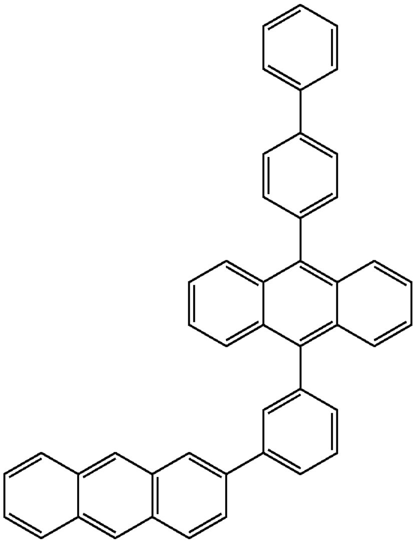
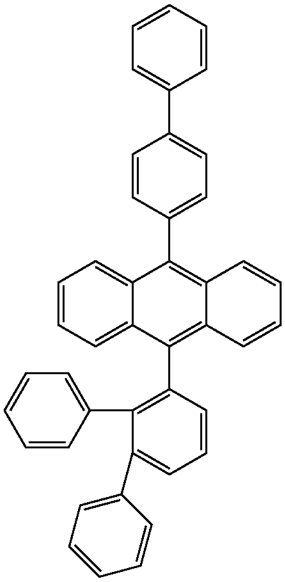

-continued
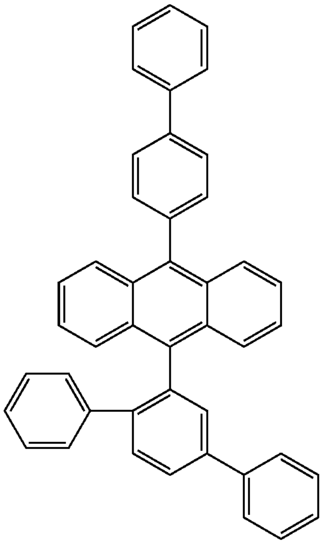
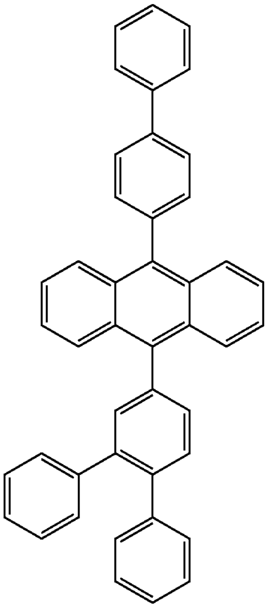
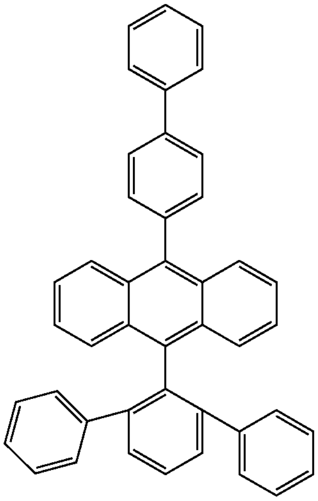
-continued
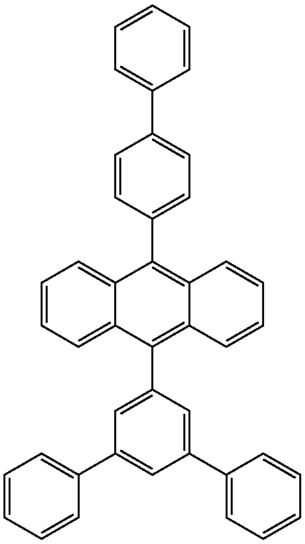
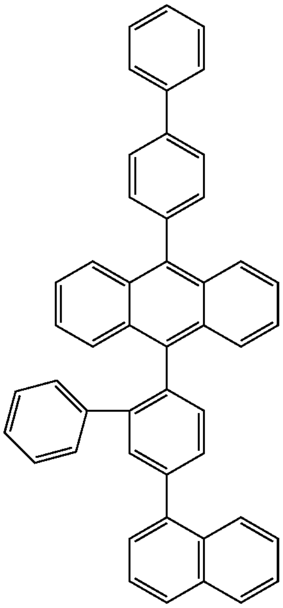

-continued
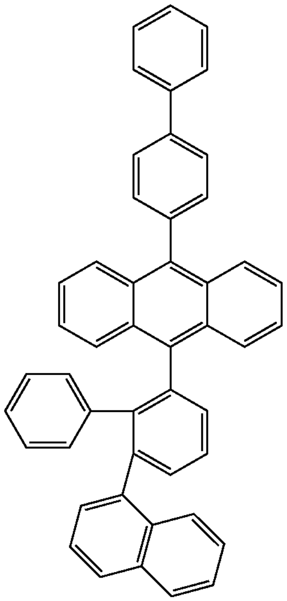
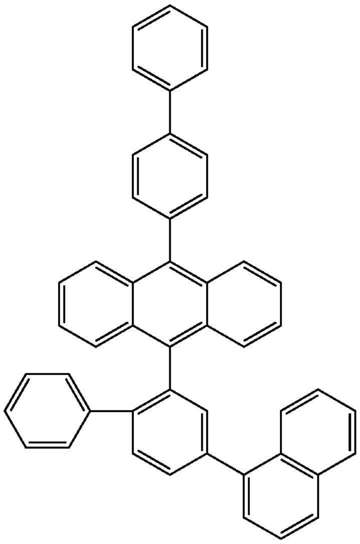
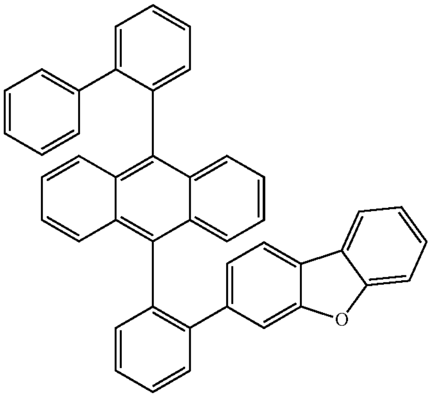
-continued
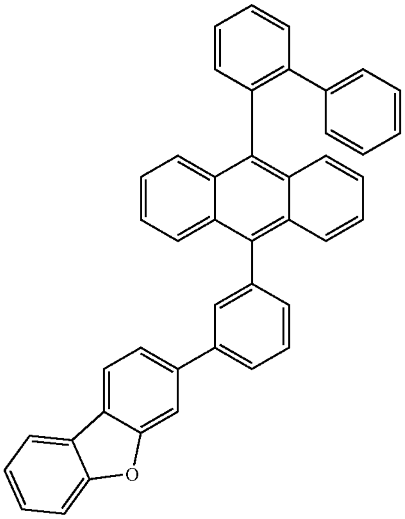
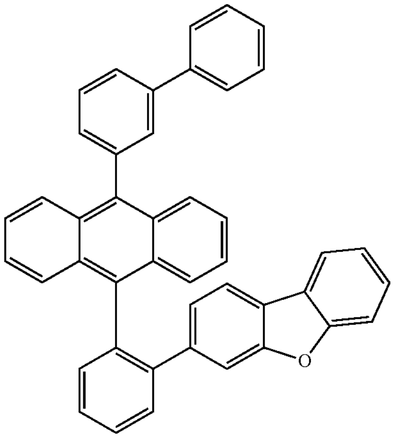
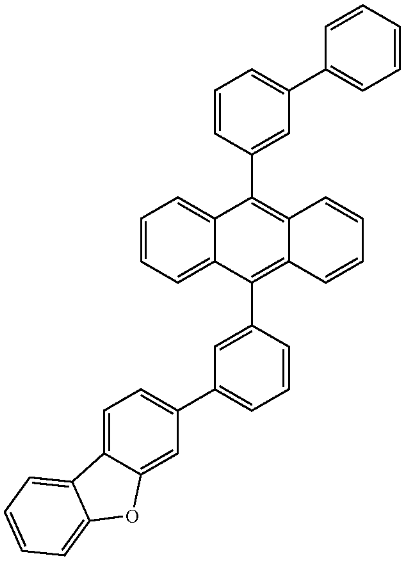

-continued
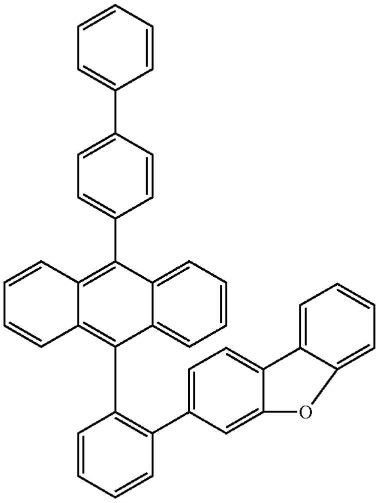
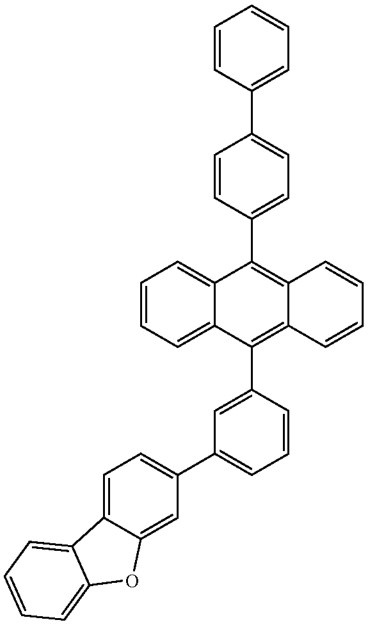
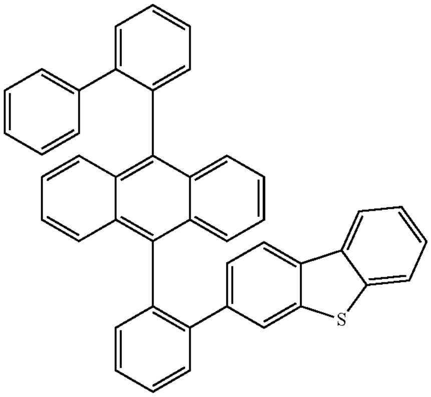
-continued
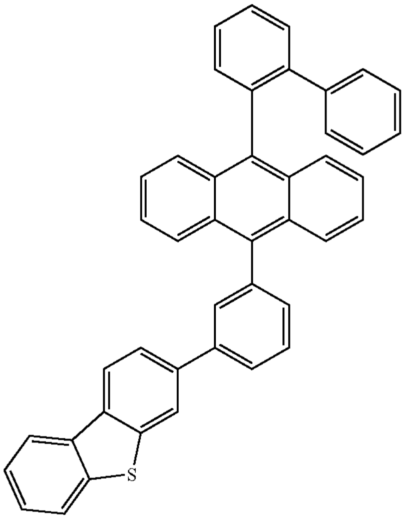
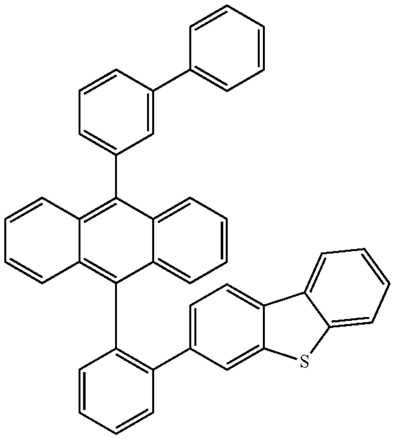
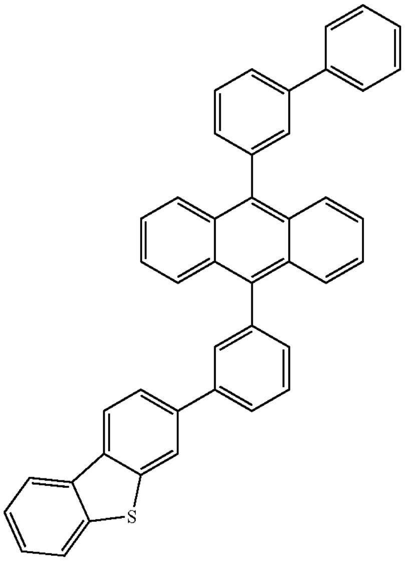

-continued
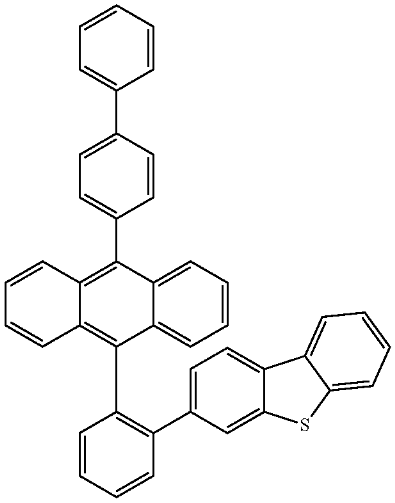
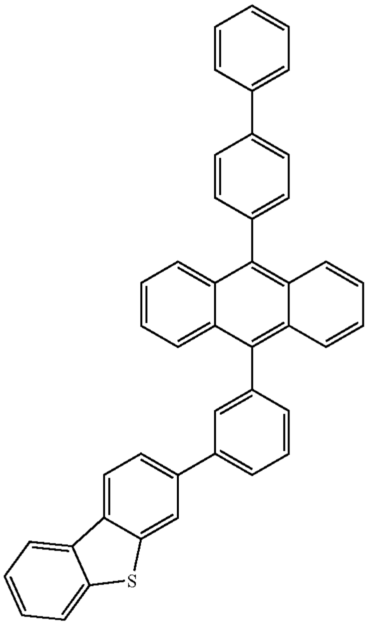
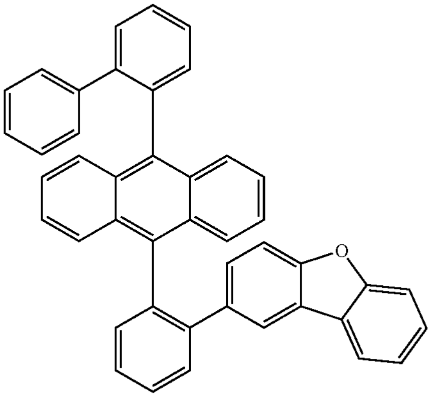
-continued
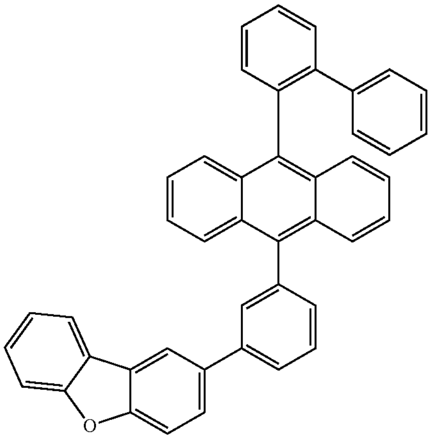
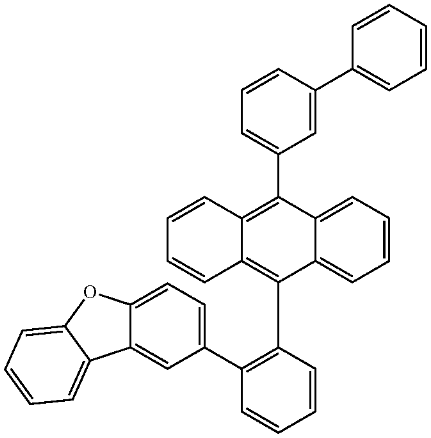
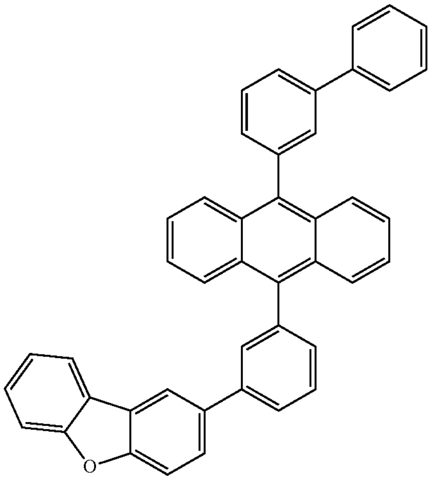

-continued
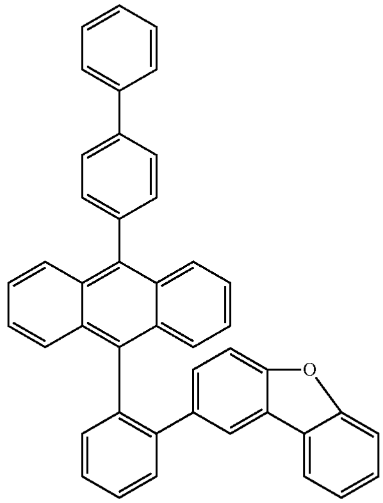
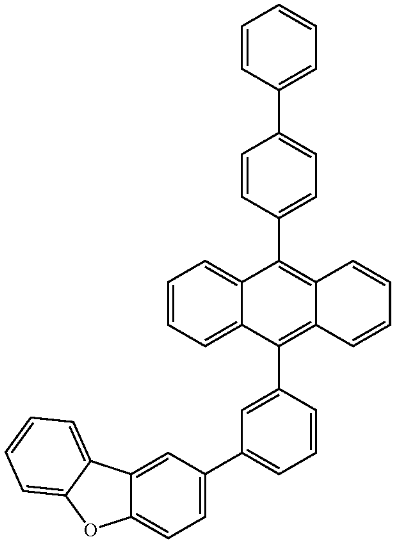
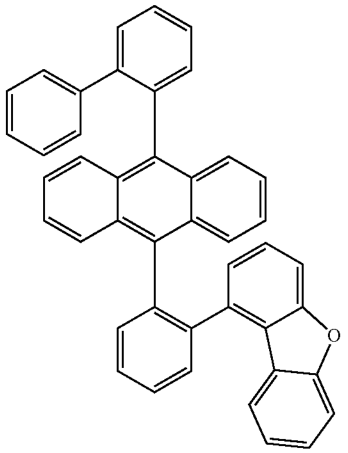
-continued
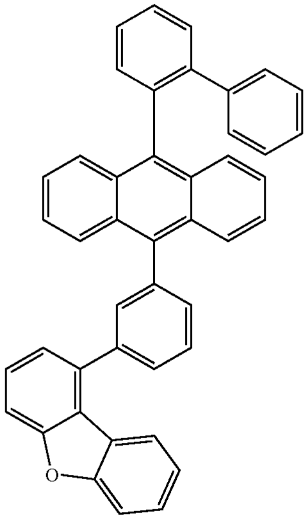
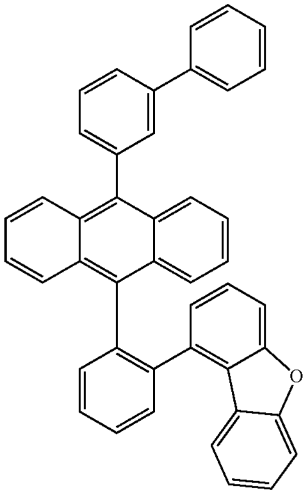
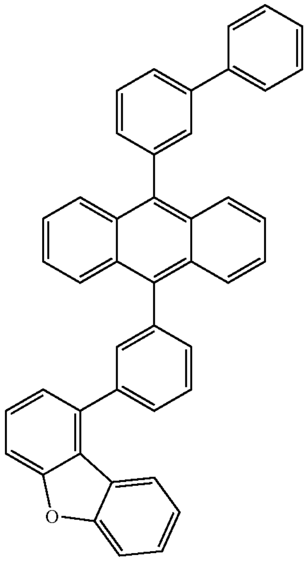

-continued
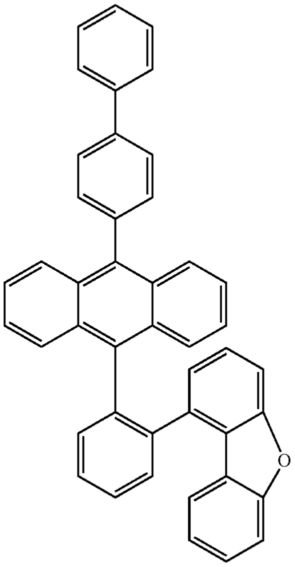
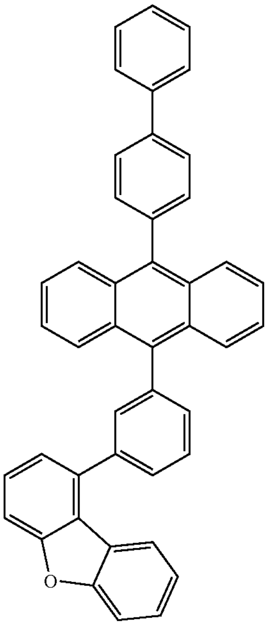
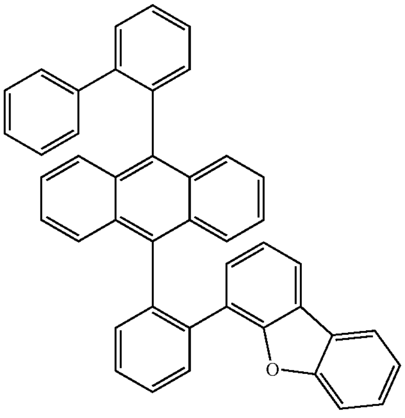
-continued
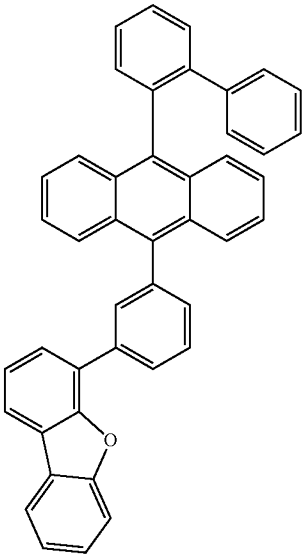
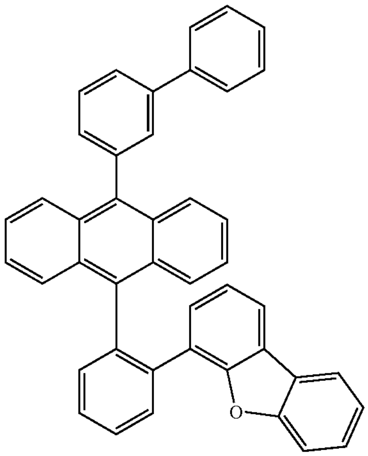
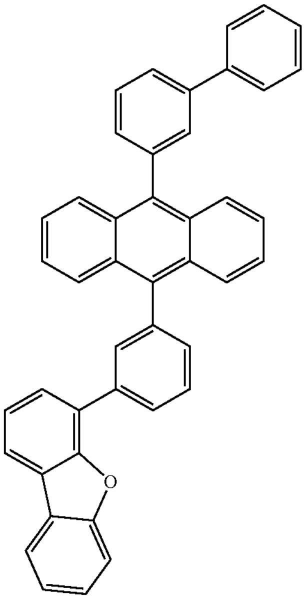

-continued
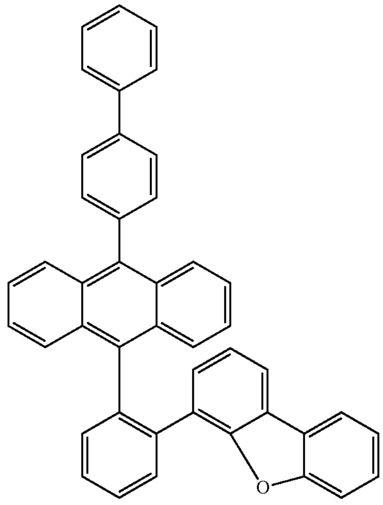
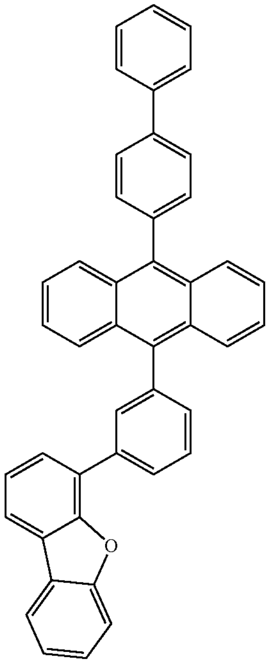
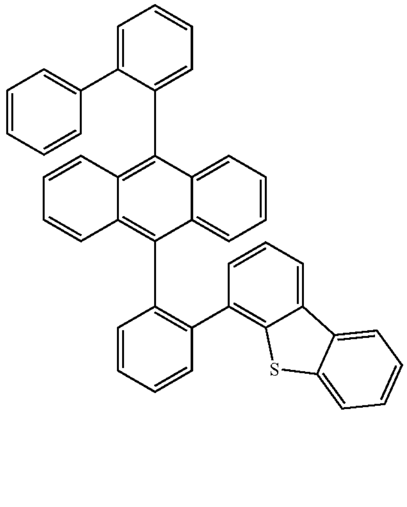
-continued
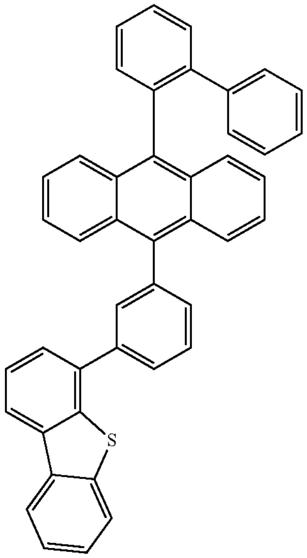
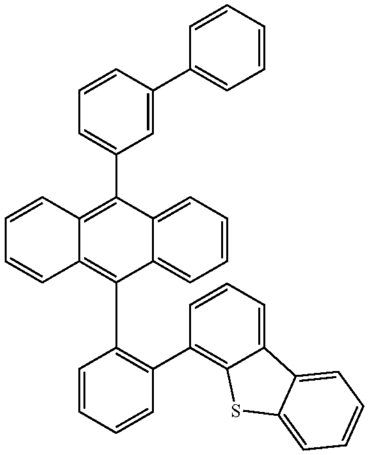
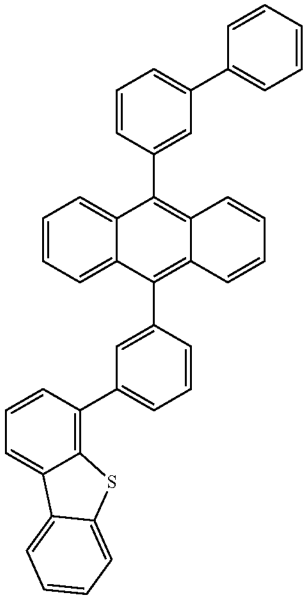

-continued
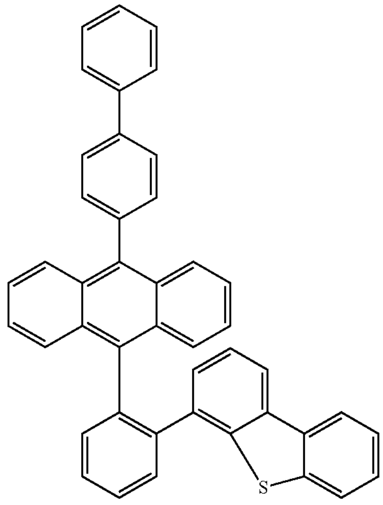
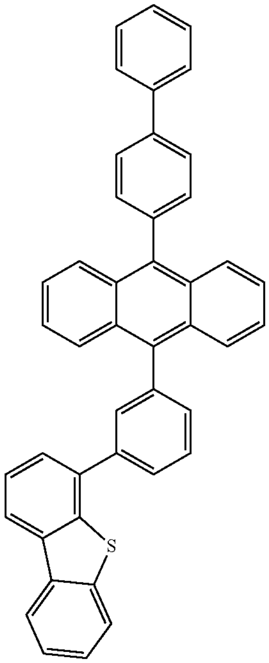
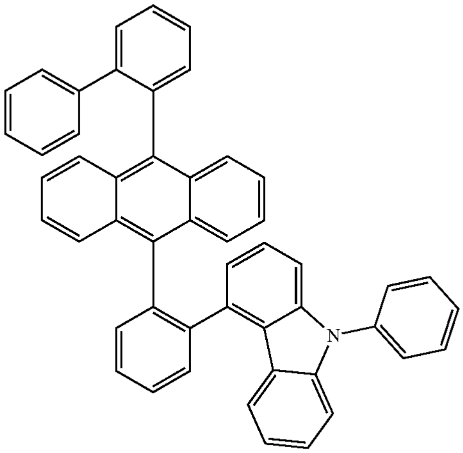
-continued
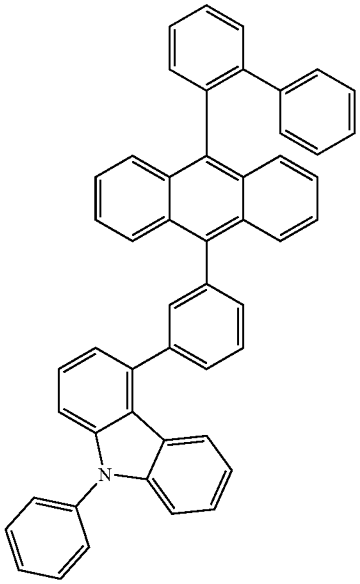
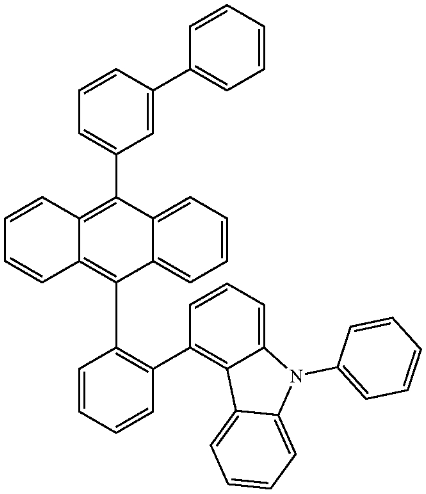
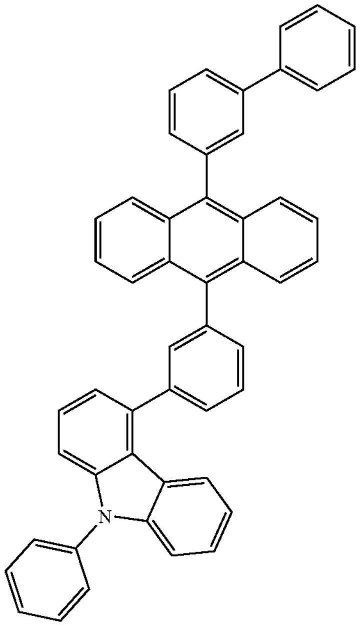

-continued
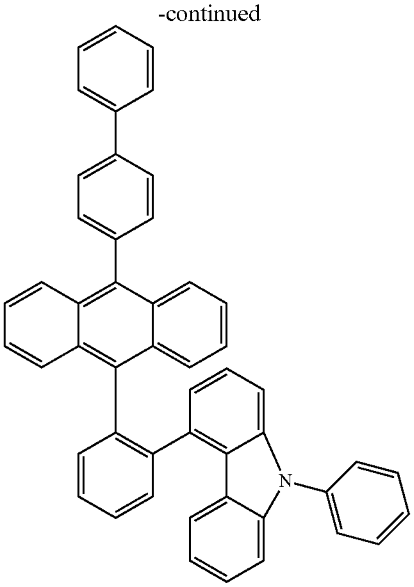
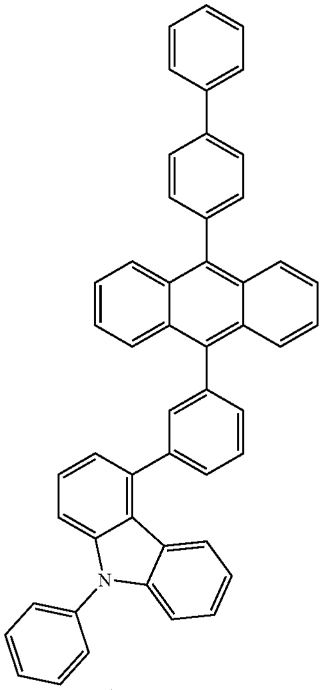
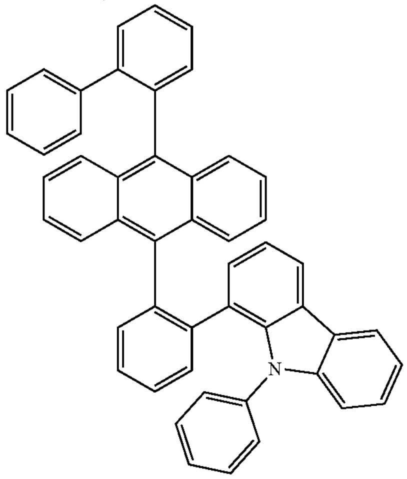
-continued
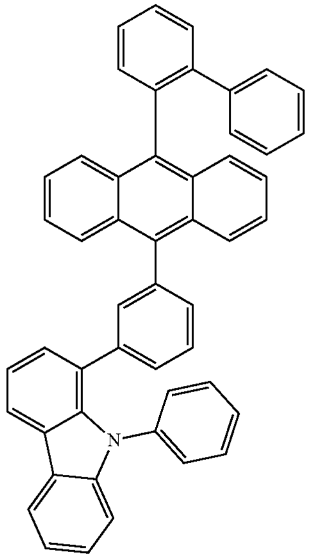
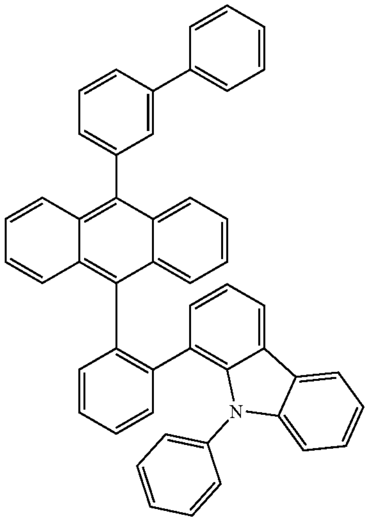
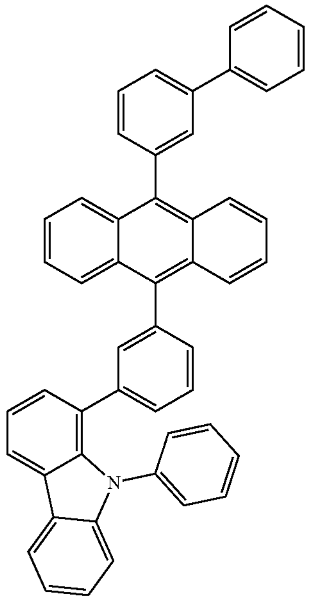

-continued
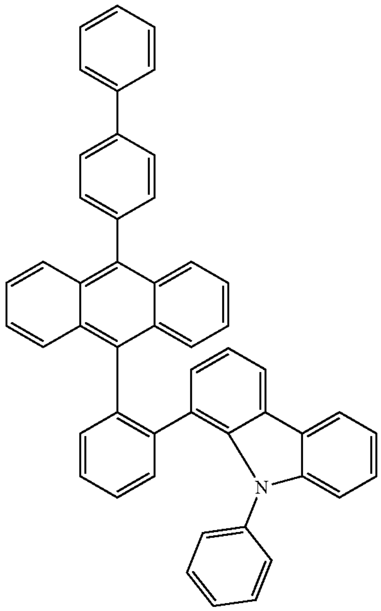
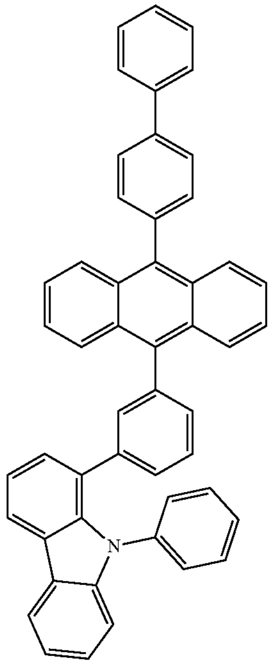
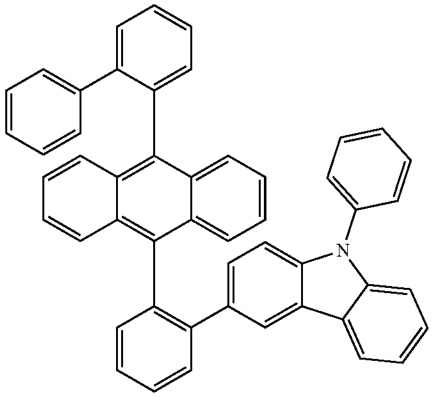
-continued
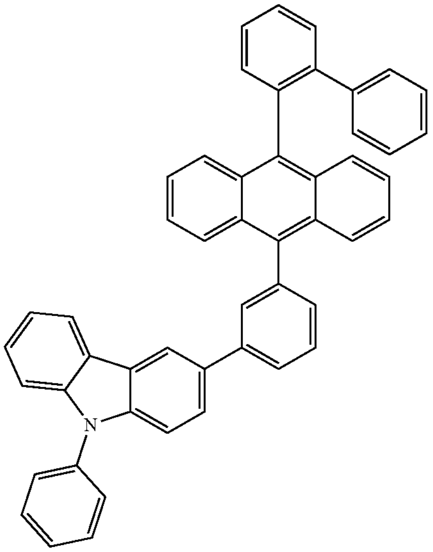
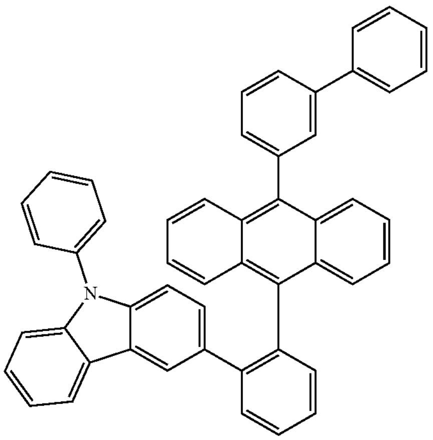
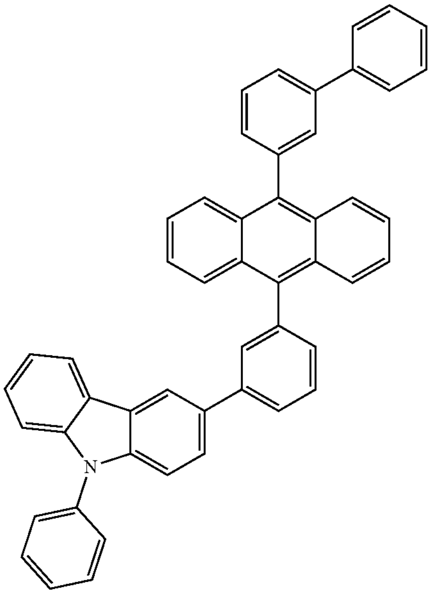

-continued
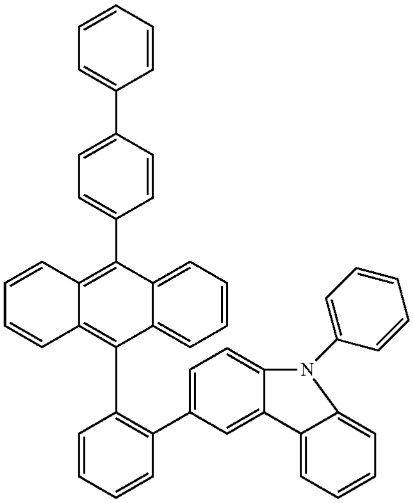
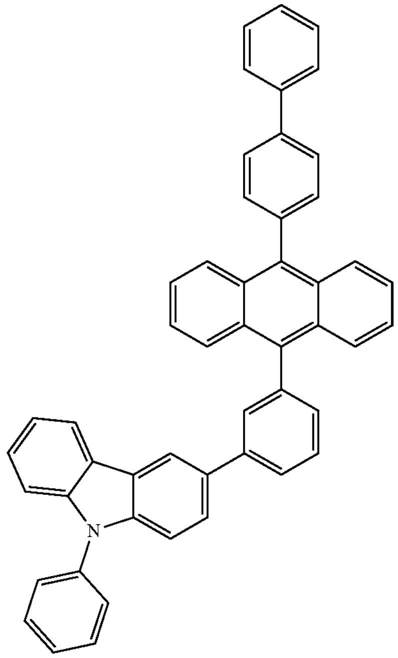
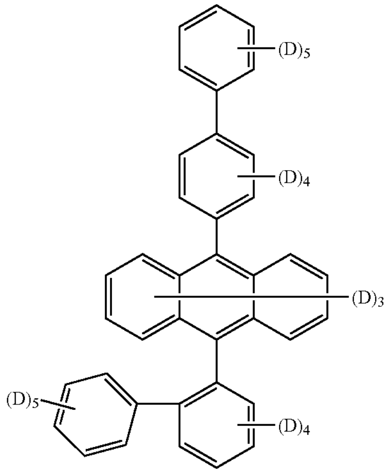
-continued
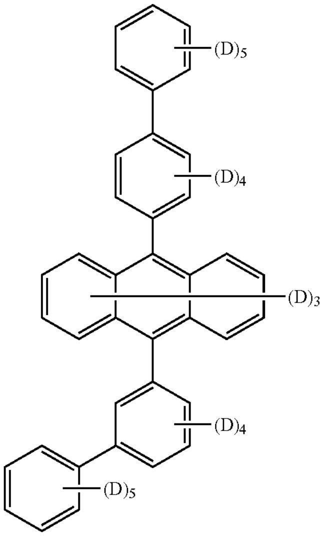
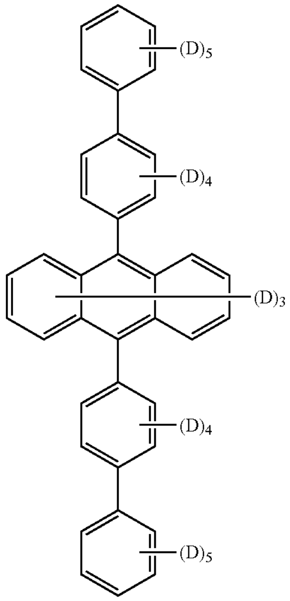
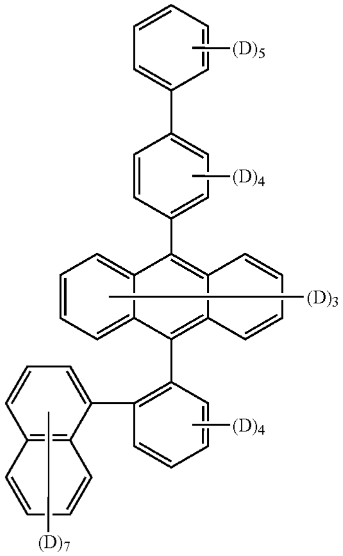

-continued
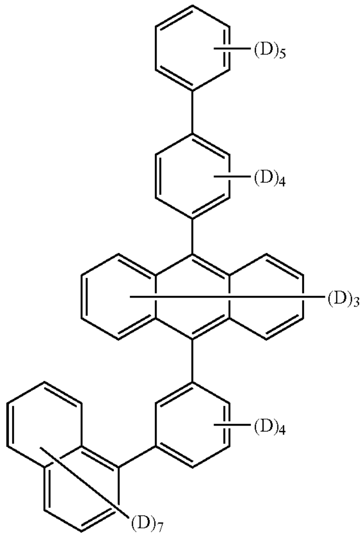
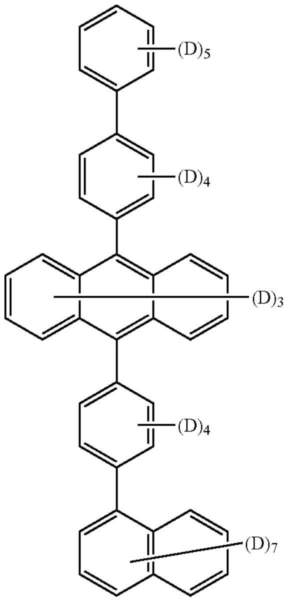
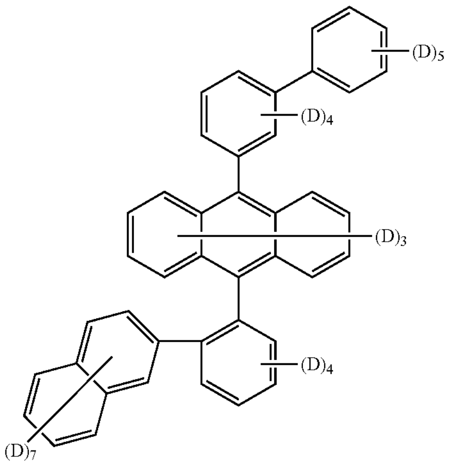
-continued
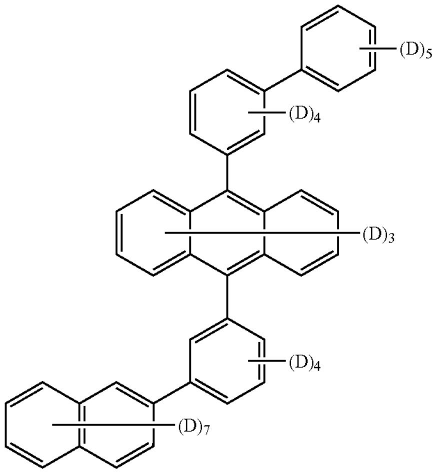
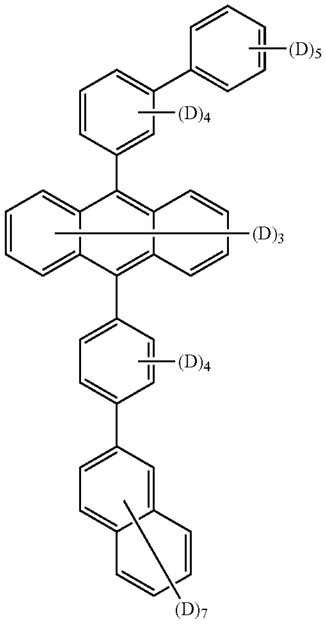
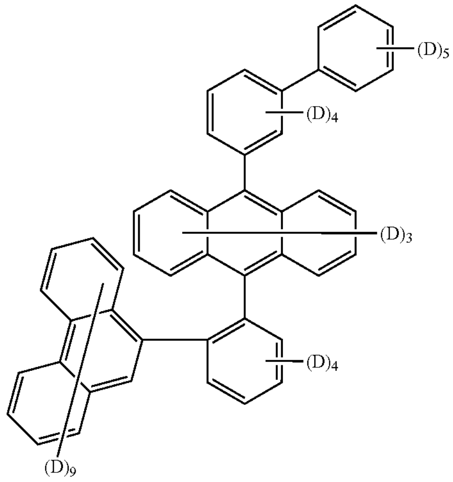

-continued
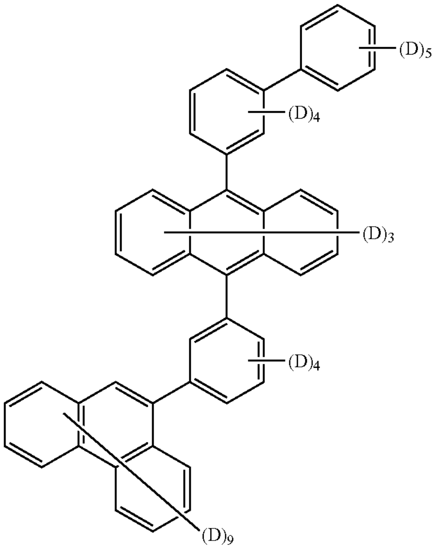
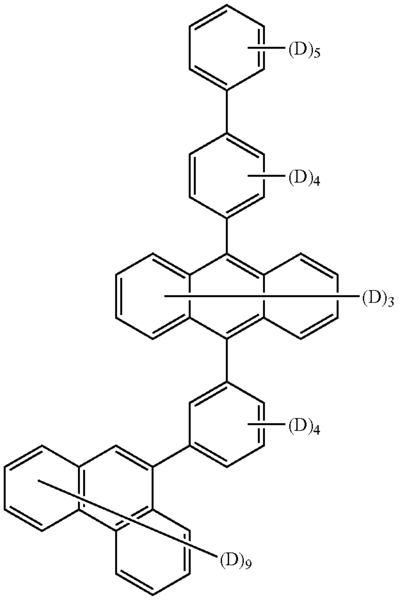
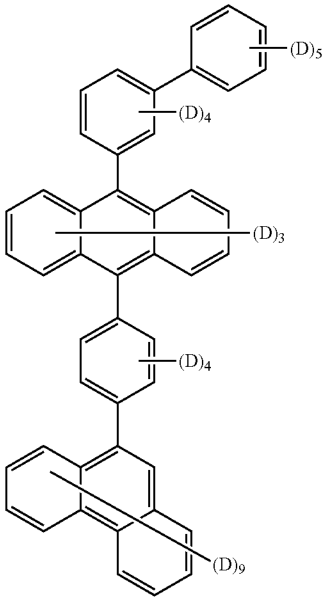
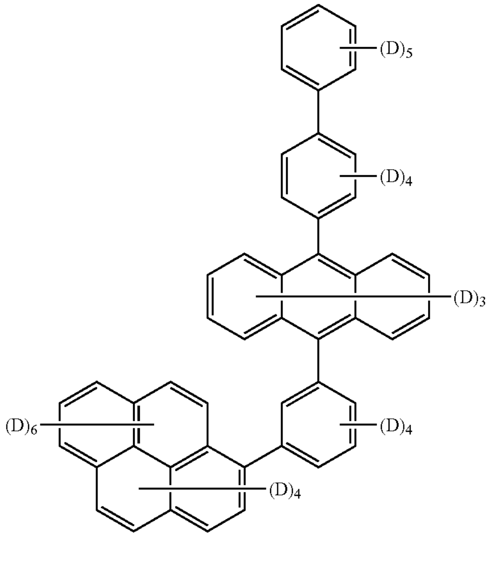

-continued
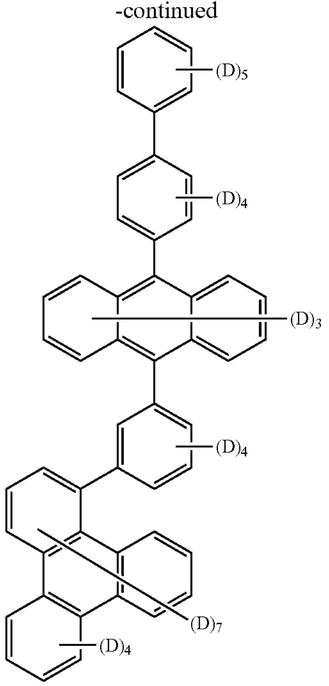
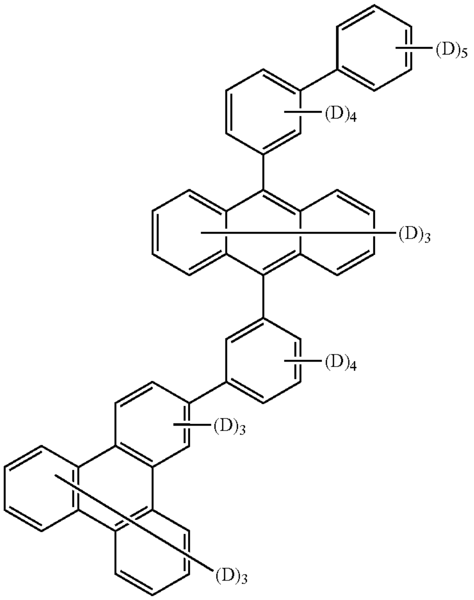
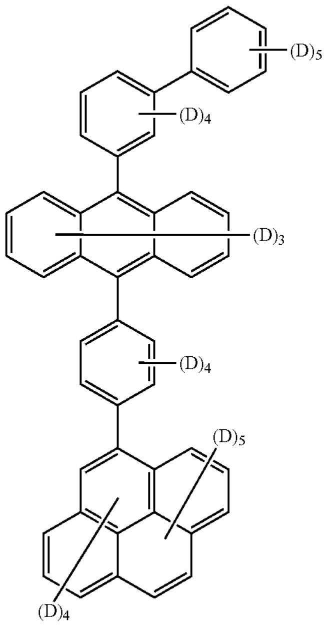
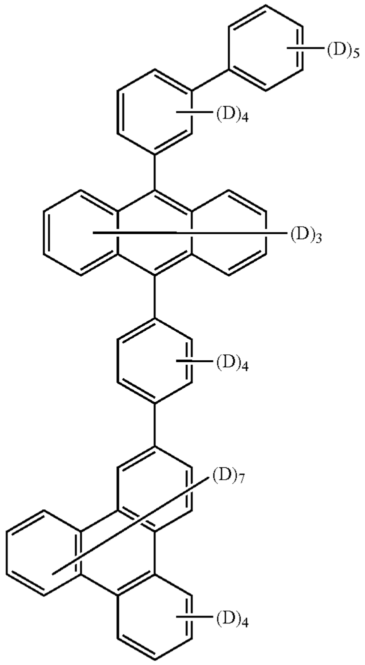

-continued
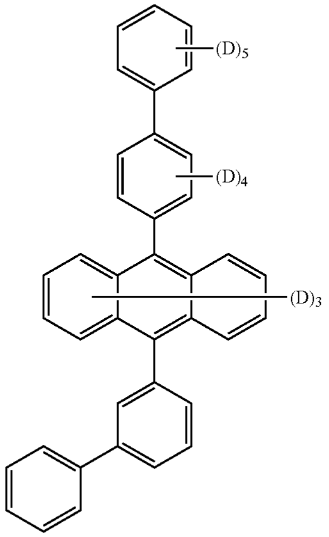
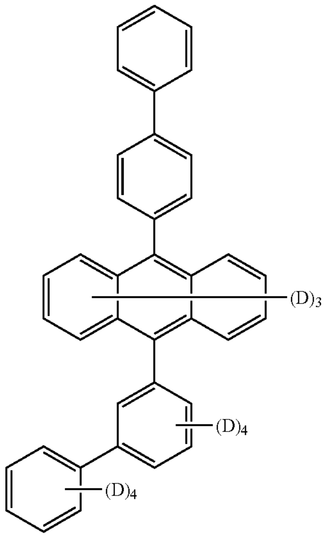
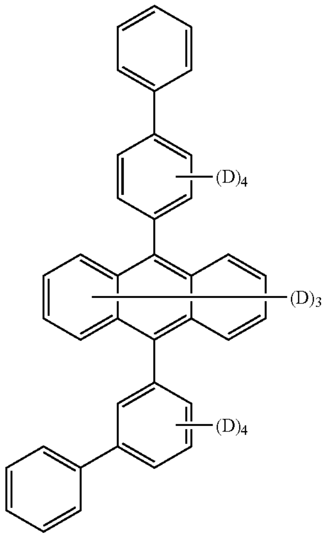
-continued
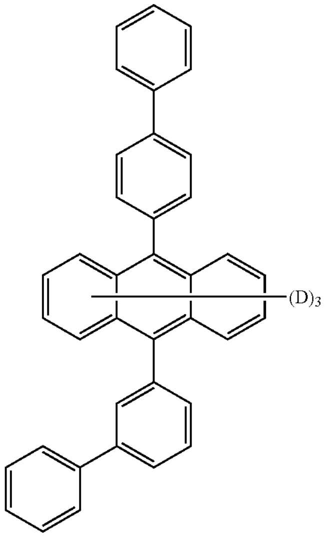
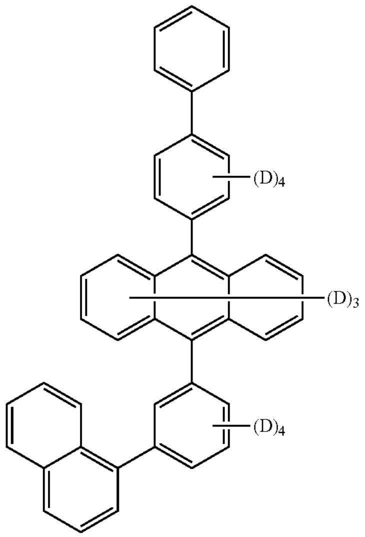
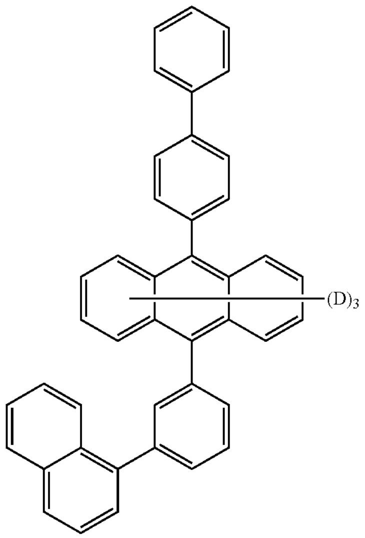

-continued
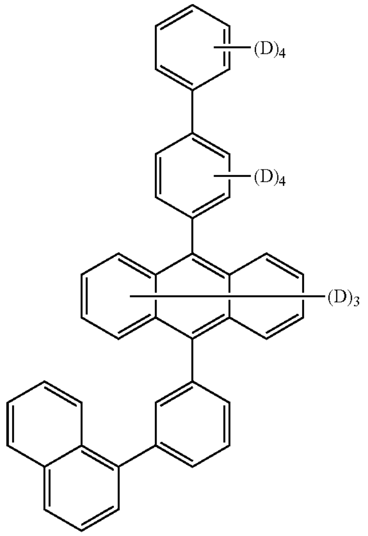
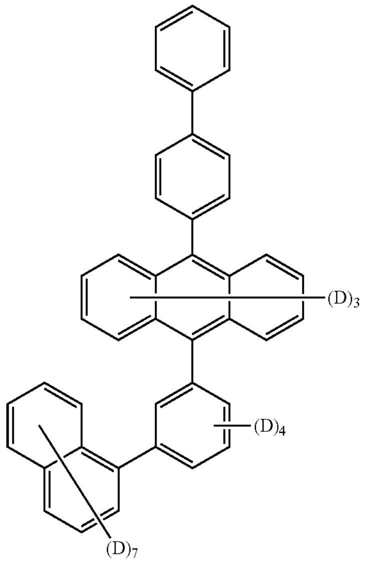
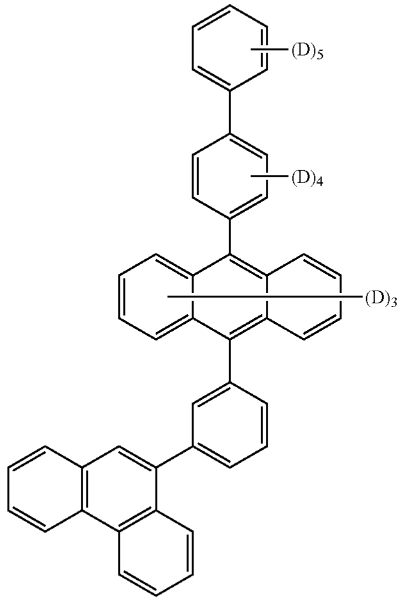
-continued
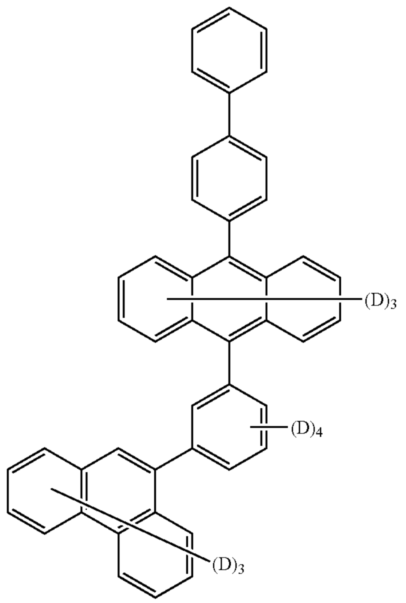
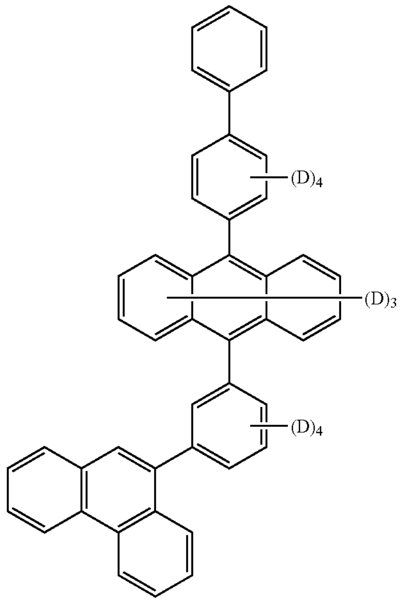

-continued
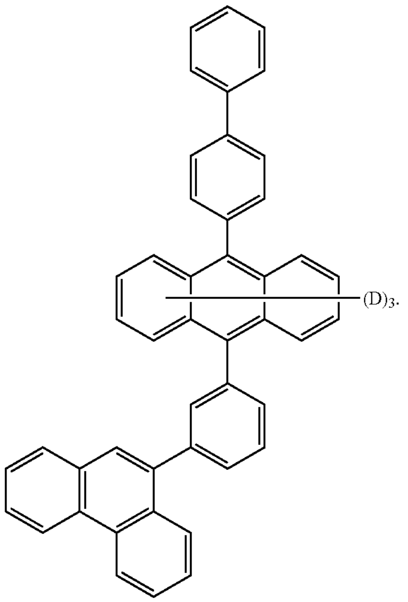
According to an exemplary embodiment of the present application, the compound of Formula 2 is selected from among the following compounds:
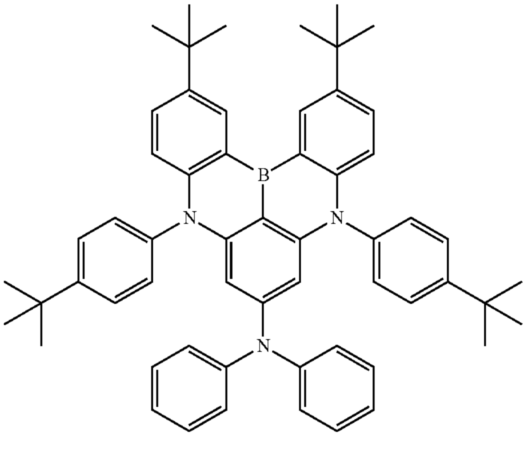
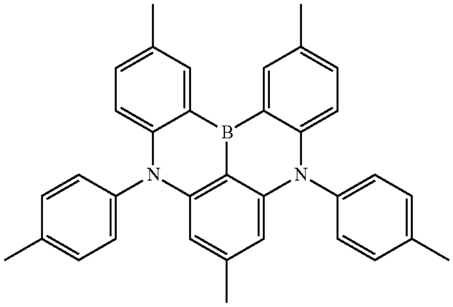
-continued
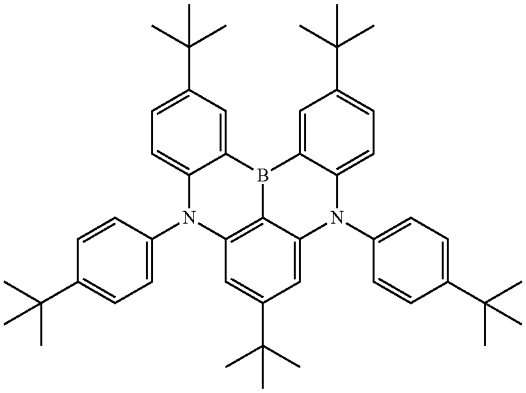
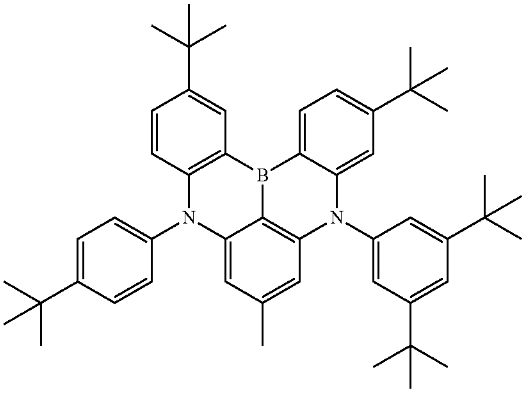
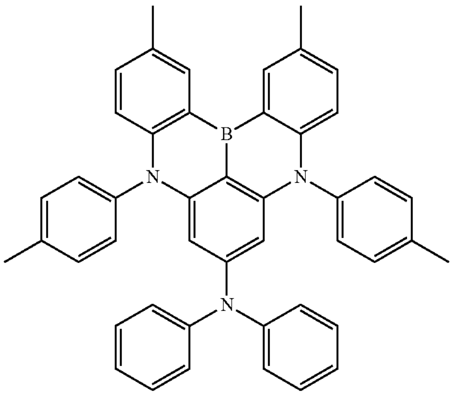
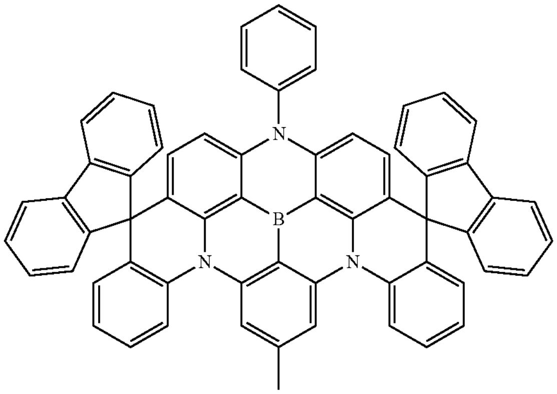

-continued
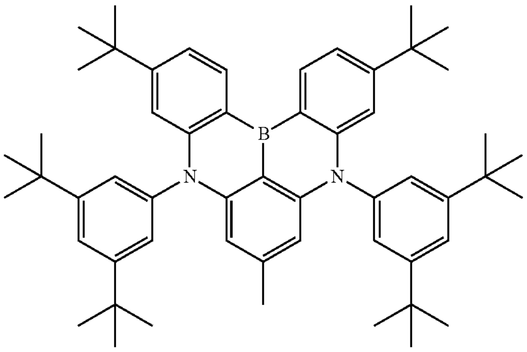
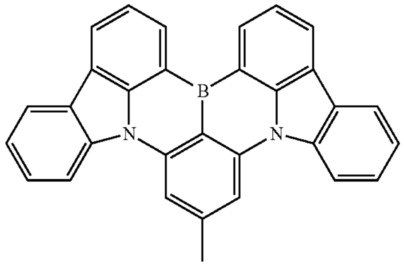
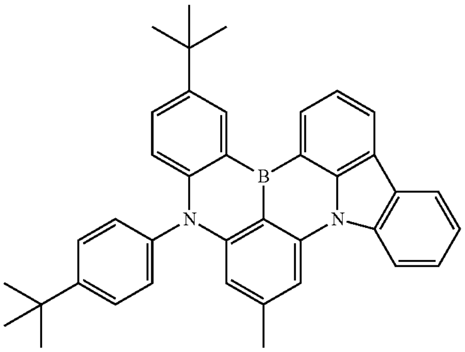
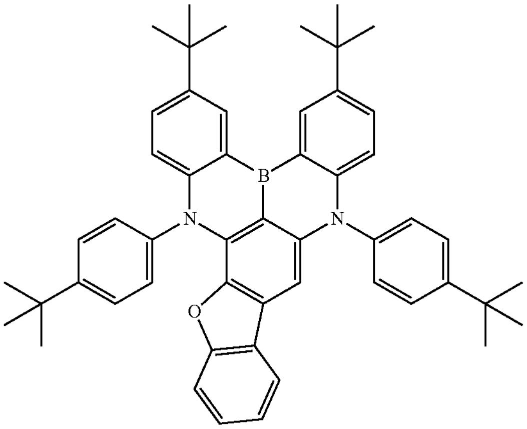
-continued
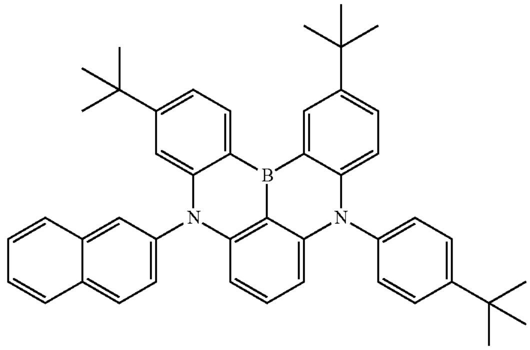
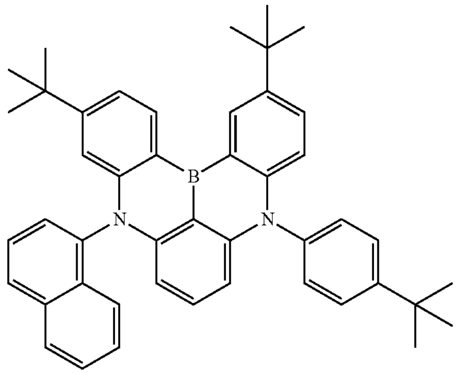
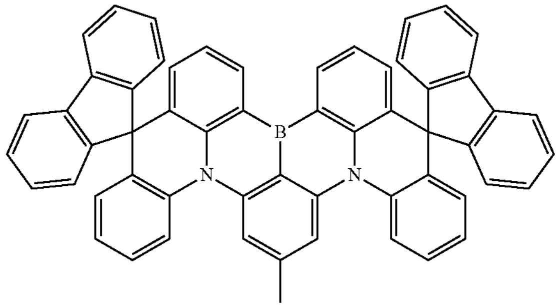
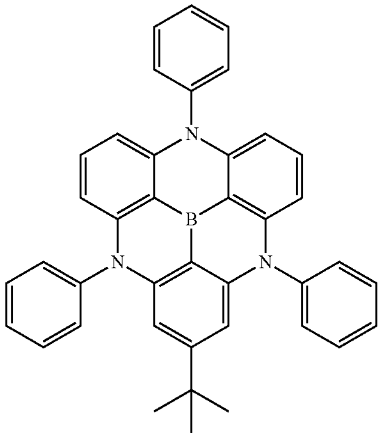

-continued
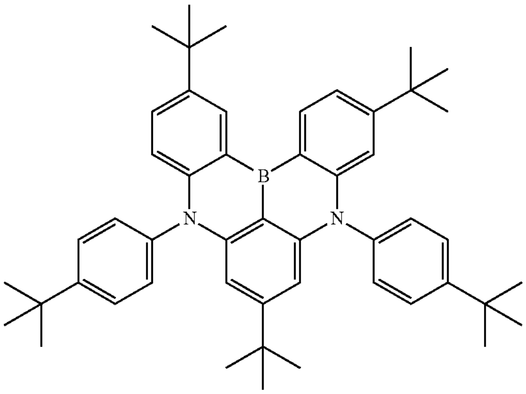
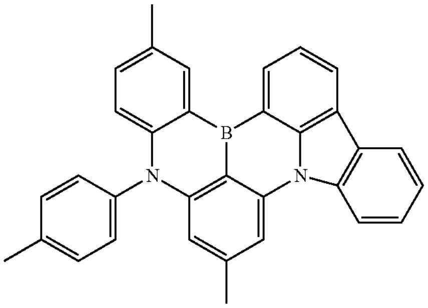
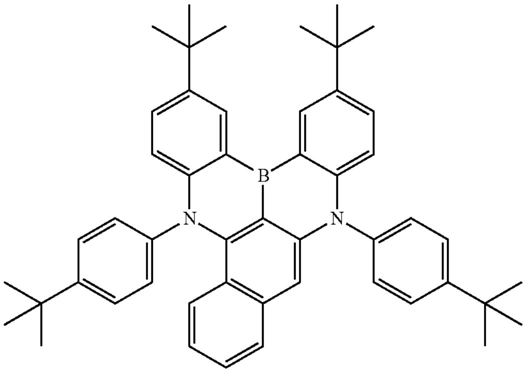
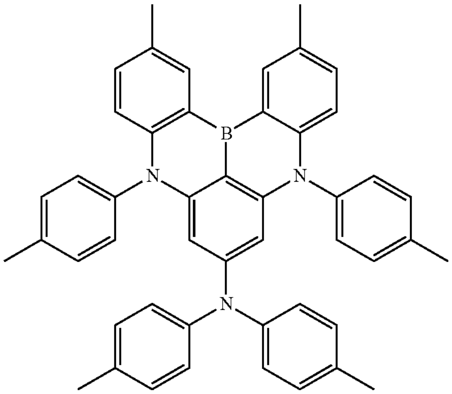
-continued
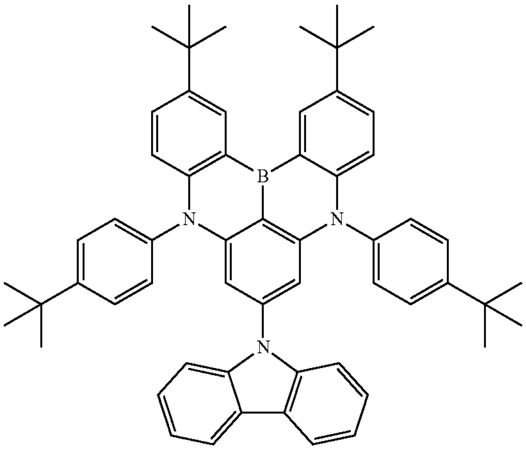
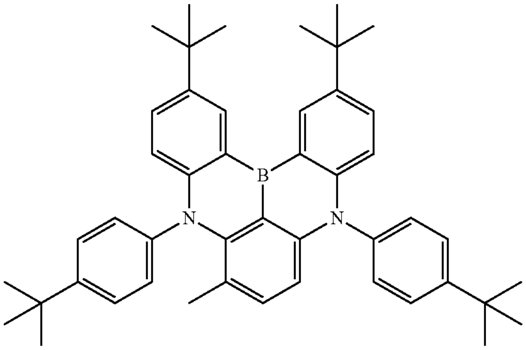
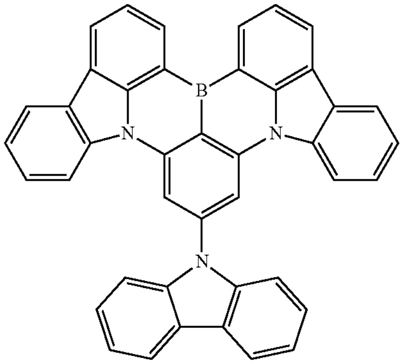
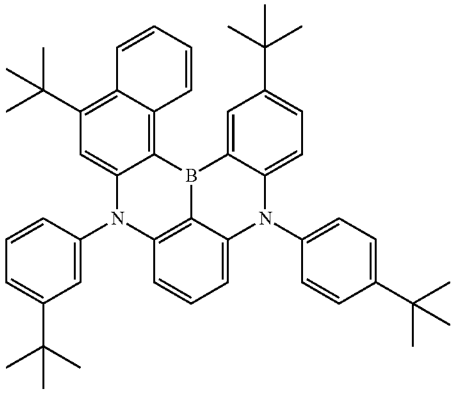

-continued

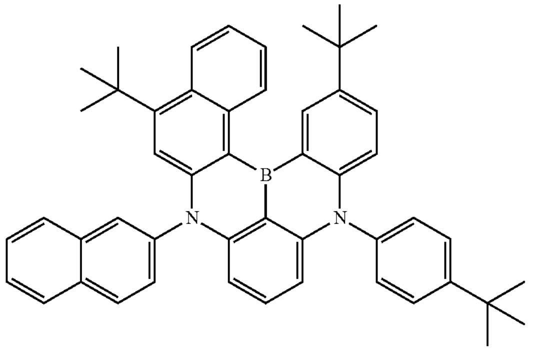

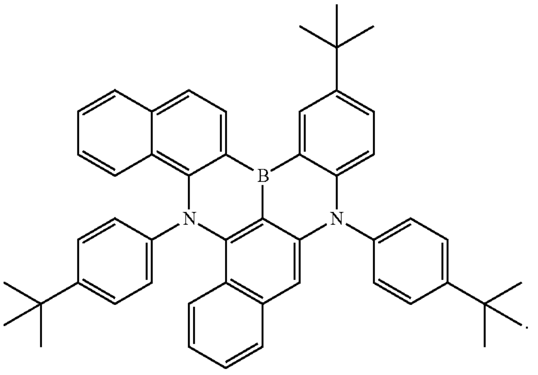

According to an exemplary embodiment of the present application, the organic material layer includes Formulae 1 and 2, and Formulae 1 and 2 are included at a weight ratio of 90:10 to 99:1 (Formula 1:Formula 2). Preferably, Formulae 1 and 2 are included at a weight ratio of 99:1 to 95:5.

The core structure of Formula 1 according to an exemplary embodiment of the present specification can be prepared as in the following Reaction Scheme 1, substituents can be bonded by methods known in the art, and the type, position, or number of substituents can be changed according to the technology known in the art.

<Reaction Scheme 1>

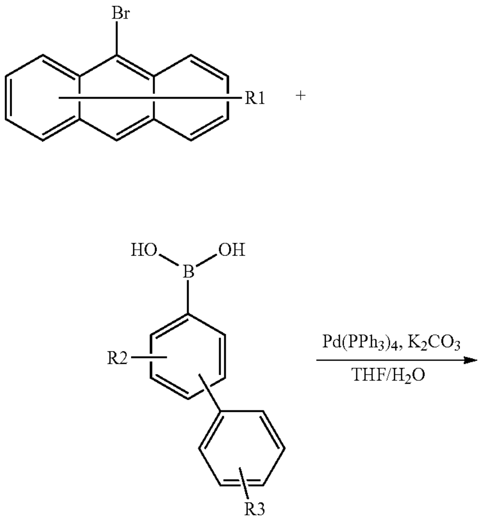

-continued

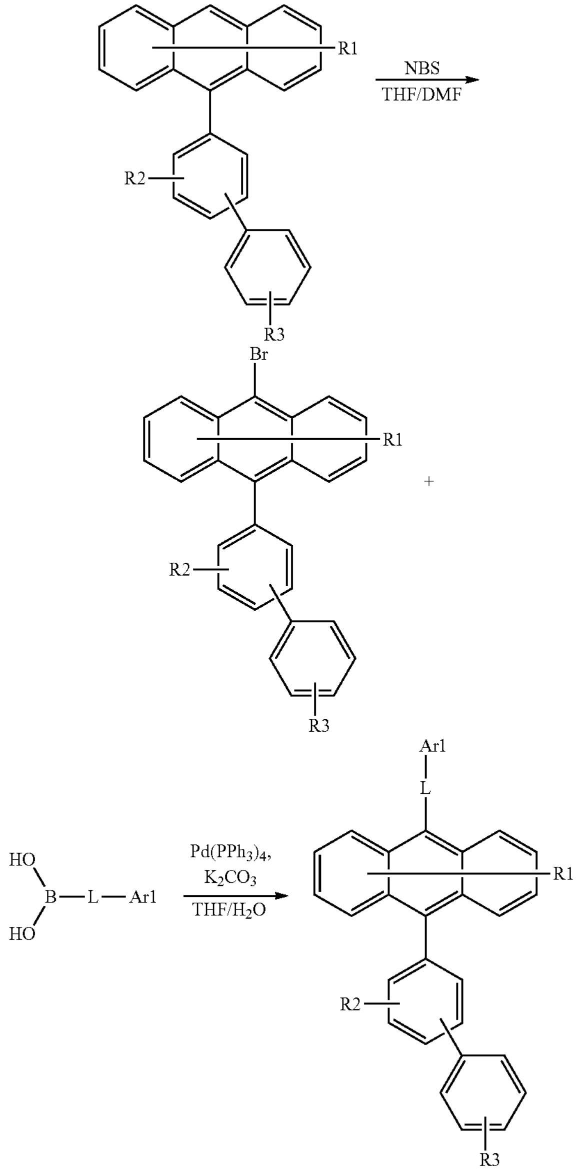

In Reaction Scheme 1, the definitions of R1 to R3, L, and Ar1 are the same as those defined in the above-described Formula 1.

The core structure of Formula 2 according to an exemplary embodiment of the present specification can be prepared as in the following Reaction Formula 2, substituents can be bonded by methods known in the art, and the type, position, or number of substituents can be changed according to the technology known in the art.

<Reaction Scheme 2>

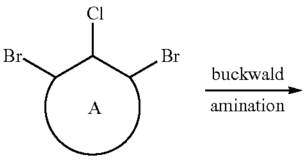

-continued

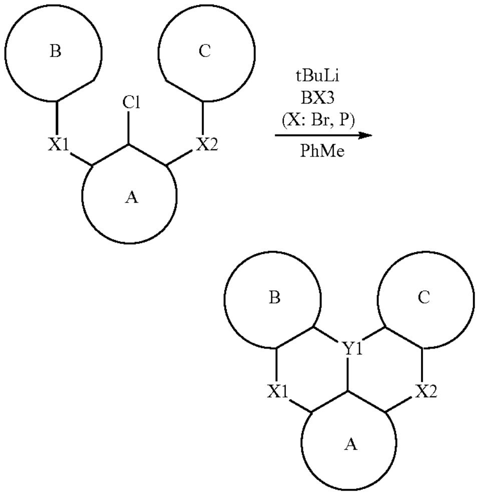

In Reaction Scheme 2, the definitions of A, B, C, X1, X2, and Y1 are the same as those defined in the above-described Formula 2.

When one member is disposed "on" another member in the present application, this includes not only a case where the one member is brought into contact with another member, but also a case where still another member is present between the two members.

When one part "includes" one constituent element in the present application, unless otherwise specifically described, this does not mean that another constituent element is excluded, but means that the another constituent element can be further included.

The organic material layer of the organic light emitting device of the present application can also be composed of a single-layered structure, but can be composed of a multi-layered structure in which two or more organic material layers are stacked. For example, the organic light emitting device of the present invention can have a structure including a hole injection layer, a hole transport layer, a light emitting layer, an electron transport layer, an electron injection layer, and the like as organic material layers. However, the structure of the organic light emitting device is not limited thereto, and can include a fewer number of organic layers.

In an exemplary embodiment of the present application, the organic material layer includes a hole injection layer, a hole transport layer, or a layer which simultaneously injects and transports holes, and the hole injection layer, the hole transport layer, or the layer which simultaneously injects and transports holes includes the compounds of Formulae 1 and 2.

In an exemplary embodiment of the present application, the organic material layer includes a light emitting layer, and the light emitting layer includes the compound of Formula 1.

In another exemplary embodiment, the organic material layer includes a light emitting layer, and the light emitting layer includes the compound of Formula 2.

In still another exemplary embodiment, the organic material layer includes a light emitting layer, and the light emitting layer includes the compound of Formula 1 and the compound of Formula 2.

In an exemplary embodiment of the present application, the organic material layer includes an electron injection layer, an electron transport layer, or a layer which simultaneously injects and transports electrons, and the electron injection layer, the electron transport layer, or the layer which simultaneously injects and transports electrons includes the compounds of Formulae 1 and 2.

In an exemplary embodiment of the present application, the organic light emitting device further includes one or two or more layers selected from the group consisting of a hole injection layer, a hole transport layer, an electron transport layer, an electron injection layer, an electron blocking layer, and a hole blocking layer.

In an exemplary embodiment of the present application, the organic material layer includes a light emitting layer, and the light emitting layer includes the compound of Formula 1 as a host.

In an exemplary embodiment of the present application, the organic material layer includes a light emitting layer, and the light emitting layer includes the compound of Formula 2 as a blue dopant.

The light emitting layer can include an additional host in addition to a compound of Formula 1. Examples of the additional host material include a fused aromatic ring derivative, a hetero ring-containing compound, and the like. Specific examples of the fused aromatic ring derivative include an anthracene derivative, a pyrene derivative, a naphthalene derivative, a pentacene derivative, a phenanthrene compound, a fluoranthene compound, and the like, and specific examples of the hetero ring-containing compound include a dibenzofuran derivative, a ladder-type furan compound, a pyrimidine derivative, and the like, but the examples are not limited thereto.

In an exemplary embodiment of the present application, the organic material layer including the compound of Formula 1 has a thickness of 10 Å to 500 Å.

In an exemplary embodiment of the present application, the organic light emitting device can be a normal type organic light emitting device in which a positive electrode, an organic material layer having one or more layers, and a negative electrode are sequentially stacked on a substrate.

In another exemplary embodiment, the organic light emitting device can be an inverted type organic light emitting device in which a negative electrode, an organic material layer having one or more layers, and a positive electrode are sequentially stacked on a substrate.

Figure 2:
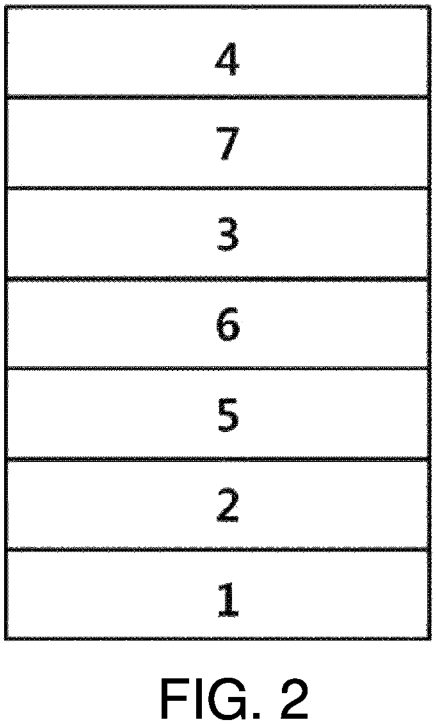
FIG. 2 illustrates an example of an organic light emitting device in which a substrate 1, a positive electrode 2, a hole injection layer 5, a hole transport layer 6, a light emitting layer 3, an electron transport layer 7, and a negative electrode 4 are sequentially stacked.

For example, the structure of the organic light emitting device according to an exemplary embodiment of the present application is exemplified in FIGS. 1 and 2.

FIG. 1 exemplifies a structure of an organic light emitting device in which a substrate 1, a positive electrode 2, a light emitting layer 3, and a negative electrode 4 are sequentially stacked. In the structure described above, the compound can be included in the light emitting layer 3.

FIG. 2 exemplifies a structure of an organic light emitting device in which a substrate 1, a positive electrode 2, a hole injection layer 5, a hole transport layer 6, a light emitting layer 3, an electron transport layer 7, and a negative electrode 4 are sequentially stacked.

In an exemplary embodiment of the present specification, the organic light emitting device can have a structure in which a substrate, a positive electrode, a hole injection layer, a hole transport layer, a light emitting layer, an electron transport layer, an electron injection layer, and a negative electrode are sequentially stacked.

In the structure described above, the compounds of Formulae 1 and 2 can be each included in one or more layers of the hole injection layer, the hole transport layer, the light emitting layer, and the electron transport layer.

When the organic light emitting device includes a plurality of organic material layers, the organic material layers can be formed of the same material or different materials.

The organic light emitting device of the present application can be manufactured by the materials and methods known in the art, except that one or more layers of the organic material layer include the compound, that is, the compound of Formula 1 and the compound of Formula 2.

For example, the organic light emitting device of the present application can be manufactured by sequentially stacking a first electrode, an organic material layer, and a second electrode on a substrate. In this case, the organic light emitting device can be manufactured by depositing a metal or a metal oxide having conductivity, or an alloy thereof on a substrate to form a positive electrode, forming an organic material layer including a hole injection layer, a hole transport layer, a light emitting layer, and an electron transport layer thereon, and then depositing a material, which can be used as a negative electrode, thereon, by using a physical vapor deposition (PVD) method such as sputtering or e-beam evaporation. In addition to the method described above, an organic light emitting device can be made by sequentially depositing a negative electrode material, an organic material layer, and a positive electrode material on a substrate.

Further, the compounds of Formulae 1 and 2 can be formed as an organic material layer by not only a vacuum deposition method, but also a solution application method when an organic light emitting device is manufactured. Here, the solution application method means spin coating, dip coating, doctor blading, inkjet printing, screen printing, a spray method, roll coating, and the like, but is not limited thereto.

In addition to the method described above, an organic light emitting device can also be made by sequentially depositing a negative electrode material, an organic material layer, and a positive electrode material on a substrate (International Publication No. WO2003/012890). However, the manufacturing method is not limited thereto.

In an exemplary embodiment of the present application, the first electrode is a positive electrode, and the second electrode is a negative electrode.

In another exemplary embodiment, the first electrode is a negative electrode, and the second electrode is a positive electrode.

As the positive electrode material, materials having a high work function are usually preferred so as to facilitate the injection of holes into an organic material layer. Specific examples of the positive electrode material which can be used in the present invention include: a metal such as vanadium, chromium, copper, zinc, and gold, or an alloy thereof; a metal oxide such as zinc oxide, indium oxide, indium tin oxide (ITO), and indium zinc oxide (IZO); a combination of a metal and an oxide, such as ZnO:Al or $SnO_2$:Sb; a conductive polymer such as poly(3-methylthiophene), poly[3,4-(ethylene-1,2-dioxy)thiophene] (PEDOT), polypyrrole, and polyaniline; and the like, but are not limited thereto.

As the negative electrode material, materials having a low work function are usually preferred so as to facilitate the injection of electrons into an organic material layer. Specific examples of the negative electrode material include: a metal such as magnesium, calcium, sodium, potassium, titanium, indium, yttrium, lithium, gadolinium, aluminum, silver, tin, and lead, or an alloy thereof; a multi-layer structured material, such as LiF/Al or $LiO_2$/Al; and the like, but are not limited thereto.

The hole injection layer is a layer which injects holes from an electrode, and a hole injection material is preferably a compound which has a capability of transporting holes and thus has an effect of injecting holes at a positive electrode and an excellent effect of injecting holes into a light emitting layer or a light emitting material, prevents excitons produced from the light emitting layer from moving to an electron injection layer or an electron injection material, and is also excellent in the ability to form a thin film. The highest occupied molecular orbital (HOMO) of the hole injection material is preferably a value between the work function of the positive electrode material and the HOMO of the neighboring organic material layer. Specific examples of the hole injection material include metal porphyrin, oligothiophene, arylamine-based organic materials, hexanitrile hexaazatriphenylene-based organic materials, quinacridone-based organic materials, perylene-based organic materials, anthraquinone, polyaniline-based and polythiophene-based conductive polymers, and the like, but are not limited thereto.

The hole transport layer is a layer which accepts holes from a hole injection layer and transports the holes to a light emitting layer, and a hole transport material is suitably a material having high hole mobility which can accept holes from a positive electrode or a hole injection layer and transfer the holes to a light emitting layer. Specific examples thereof include arylamine-based organic materials, conductive polymers, block copolymers having both conjugated portions and non-conjugated portions, and the like, but are not limited thereto.

The light emitting material is a material which can receive holes and electrons from a hole transport layer and an electron transport layer, respectively, and combine the holes and the electrons to emit light in a visible light region, and is preferably a material having high quantum efficiency for fluorescence or phosphorescence. Specific examples thereof include: 8-hydroxy-quinoline aluminum complexes ($Alq_3$); carbazole-based compounds; dimerized styryl compounds; BAlq; 10-hydroxybenzoquinoline-metal compounds; benzoxazole-based, benzothiazole-based and benzimidazole-based compounds; poly(p-phenylene-vinylene) (PPV)-based polymers; spiro compounds; polyfluorene; rubrene; and the like, but are not limited thereto.

The electron transport layer is a layer which accepts electrons from an electron injection layer and transports the electrons to a light emitting layer, and an electron transport material is suitably a material having high electron mobility which can proficiently accept electrons from a negative electrode and transfer the electrons to a light emitting layer. Specific examples thereof include: Al complexes of 8-hydroxy-quinoline; complexes including $Alq_3$; organic radical compounds; hydroxyflavone-metal complexes; and the like, but are not limited thereto. The electron transport layer can be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and an electron injection material is preferably a compound which has a capability of transporting electrons, an effect of injecting electrons from a negative electrode, and an excellent effect of injecting electrons into a light emitting layer or a light emitting material, prevents excitons produced from a light emitting layer from moving to a hole injection layer, and is also excellent in the ability to form a thin film. Specific examples thereof include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof; metal complex compounds; nitrogen-containing 5-membered ring derivatives; and the like, but are not limited thereto.

Examples of the metal complex compounds include 8-hydroxyquinolinato lithium, bis(8-hydroxyquinolinato) zinc, bis(8-hydroxyquinolinato) copper, bis(8-hydroxyquinolinato) manganese, tris(8-hydroxyquinolinato) aluminum, tris(2-methyl-8-hydroxyquinolinato) aluminum, tris(8-hydroxyquinolinato) gallium, bis(10-hydroxybenzo[h]quinolinato) beryllium, bis(10-hydroxybenzo[h]-quinolinato) zinc, bis(2-methyl-8-quinolinato) chlorogallium, bis(2-methyl-8-quinolinato) (o-cresolato) gallium, bis(2-methyl-8-quinolinato) (1-naphtholato) aluminum, bis(2-methyl-8-quinolinato) (2-naphtholato) gallium, and the like, but are not limited thereto.

The hole blocking layer is a layer which blocks holes from reaching a negative electrode, and can be generally formed under the same conditions as those of the hole injection layer. Specific examples of a hole blocking material include oxadiazole derivatives or triazole derivatives, phenanthroline derivatives, BCP, aluminum complexes, and the like, but are not limited thereto.

The organic light emitting device according to the present application can be a top emission type, a bottom emission type, or a dual emission type according to the material to be used.

EXAMPLES

Hereinafter, the present specification will be described in detail with reference to Examples for specifically describing the present specification. However, the Examples according to the present specification can be modified in various forms, and it is not interpreted that the scope of the present specification is limited to the Examples described below in detail. The Examples of the present specification are provided to more completely explain the present specification to a person with ordinary skill in the art.

Synthesis Examples

Synthesis Example 1. Synthesis of Compound 1

9-bromoanthracene (1 eq), 4-biphenylboronic acid (1.1 eq), tetrakis(triphenylphosphine)palladium(0) ($Pd(PPh_3)_4$) (0.1 eq), and potassium carbonate ($K_2CO_3$) (3 eq) were dissolved in tetrahydrofuran (THF) and water at a ratio of 3:1, and the resulting solution was refluxed under heating. After completion of the reaction, the resulting product was extracted with toluene, washed with water, and then recrystallized with toluene to obtain a compound 9-([1,1'-biphenyl]-4-yl)anthracene with a yield of 85%. The prepared compound was confirmed by a mass spectrometer [cal. m/s: 330.4, exp. m/s (M+) 329.5].

9-([1,1'-biphenyl]-4-yl)anthracene (1 eq) was dissolved in THF, N-bromosuccinimide (1 eq) was dissolved in dimethylformamide (DMF), and the resulting solution was slowly added dropwise thereto at room temperature. After completion of the reaction, a solid produced by adding an excessive amount of water thereto was filtered to obtain a compound 9-([1,1'-biphenyl]-4-yl)-10-bromoanthracene with a yield of 87%. The prepared compound was confirmed by a mass spectrometer [cal. m/s: 409.3, exp. m/s (M+) 408.5].

9-([1,1'-biphenyl]-4-yl)-10-bromoanthracene (1 eq), (3-(naphthalen-1-yl)phenyl)boronic acid (1.1 eq), $Pd(PPh_3)_4$ (0.1 eq), and $K_2CO_3$ (3 eq) were dissolved in tetrahydrofuran (THF) and water at a ratio of 3:1, and the resulting solution was refluxed under heating. After completion of the reaction, the resulting product was extracted with toluene, washed with water, and then recrystallized with toluene to obtain the following Compound 1 with a yield of 81%. The prepared compound was confirmed by a mass spectrometer [cal. m/s: 532.2, exp. m/s (M+) 531.2].

In Synthesis Example 1 and the following Synthesis Examples, cal. m/s is a calculated value for the mass of the prepared compound, and exp. m/s means a measurement result obtained by an actual mass spectrometry of the prepared compound.

For the mass spectrometry, an Expression-S with Plate Express model manufactured by Advion, Inc. was used, and the sample, which was dissolved in THF at a concentration of 1 mg/2 ml, was measured.

Synthesis Examples 2 to 12. Synthesis of Compounds 2 to 12

Compounds 2 to 12 were obtained in the same manner as in Synthesis Example 1, except that the compounds in the following Table 1 were used instead of 4-biphenylboronic acid and (3-(naphthalen-1-yl)phenyl)boronic acid in Synthesis Example 1.

By performing a mass analysis on the compounds prepared in Synthesis Examples 1 to 12, it was confirmed that the compounds were prepared, and the measurement results thereof are shown in the following Table 1.

TABLE 1

| Compound | Reaction Material 1 | Reaction Material 2 | cal. m/s | exp. m/s |
|---|---|---|---|---|
| 1 | 4-biphenylboronic acid | (3-(naphthalen-1-yl)-phenyl)boronic acid | 532.2 | 531.2 |
| 2 | 4-biphenylboronic acid | (4-(phenanthren-9-yl)-phenyl)boronic acid | 582.7 | 581.7 |
| 3 | 4-biphenylboronic acid | (2-(naphthalen-2-yl)-phenyl)boronic acid | 532.2 | 531.2 |
| 4 | 4-biphenylboronic acid | (3-(dibenzo[b,d]furan-2-yl)phenyl)boronic acid | 572.2 | 571.2 |
| 5 | 3-biphenylboronic acid | (4-(naphthalen-2-yl)-phenyl)boronic acid | 532.2 | 531.2 |
| 6 | 3-biphenylboronic acid | (3-(naphthalen-2-yl)-phenyl)boronic acid | 532.2 | 531.2 |
| 7 | 3-biphenylboronic acid | (2-(naphthalen-1-yl)-phenyl)boronic acid | 532.2 | 531.2 |
| 8 | 3-biphenylboronic acid | (4-(dibenzo[b,d]furan-4-yl)phenyl)boronic acid | 572.2 | 571.2 |
| 9 | 2-biphenylboronic acid | (4-(naphthalen-1-yl)-phenyl)boronic acid | 532.2 | 531.2 |
| 10 | 2-biphenylboronic acid | (3-(phenanthren-9-yl)-phenyl)boronic acid | 582.2 | 581.2 |
| 11 | 2-biphenylboronic acid | (2-(naphthalen-2-yl)-phenyl)boronic acid | 532.2 | 531.2 |
| 12 | 2-biphenylboronic acid | (3-(dibenzo[b,d]furan-3-yl)phenyl)boronic acid | 572.2 | 571.2 |

Compounds 1 to 12 prepared as described above are as follows.

-continued
[1]
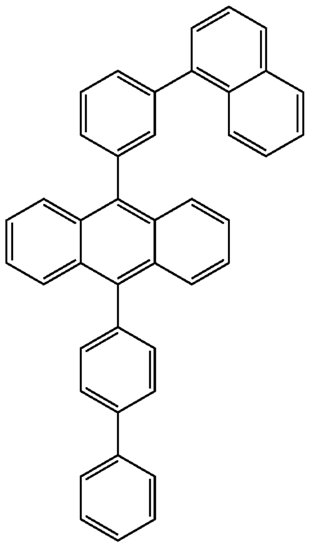
[2]
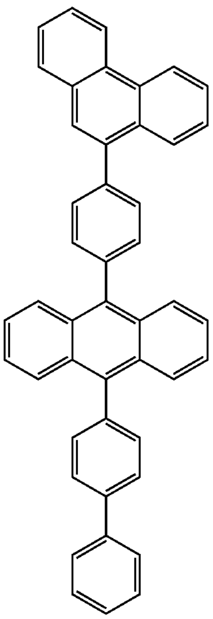
[3]
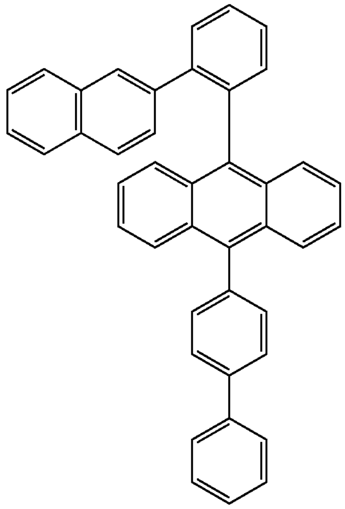
[4]
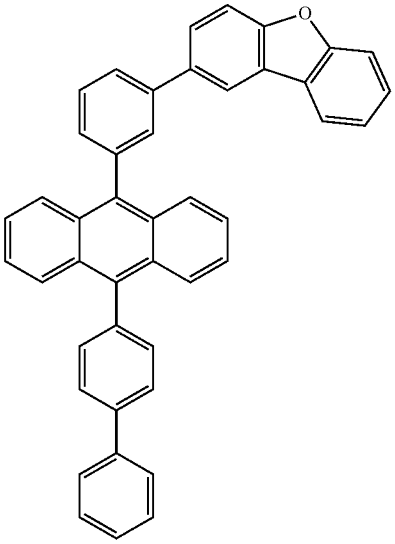
[5]
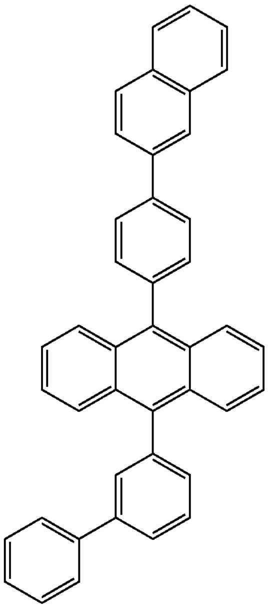

-continued
[6]
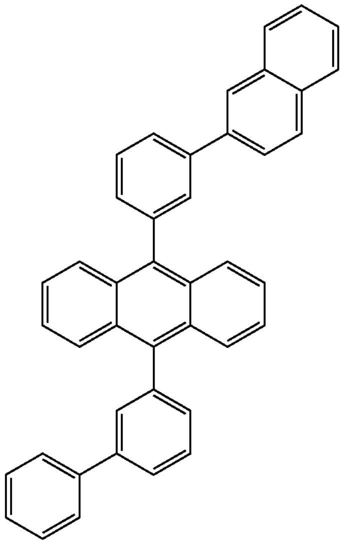
[7]
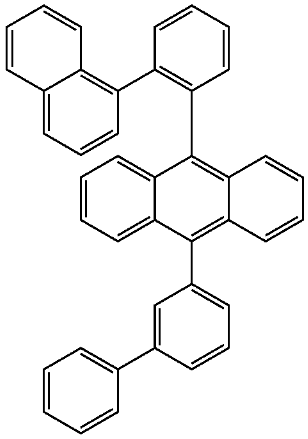
[8]
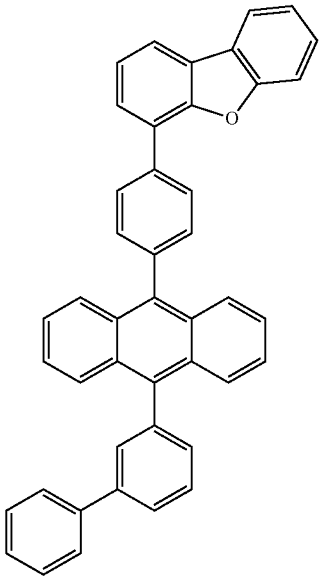
-continued
[9]
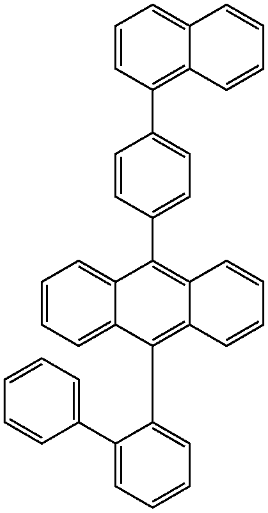
[10]
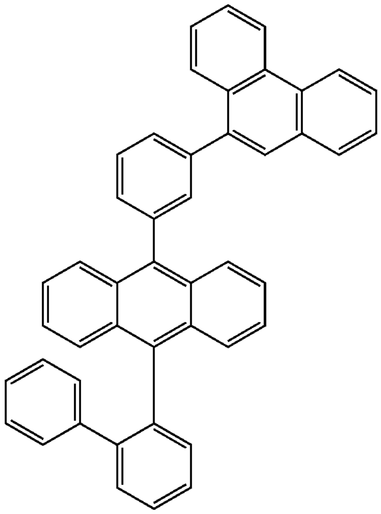
[11]
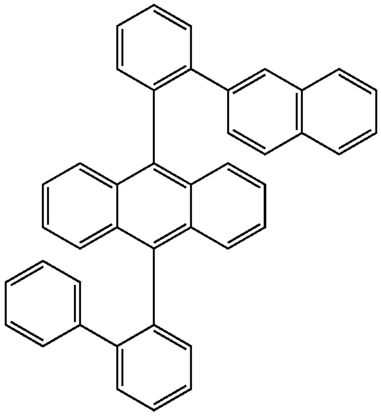

-continued
[12]
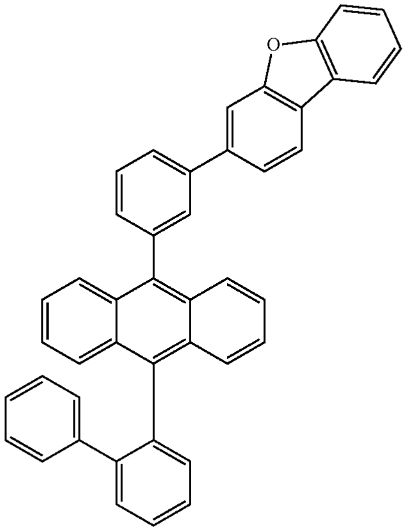
Synthesis Examples 13 to 16. Synthesis of Compounds 13 to 16
The following Compounds 13 to 16 were synthesized by the method described in U.S. Pat. No. 8,890,131 B2.
[13]
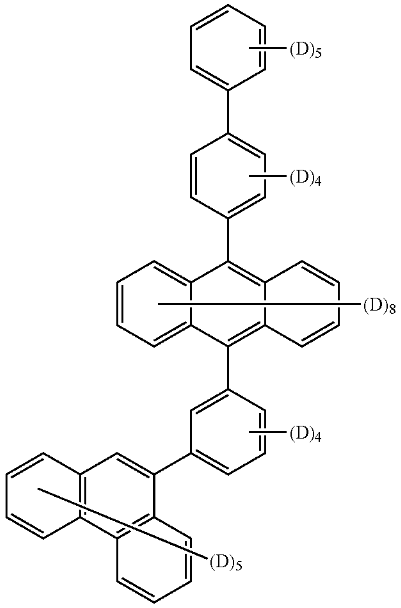
-continued
[14]
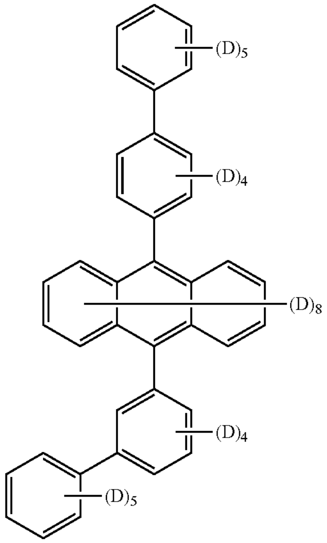
[15]
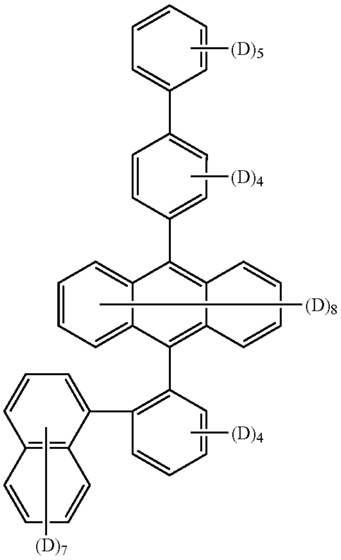

-continued

[16]

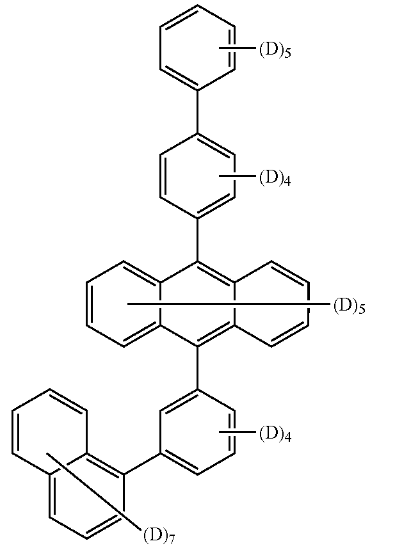

By performing a mass analysis on the compounds prepared in Synthesis Examples 13 to 16, it was confirmed that the compounds were prepared, and the measurement results thereof are shown in the following Table 2.

TABLE 2

| Compound | cal. m/s | exp. m/s |
|---|---|---|
| 13 | 612.4 | 606~611 |
| 14 | 508.3 | 500~505 |
| 15 | 560.3 | 558~560 |
| 16 | 560.3 | 558~560 |

During the polymerization reaction to prepare a compound substituted with deuterium, it can be seen that those in which all the substitutable positions are substituted with deuterium and those in which a part of the substitutable positions are not substituted with deuterium are produced, and thus the exp m/s value is distributed.

Synthesis Example 17. Synthesis of BD-1

After an intermediate 1,3-dibromo-5-chlorobenzene (1 eq), bis(4-(tert-butyl)phenyl)amine (3.0 eq), sodium t-butoxide (3 eq), and bis(tri(tert-butyl)phosphine)-palladium (0)) (0.05 eq) were put into toluene under a nitrogen atmosphere, the resulting solution was heated at 120° C. and stirred for 5 hours. After completion of the reaction, the reaction solution was cooled to room temperature, separated by adding water and aq. $NH_4Cl$ thereto, and then filtered through a treatment with anhydrous magnesium sulfate (anhydrous $MgSO_4$). The filtered solution was distilled off under reduced pressure and purified with recrystallization to obtain N1,N1,N3,N3-tetrakis(4-(tert-butyl)phenyl)-5-chlorobenzene-1,3-diamine with a yield of 58%.

Under a nitrogen atmosphere, N1,N1,N3,N3-tetrakis(4-(tert-butyl)phenyl)-5-chlorobenzene-1,3-diamine (1 eq) and $BI_3$ (1.5 eq) were dissolved in dichlorobenzene, and the resulting solution was stirred at 130° C. for 3 hours. After completion of the reaction, the reaction solution was cooled to room temperature, extracted, and then filtered through a treatment with anhydrous $MgSO_4$. The filtered solution was distilled off under reduced pressure, column-purified (toluene/hexane), and then recrystallized to obtain 2,12-di-tert-butyl-5,9-bis(4-(tert-butyl)phenyl)-7-chloro-5,9-dihydro-5,9-diaza-13b-boranaphtho[3,2,1-de]anthracene with a yield of 65%.

After the intermediate 2,12-di-tert-butyl-5,9-bis(4-(tert-butyl)phenyl)-7-chloro-5,9-dihydro-5,9-diaza-13b-boranaphtho[3,2,1-de]anthracene (1 eq), diphenylamine (1.5 eq), sodium t-butoxide (2 eq), and bis(tri(tert-butyl)phosphine)palladium(0) (0.03 eq) were put into toluene under a nitrogen atmosphere, the resulting solution was heated at 120° C. and stirred for 5 hours. After completion of the reaction, the reaction solution was cooled to room temperature, separated by adding water and aq. $NH_4Cl$ thereto, and then filtered through a treatment with anhydrous $MgSO_4$. The filtered solution was distilled off under reduced pressure and purified with recrystallization to obtain the following compound BD-1 with a yield of 68%. The final compound was confirmed by a mass spectrometer [cal. m/s: 811.97, exp. m/s (M+) 810.6].

BD-1

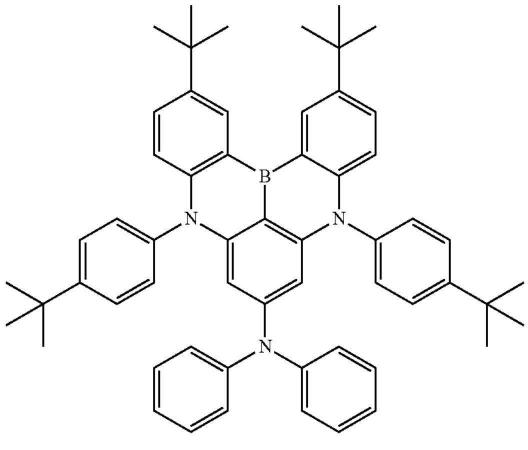

Example 1

A glass substrate thinly coated with indium tin oxide (ITO) to have a thickness of 150 nm was put into distilled water in which a detergent was dissolved, and ultrasonically washed. In this case, a product manufactured by the Fischer Co., was used as the detergent, and distilled water twice filtered using a filter manufactured by Millipore Co., was used as the distilled water. After the ITO was washed for 30 minutes, ultrasonic washing was repeated twice by using distilled water for 10 minutes. After the washing using distilled water was completed, ultrasonic washing was conducted by using isopropyl alcohol, acetone, and methanol solvents, and the resulting product was dried and then transported to a plasma washing machine. The substrate was washed using nitrogen plasma for 5 minutes, and then was transported to a vacuum deposition machine. The following HAT-CN compound was thermally vacuum-deposited to have a thickness of 5 nm on the ITO transparent electrode thus prepared, thereby forming a hole injection layer. Subsequently, the following HTL1 was thermally vacuum-deposited to have a thickness of 100 nm, and then the following HTL2 was thermally vacuum-deposited to have a thickness of 10 nm, thereby forming a hole transport layer. Subsequently, Compound 1 as a host and BD-1 (weight ratio 95:3) as a dopant were simultaneously vacuum-deposited, thereby forming a light emitting layer having a thickness of 20 nm. Subsequently, the following ETL was vacuum-deposited to have a thickness of 20 nm, thereby forming an electron transport layer. Subsequently, LiF was vacuum-deposited to have a thickness of 0.5 nm, thereby forming an electron injection layer. Subsequently, aluminum was deposited to have a thickness of 100 nm to form a negative electrode, thereby manufacturing an organic light emitting device.

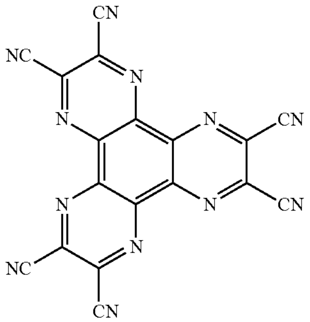

HAT-CN

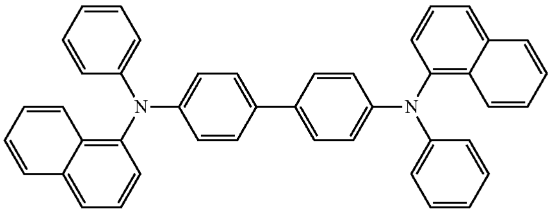

HTL1

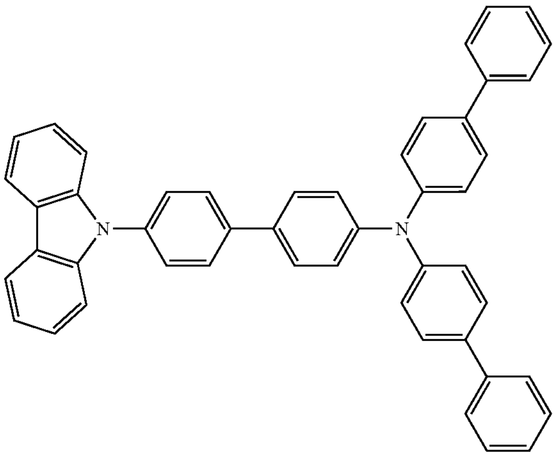

HTL2

-continued

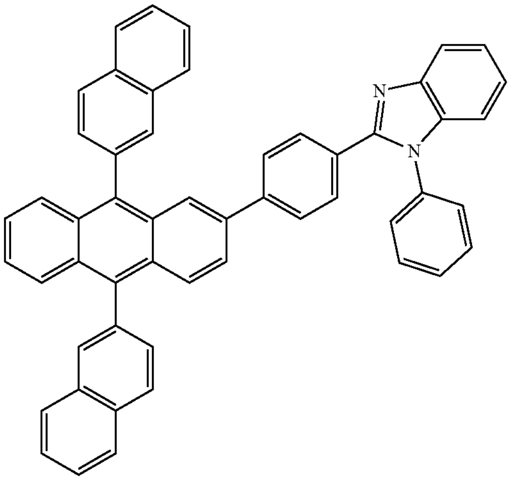

ETL

Examples 2 to 16 organic light emitting devices were manufactured in the same manner as in Example 1, but the organic light emitting devices were manufactured using materials of the following Table 3 as a host and a dopant and contents (parts by weight based on 1 which is the combination of the host and the dopant).

TABLE 3

| | Host | | Dopant | |
|---|---|---|---|---|
| | Material | Content | Material | Content |
| Example 1 | 1 | 0.950 | BD-1 | 0.05 |
| Example 2 | 2 | 0.950 | BD-1 | 0.05 |
| Example 3 | 3 | 0.950 | BD-1 | 0.05 |
| Example 4 | 4 | 0.950 | BD-1 | 0.05 |
| Example 5 | 5 | 0.950 | BD-1 | 0.05 |
| Example 6 | 6 | 0.950 | BD-1 | 0.05 |
| Example 7 | 7 | 0.950 | BD-1 | 0.05 |
| Example 8 | 8 | 0.950 | BD-1 | 0.05 |
| Example 9 | 9 | 0.950 | BD-1 | 0.05 |
| Example 10 | 10 | 0.950 | BD-1 | 0.05 |
| Example 11 | 11 | 0.950 | BD-1 | 0.05 |
| Example 12 | 12 | 0.950 | BD-1 | 0.05 |
| Example 13 | 13 | 0.950 | BD-1 | 0.05 |
| Example 14 | 14 | 0.950 | BD-1 | 0.05 |
| Example 15 | 15 | 0.950 | BD-1 | 0.05 |
| Example 16 | 16 | 0.950 | BD-1 | 0.05 |

Comparative Examples 1 to 6

Organic light emitting devices were manufactured in the same manner as in Example 1, but the organic light emitting devices were manufactured using materials of the following Table 4 as a host and a dopant and contents (parts by weight based on 1 which is the combination of the host and the dopant).

TABLE 4

| | Host | | Dopant | |
|---|---|---|---|---|
| | Material | Content | Material | Content |
| Comparative Example 1 | BH-A | 0.950 | BD-1 | 0.05 |
| Comparative Example 2 | BH-B | 0.950 | BD-1 | 0.05 |
| Comparative Example 3 | BH-C | 0.950 | BD-1 | 0.05 |
| Comparative Example 4 | BH-D | 0.950 | BD-1 | 0.05 |
| Comparative Example 5 | BH-E | 0.950 | BD-1 | 0.05 |
| Comparative Example 6 | BH-F | 0.950 | BD-1 | 0.05 |

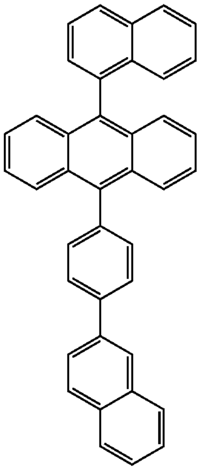

BH-A

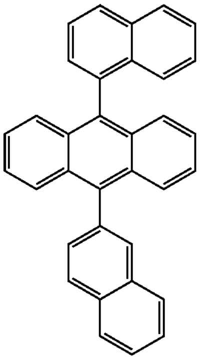

BH-B

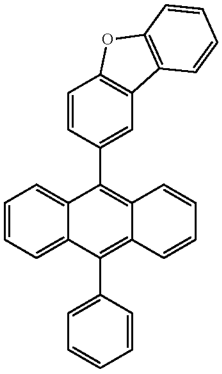

BH-C

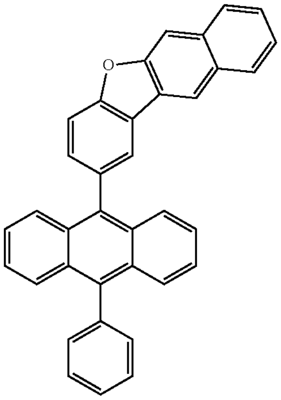

BH-D

TABLE 4-continued

| | Host | | Dopant | |
|---|---|---|---|---|
| | Material | Content | Material | Content |

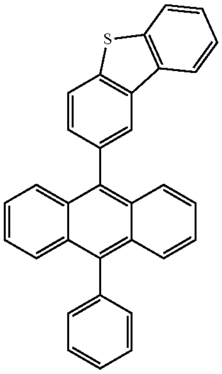

BH-E

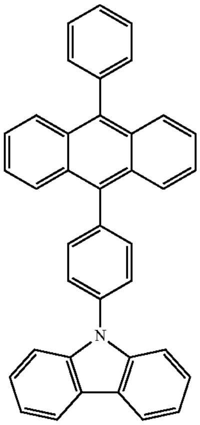

BH-F

Comparative Examples 7 to 28

Organic light emitting devices were manufactured in the same manner as in Example 1, but the organic light emitting devices were manufactured using materials of the following Table 5 as a host and a dopant and contents (parts by weight based on 1 which is the combination of the host and the dopant).

The structure of BD-2 used in Comparative Examples 7 to 28 is as follows.

BD-2

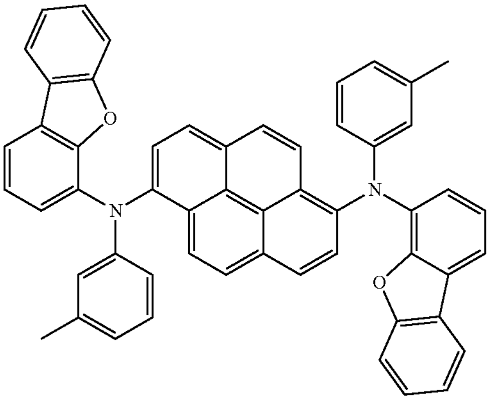

TABLE 5

| | Host | | Dopant | |
|---|---|---|---|---|
| | Material | Content | Material | Content |
| Comparative Example 7 | 1 | 0.950 | BD-2 | 0.05 |
| Comparative Example 8 | 2 | 0.950 | BD-2 | 0.05 |
| Comparative Example 9 | 3 | 0.950 | BD-2 | 0.05 |

TABLE 5-continued

| | Host | | Dopant | |
|---|---|---|---|---|
| | Material | Content | Material | Content |
| Comparative Example 10 | 4 | 0.950 | BD-2 | 0.05 |
| Comparative Example 11 | 5 | 0.950 | BD-2 | 0.05 |
| Comparative Example 12 | 6 | 0.950 | BD-2 | 0.05 |
| Comparative Example 13 | 7 | 0.950 | BD-2 | 0.05 |
| Comparative Example 14 | 8 | 0.950 | BD-2 | 0.05 |
| Comparative Example 15 | 9 | 0.950 | BD-2 | 0.05 |
| Comparative Example 16 | 10 | 0.950 | BD-2 | 0.05 |
| Comparative Example 17 | 11 | 0.950 | BD-2 | 0.05 |
| Comparative Example 18 | 12 | 0.950 | BD-2 | 0.05 |
| Comparative Example 19 | BH-A | 0.950 | BD-2 | 0.05 |
| Comparative Example 20 | BH-B | 0.950 | BD-2 | 0.05 |
| Comparative Example 21 | BH-C | 0.950 | BD-2 | 0.05 |
| Comparative Example 22 | BH-D | 0.950 | BD-2 | 0.05 |
| Comparative Example 23 | BH-E | 0.950 | BD-2 | 0.05 |
| Comparative Example 24 | BH-F | 0.950 | BD-2 | 0.05 |
| Comparative Example 25 | 13 | 0.950 | BD-2 | 0.05 |
| Comparative Example 26 | 14 | 0.950 | BD-2 | 0.05 |
| Comparative Example 27 | 15 | 0.950 | BD-2 | 0.05 |
| Comparative Example 28 | 16 | 0.950 | BD-2 | 0.05 |

The current efficiencies (cd/A) and light emitting efficiencies of the organic light emitting devices manufactured in Examples 1 to 16 and Comparative Examples 1 to 28 were measured at a current density of 10 $mA/cm^2$, the time (LT) when the brightness becomes 950 as compared to the initial brightness was measured at a current density of 20 $mA/cm^2$, and the results thereof are shown in the following Tables 6 to 8.

TABLE 6

| | Current efficiency (cd/A at 10 $mA/cm^2$) | LT (T95%) (hr) |
|---|---|---|
| Example 1 | 7.7 | 160 |
| Example 2 | 7.98 | 160 |
| Example 3 | 7.67 | 165 |
| Example 4 | 7.75 | 170 |
| Example 5 | 7.56 | 155 |
| Example 6 | 7.84 | 155 |
| Example 7 | 7.64 | 153 |
| Example 8 | 7.49 | 159 |
| Example 9 | 7.59 | 160 |
| Example 10 | 7.72 | 171 |
| Example 11 | 7.64 | 165 |
| Example 12 | 7.83 | 165 |
| Example 13 | 7.7 | 210 |
| Example 14 | 7.88 | 200 |
| Example 15 | 7.75 | 220 |
| Example 16 | 7.49 | 250 |

TABLE 7

| | Current efficiency (cd/A at 10 $mA/cm^2$) | LT (T95%) (hr) |
|---|---|---|
| Comparative Example 1 | 6.75 | 138 |
| Comparative Example 2 | 6.52 | 146 |
| Comparative Example 3 | 6.51 | 132 |
| Comparative Example 4 | 6.45 | 147 |
| Comparative Example 5 | 4.26 | 105 |
| Comparative Example 6 | 4.75 | 60 |

TABLE 8

| | Current efficiency (cd/A at 10 $mA/cm^2$) | LT (T95%) (hr) |
|---|---|---|
| Comparative Example 7 | 6.31 | 105 |
| Comparative Example 8 | 6.53 | 110 |
| Comparative Example 9 | 6.49 | 112 |
| Comparative Example 10 | 6.35 | 117 |
| Comparative Example 11 | 6.20 | 120 |
| Comparative Example 12 | 6.82 | 100 |
| Comparative Example 13 | 6.26 | 120 |
| Comparative Example 14 | 6.14 | 105 |
| Comparative Example 15 | 6.22 | 106 |
| Comparative Example 16 | 6.33 | 105 |
| Comparative Example 17 | 6.66 | 112 |
| Comparative Example 18 | 6.41 | 120 |
| Comparative Example 19 | 5.55 | 80 |
| Comparative Example 20 | 5.57 | 90 |
| Comparative Example 21 | 5.36 | 95 |
| Comparative Example 22 | 5.31 | 65 |
| Comparative Example 23 | 3.76 | 84 |
| Comparative Example 24 | 4.00 | 50 |
| Comparative Example 25 | 6.31 | 170 |
| Comparative Example 26 | 6.30 | 175 |
| Comparative Example 27 | 6.20 | 170 |
| Comparative Example 28 | 6.38 | 180 |

When Table 6 is compared with Table 7, it can be confirmed that the case where a compound (compound of Formula 1) in which both Nos. 9 and 10 positions of anthracene are substituted with a phenylene group is applied as a host (Examples 1 to 12) exhibits better current efficiency and service life than the case where a compound in which at least one of Nos. 9 and 10 positions of anthracene is substituted with another substituent instead of a phenylene group is applied as a host (Comparative Examples 1 to 6).

In particular, it can be confirmed that in the case of the compound substituted with deuterium among the compounds of Formula 1 (Examples 13 to 16), the stability of the molecule is increased, and the service lives of the devices are much improved.

When Table 6 is compared with Table 8, it can be confirmed that when the compound of Formula 2 is not included as a dopant even though the compound of Formula 1 is included as a host (Comparative Examples 7 to 18 and Comparative Examples 25 to 28), the current efficiencies and service lives of the devices are decreased.

From this, it can be confirmed that only when the compound of Formula 1 is included as a host and the compound of Formula 2 is included as a dopant, excellent performance is exhibited.

The invention claimed is:

1. An organic light emitting device, comprising:

a first electrode;

a second electrode provided to face the first electrode; and an organic material layer having one or more layers provided between the first electrode and the second electrode, wherein a compound of the following Formula 1 is included as a host in the organic material layer having one or more layers, and a compound of the following Formula 2 is included as a dopant in the organic material layer having one or more layers:

Formula 1

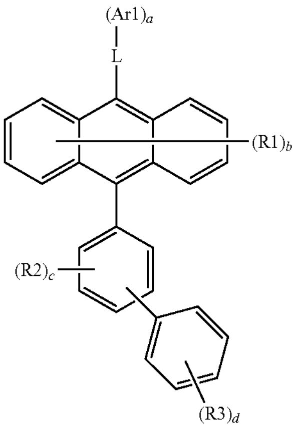

wherein in Formula 1:

L is a phenylene group which is unsubstituted or substituted deuterium;

Ar1 is a dibenzofuran group that is unsubstituted or substituted with deuterium, or dibenzothiophene group that is unsubstituted or substituted with deuterium;

R1 is hydrogen or deuterium;

R2 and R3 the same as or different from each other, and are each independently hydrogen or deuterium;

a is 1;

b is an integer from 1 to 8;

c is an integer from 1 to 4;

d is an integer from 1 to 5;

when a is 2 or more, two or more Ar1s are the same as or different from each other, when b is 2 or more, two or more R1s are the same as or different from each other, when c is 2 or more, two or more R2s are the same as or different from each other, and when d is 2 or more, two or more R3s are the same as or different from each other;

Formula 2

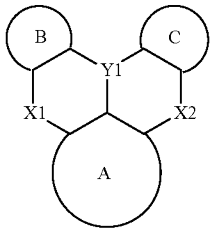

wherein in Formula 2:

A, B, and C are each a benzene ring that is unsubstituted or substituted with an alkyl group or an amine group, where the amine group is unsubstituted or substituted with a phenyl group;

Y1 is boron;

X1 and X2 are each NR;

R is a phenyl group that is unsubstituted or substituted with an alkyl group.

2. The organic light emitting device of claim 1, wherein the compound of Formula 1 is selected from among the following compounds:

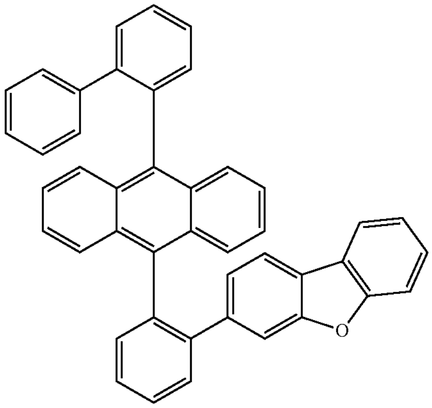

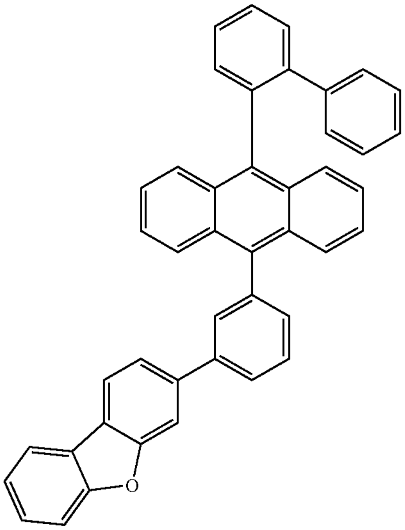

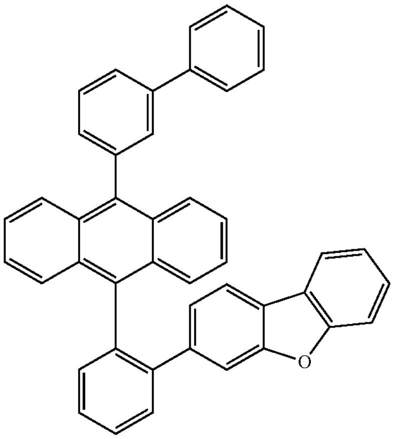

-continued
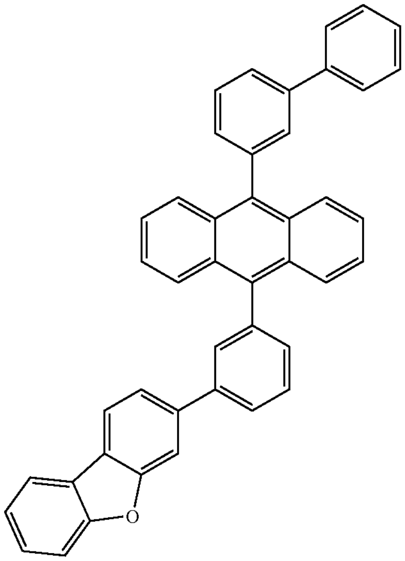
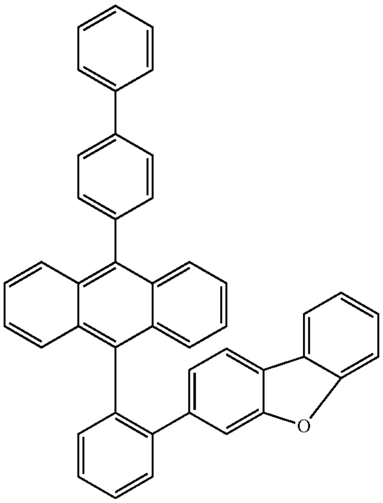
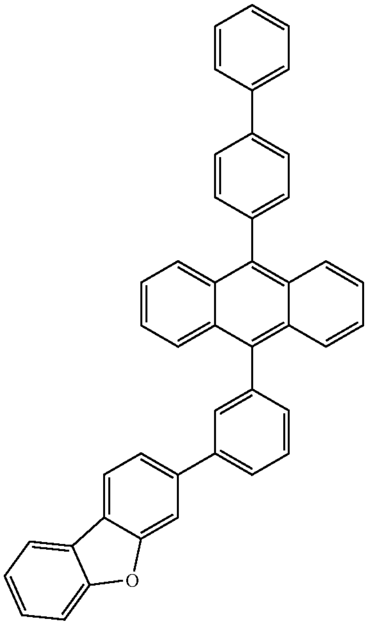
-continued
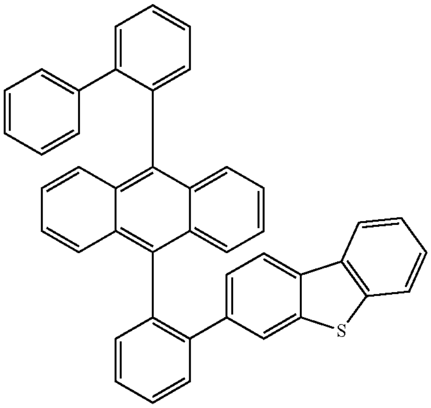
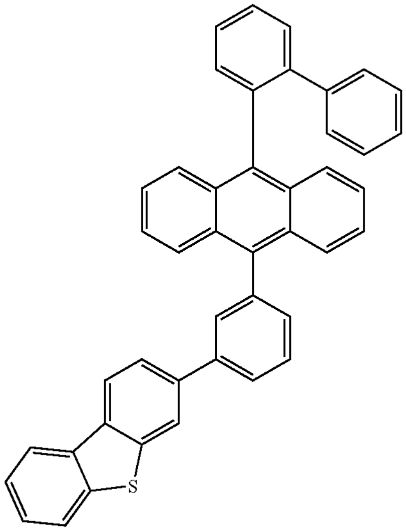
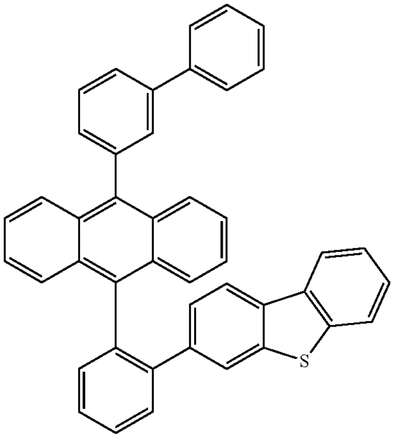

-continued
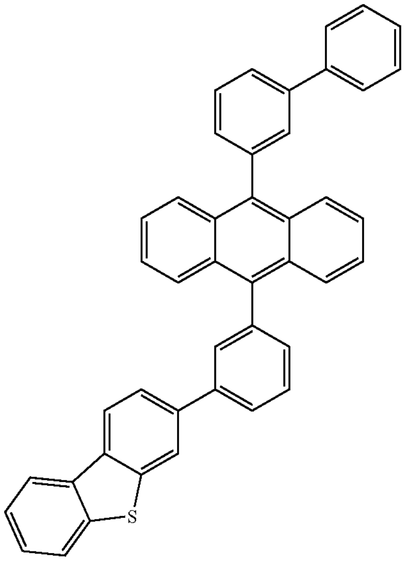
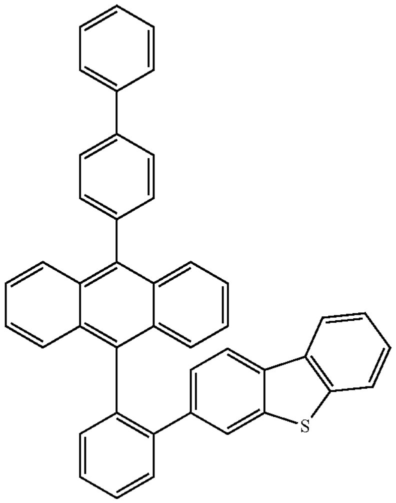
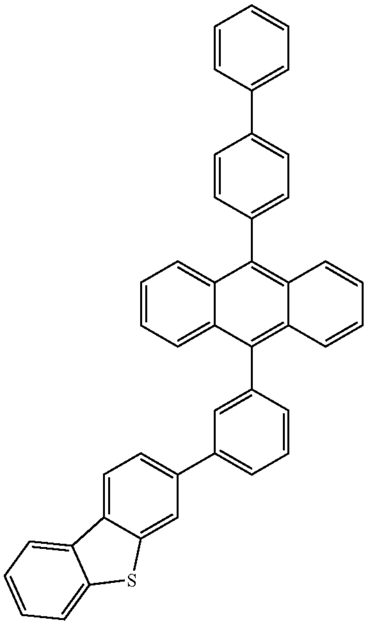
-continued
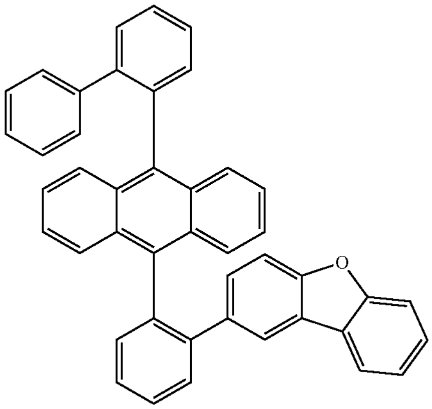
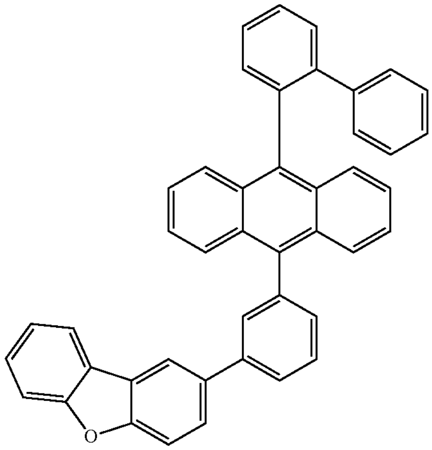
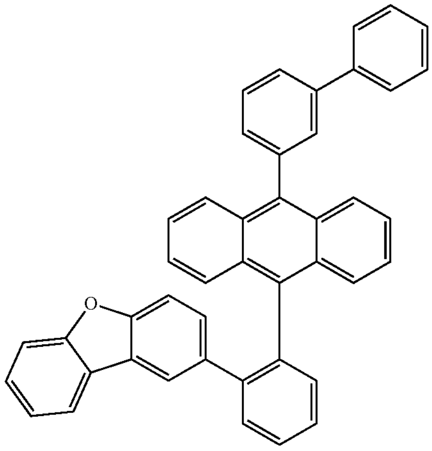

-continued
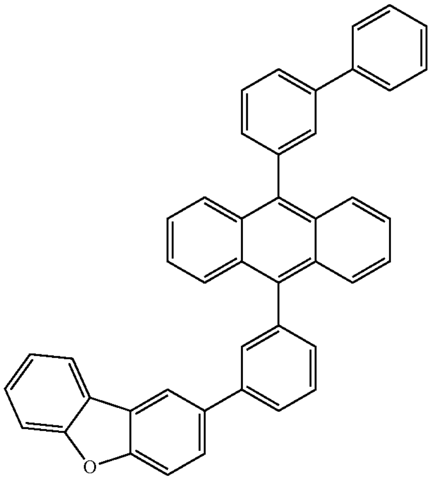
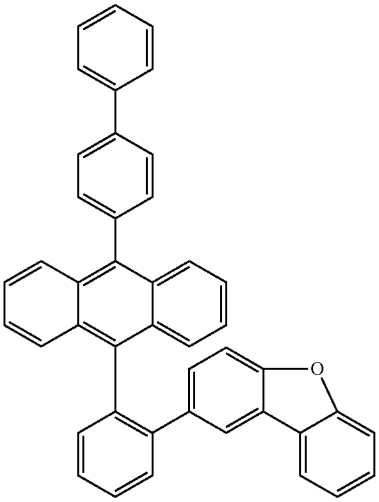
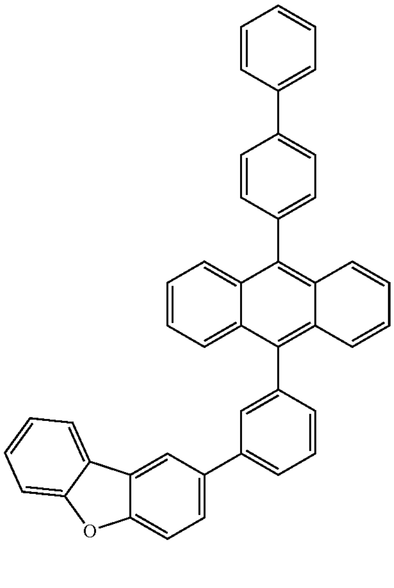
-continued
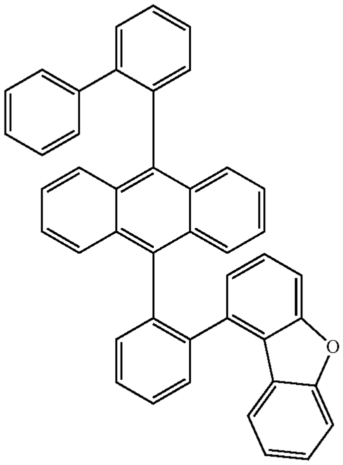
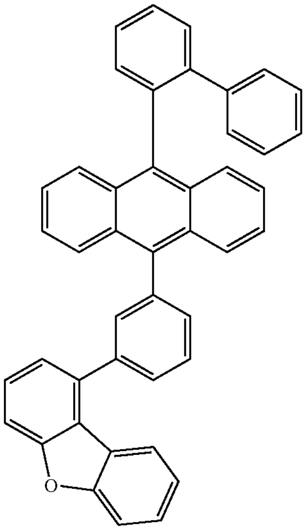
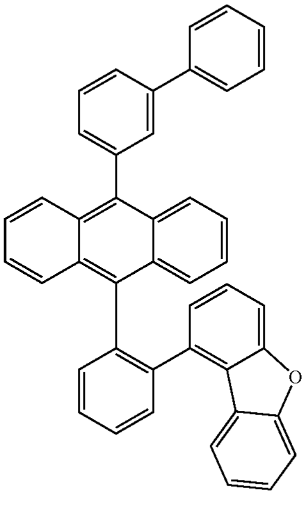

-continued
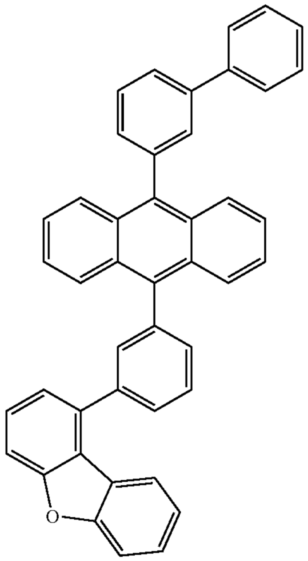
-continued
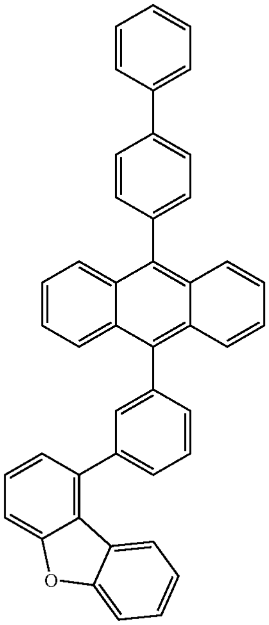
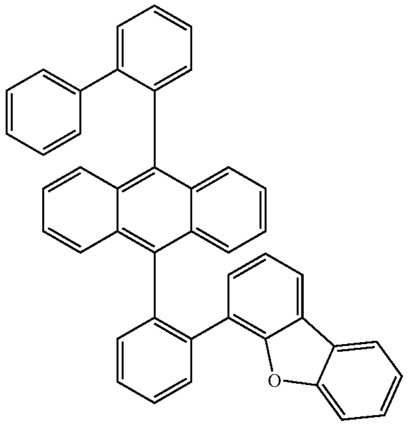
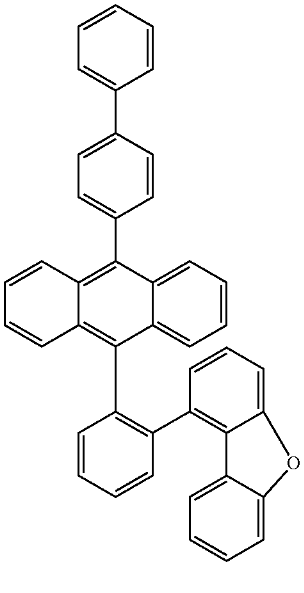
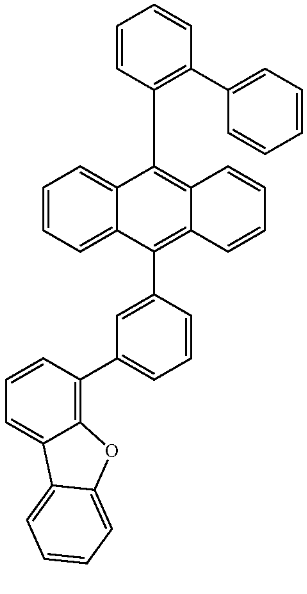

-continued
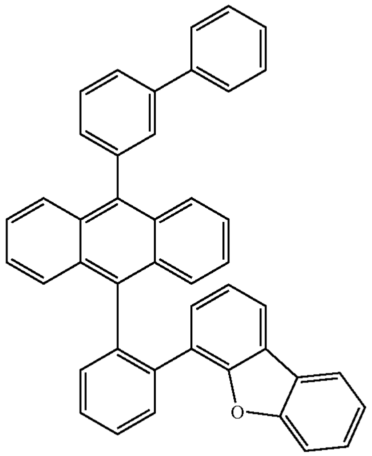
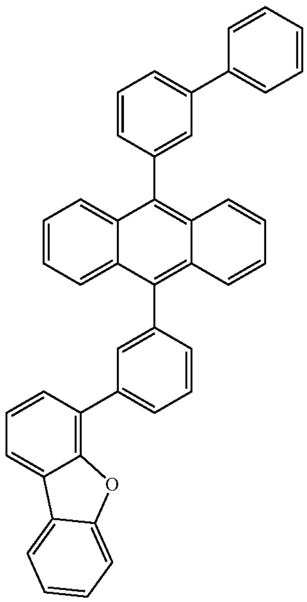
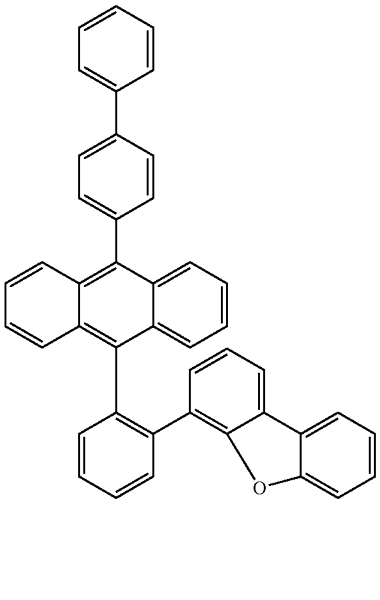
-continued
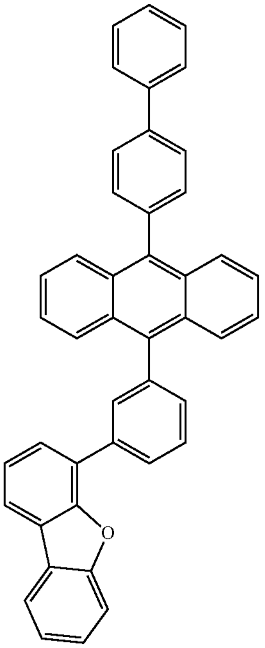
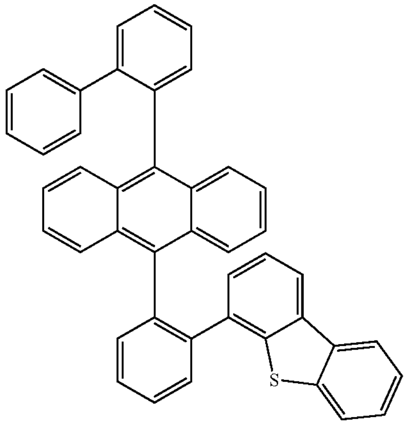
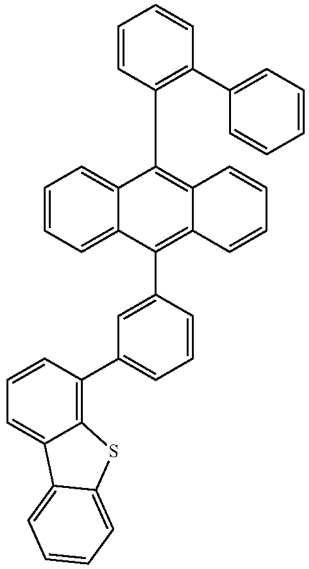

-continued
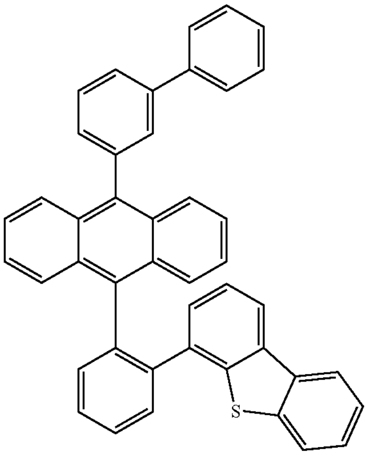
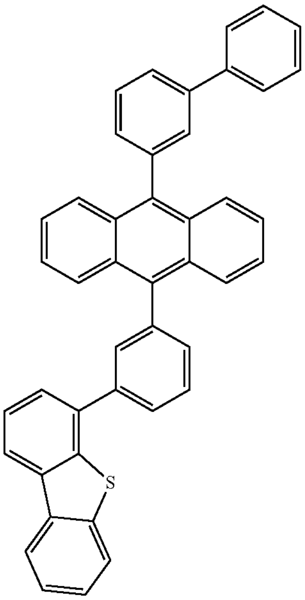
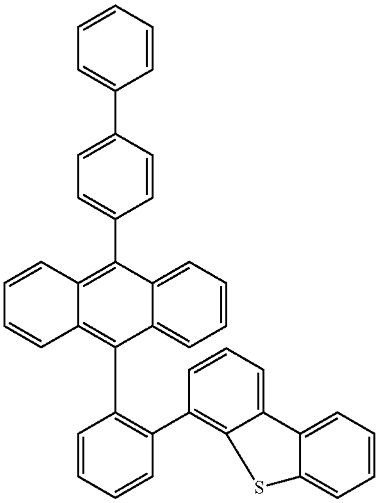
-continued
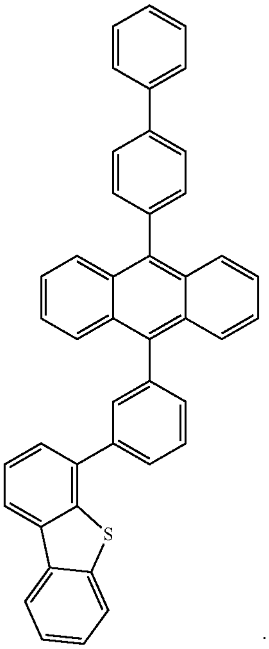 [SMILES: c1ccc(-c2ccc(-c3c4ccccc4c(-c4cccc(-c5cccc6c5sc5ccccc56)c4)c4ccccc34)cc2)cc1]
3. The organic light emitting device of claim 1, wherein the compound of Formula 2 is selected from among the following compounds:
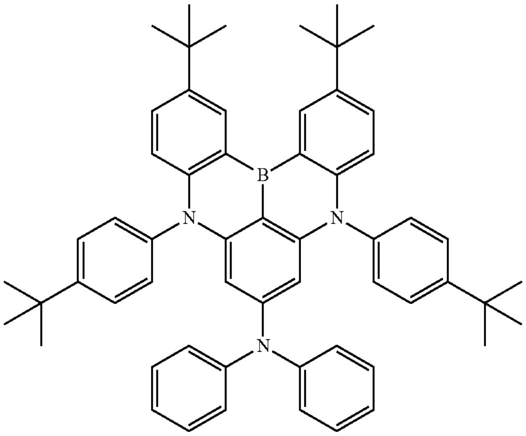
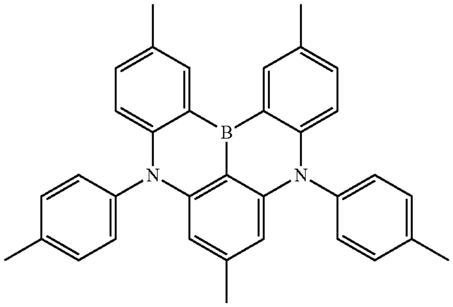

-continued

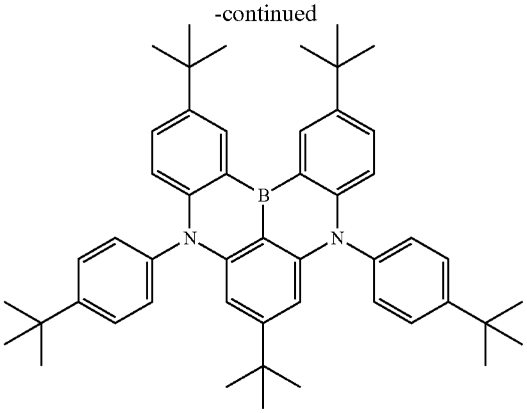

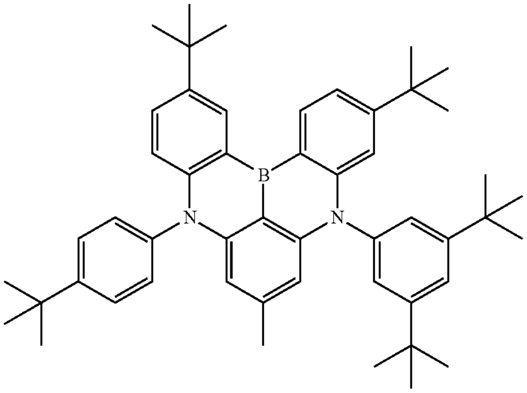

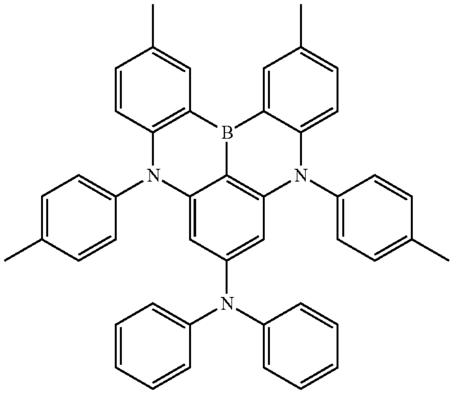

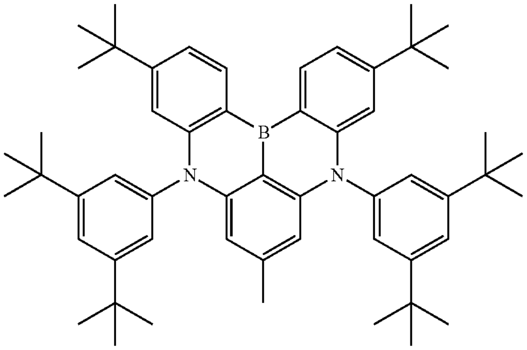

-continued

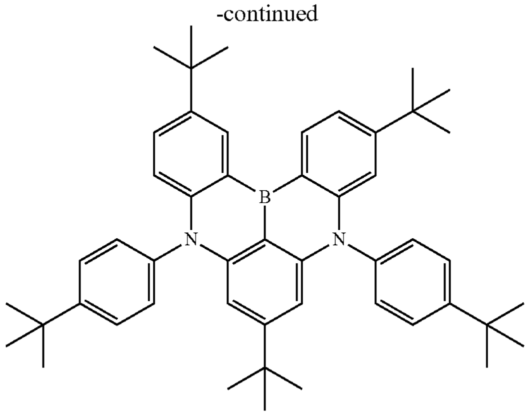

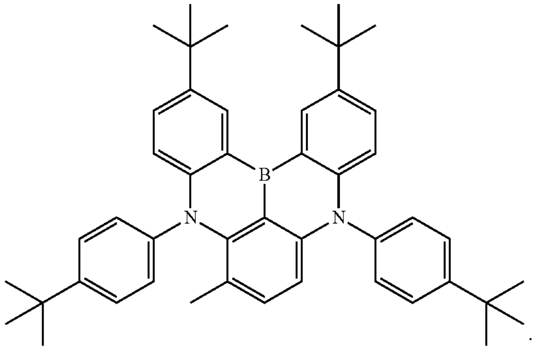

4. The organic light emitting device of claim 1, wherein the organic material layer comprises a light emitting layer, and the light emitting layer comprises the compounds of Formulae 1 and 2.

5. The organic light emitting device of claim 1, wherein the organic material layer comprises an electron injection layer, an electron transport layer, or a layer which simultaneously injects and transports electrons, and the electron injection layer, the electron transport layer, or the layer which simultaneously injects and transports electrons comprises the compounds of Formulae 1 and 2.

6. The organic light emitting device of claim 1, wherein the organic material layer comprises a hole injection layer, a hole transport layer, or a layer which simultaneously injects and transports holes, and the hole injection layer, the hole transport layer, or the layer which simultaneously injects and transports holes comprises the compounds of Formulae 1 and 2.

7. The organic light emitting device of claim 1, wherein the organic material layer comprises a light emitting layer, and the light emitting layer comprises the compound of Formula 2 as a blue dopant.

* * * * *